United States Patent
Liu

(10) Patent No.: US 9,403,891 B2
(45) Date of Patent: Aug. 2, 2016

(54) METHODS AND COMPOSITIONS FOR MODULATING TNF/TNFR SIGNALING

(75) Inventor: Chuan-Ju Liu, Orange, CT (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/003,756

(22) PCT Filed: Mar. 9, 2012

(86) PCT No.: PCT/US2012/028458
§ 371 (c)(1),
(2), (4) Date: Nov. 1, 2013

(87) PCT Pub. No.: WO2012/122464
PCT Pub. Date: Sep. 13, 2012

(65) Prior Publication Data
US 2014/0045756 A1 Feb. 13, 2014

Related U.S. Application Data

(60) Provisional application No. 61/451,190, filed on Mar. 10, 2011.

(51) Int. Cl.
| | |
|---|---|
| C07K 14/475 | (2006.01) |
| A61K 45/06 | (2006.01) |
| A61K 38/18 | (2006.01) |
| C07K 14/525 | (2006.01) |
| C07K 14/705 | (2006.01) |
| A61K 38/00 | (2006.01) |

(52) U.S. Cl.
CPC .............. *C07K 14/475* (2013.01); *A61K 38/18* (2013.01); *A61K 45/06* (2013.01); *C07K 14/525* (2013.01); *C07K 14/70578* (2013.01); *A61K 38/00* (2013.01)

(58) Field of Classification Search
CPC ....... A61K 38/00; A61K 38/18; A61K 45/06; C07K 14/475; C07K 14/525; C07K 14/70578
See application file for complete search history.

(56) References Cited

U.S. PATENT DOCUMENTS

| | | |
|---|---|---|
| 2003/0180258 A1 | 9/2003 | Van Es et al. |
| 2004/0071660 A1 | 4/2004 | Havenga et al. |
| 2010/0298232 A1 | 11/2010 | Liu |

FOREIGN PATENT DOCUMENTS

| | | | |
|---|---|---|---|
| WO | WO-2008/094687 A2 | 8/2008 | |
| WO | WO-2010/120374 | 10/2010 | |
| WO | WO 2011140086 A2 * | 11/2011 | ............. C07K 14/78 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
UniProt Protein Database, Protein Accession P28799, Granulins, pp. 1-12, accessed on Dec. 18, 2014.*
Anakwe, Onyeama O. et al., "Acrosome Biogenesis Begins during Meiosis: Evidence from the Synthesis and Distribution of an Acrosomal Glycoprotein, Acrogranin, during Guinea Pig Spermatogenesis," Biol Reprod, (1990), 42(2), pp. 317-328.
Attur, M.G. et al., "'A System biology' approach to bioinformatics and functional genomics in complex human diseases: arthritis," Curr Issues Mol Biol, (2002), 4(4), pp. 129-146.
Baba, Tadashi et al., "Acrogranin, an Acrosomal Cysteine-Rich Glycoprotein, is the Precursor of the Growth-Modulating Peptides, Granulins, and Epithelins, and is Expressed in Somatic as Well as Male Germ Cells," Mol Rprod Dev, (1993), 34(3), pp. 233-243.
Barreda, Daniel R. et al., "Differentially expressed genes that encode potential markers of goldfish macrophage development in vitro," Dev Comp Immunol, 28(7-8), (2004), pp. 727-746.
Feng, Jian Q. et al., "Granulin epithelin precursor: a bone morphogenic protein 2-inducible growth factor that activates Erk1/2 signaling and JunB transcription factor in chondrogenesis," FASEB, (Jun. 2010), vol. 24, No. 6, pp. 1879-1892.
International Search Report and Written Opinion issued in Application No. PCT/US2012/28458 mailed Jun. 22, 2012 (7 pages).
Xu, Ke et al., "Cartilage oligomeric matrix protein associates with granulin-epithelin precursor (GEP) and potentiates GEP-stimulated chondrocyte proliferation," J Biol Chem, (Apr. 13, 2007), vol. 282, No. 15, pp. 11347-11355.

* cited by examiner

*Primary Examiner* — James H Alstrum Acevedo
*Assistant Examiner* — Erinne Dabkowski
(74) *Attorney, Agent, or Firm* — Foley & Lardner LLP

(57) ABSTRACT

The present disclosure relates to methods and compositions for modulating TNF and TNFR signaling. In particular, the disclosure describes methods and compositions for inhibiting TNFα signaling, such as in the prevention or treatment of TNFα-related diseases.

11 Claims, 26 Drawing Sheets

SEQUENCE LISTING

<160> NUMBER OF SEQ ID NOS: 28

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

```
Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
        290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
                340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
        370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Gly His Phe Cys His
        515                 520                 525

Asp Asn Gln Thr Cys Cys Arg Asp Asn Arg Gln Gly Trp Ala Cys Cys
530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 2
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30
```

His Pro Leu Ala Lys Lys Leu Pro Ala Gln Arg Thr Asn Arg Ala Val
            35                  40                  45

Ala Leu Ser Ser Ala Ser Ser Lys Glu Asn Ala Thr Thr Asp Leu
 50                  55                  60

Leu Thr Lys Leu Pro Ala His Thr Val Gly Asp Val Lys Cys Asp Met
 65                  70                  75                  80

Glu Val Ser Cys Pro Asp Gly Tyr Thr Cys Cys Arg Leu Gln Ser Gly
                 85                  90                  95

Ala Trp Pro Trp Cys Glu Gln Gly Pro His Gln Val Pro Trp Met Glu
                100                 105                 110

Lys Ala Pro Ala His Leu Ser Leu Pro Asp Pro Gln Ala Leu Lys Arg
                115                 120                 125

Asp Val Pro Cys Asp Asn Val Ser Ser Cys Pro Ser Ser Asp Thr Cys
            130                 135                 140

Cys Gln Leu Thr Ser Gly Glu Trp Gly Cys Cys Pro Ile Pro
145                 150                 155

<210> SEQ ID NO 3
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ile Leu Pro Gln Ala Ser Cys Cys Glu Asp Arg Val His Cys Cys
1               5                   10                  15

Pro His Gly Ala Phe Cys Asp Leu Val His Thr Arg Cys Ile Thr Pro
                20                  25                  30

Thr Gly Thr His Pro Leu Ala Lys Lys Leu Pro Ala Gln Arg Thr Asn
            35                  40                  45

Arg Ala Val Ala Leu Ser Ser Ser Lys Glu Asn Ala Thr Thr Asp
 50                  55                  60

Leu Leu Thr Lys Leu Pro Ala His Thr Val Gly Asp Val Lys Cys Asp
 65                  70                  75                  80

Met Glu Val Ser Cys Pro Asp Gly Tyr Thr Cys Cys Arg Leu Gln Ser
                 85                  90                  95

Gly Ala Trp Cys Glu Gln Gly Pro His Gln Val Pro Trp Met Glu Lys
                100                 105                 110

Ala Pro Ala His Leu Ser Leu Pro Asp Pro Gln Ala Leu Lys Arg Asp
                115                 120                 125

Val Pro Cys Asp Asn Val Ser Ser Cys Pro Ser Ser Asp Thr Cys Cys
            130                 135                 140

Gln Leu Thr Ser Gly Glu Trp Gly Cys Cys Pro Ile Pro
145                 150                 155

<210> SEQ ID NO 4
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 4

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Lys Glu Asn Ala Thr Thr Asp Leu Leu Thr
    50                  55                  60

Lys Leu Pro Ala His Thr Val Gly Asp Val Lys Cys Asp Met Glu Val
65              70                  75                  80

Ser Cys Pro Asp Gly Tyr Thr Cys Cys Arg Leu Gln Ser Gly Ala Trp
                85                  90                  95

Cys Glu Gln Gly Pro His Gln Val Pro Trp Met Glu Lys Ala Pro Ala
            100                 105                 110

His Leu Ser Leu Pro Asp Pro Gln Ala Leu Lys Arg Asp Val Pro Cys
        115                 120                 125

Asp Asn Val Ser Ser Cys Pro Ser Ser Asp Cys Cys Gln Leu Thr
    130                 135                 140

Ser Gly Glu Trp Gly Cys Cys Pro Ile Pro
145                 150

<210> SEQ ID NO 5
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Gln Ala Ser Cys Cys Glu Asp Arg Val His Cys Cys Pro His
1               5                   10                  15

Gly Ala Phe Cys Asp Leu Val His Thr Arg Cys Ile Thr Pro Thr Gly
            20                  25                  30

Thr His Pro Leu Ala Lys Lys Leu Pro Ala Gln Arg Thr Asn Arg Ala
        35                  40                  45

Val Ala Leu Ser Ser Ser Lys Glu Asn Ala Thr Thr Asp Leu Leu
    50                  55                  60

Thr Lys Leu Pro Ala His Thr Val Gly Asp Val Lys Cys Asp Met Glu
65              70                  75                  80

Val Ser Cys Pro Asp Gly Tyr Thr Cys Cys Arg Leu Gln Ser Gly Ala
                85                  90                  95

Trp Cys Glu Gln Gly Pro His Gln Val Pro Trp Met Glu Lys Ala Pro
            100                 105                 110

Ala His Leu Ser Leu Pro Asp Pro Gln Ala Leu Lys Arg Asp Val Pro
        115                 120                 125

Cys Asp Asn Val Ser Ser Cys Pro Ser Ser Asp Thr Cys Cys Gln Leu
    130                 135                 140

Thr Ser Gly Glu Trp Gly Cys Cys Pro Ile Pro
145                 150                 155

<210> SEQ ID NO 6
<211> LENGTH: 156
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 6

Met Leu Pro Gln Ala Ser Cys Cys Glu Asp Arg Val His Cys Cys Pro
1               5                   10                  15

His Gly Ala Phe Cys Asp Leu Val His Thr Arg Cys Ile Thr Pro Thr
            20                  25                  30

Gly Thr His Pro Leu Ala Lys Lys Leu Pro Ala Gln Arg Thr Asn Arg
        35                  40                  45

Ala Val Ala Leu Ser Ser Ser Lys Glu Asn Ala Thr Thr Asp Leu
 50                  55                  60

Leu Thr Lys Leu Pro Ala His Thr Val Gly Asp Val Lys Cys Asp Met
65                  70                  75                  80

Glu Val Ser Cys Pro Asp Gly Tyr Thr Cys Cys Arg Leu Gln Ser Gly
                85                  90                  95

Ala Trp Cys Glu Gln Gly Pro His Gln Val Pro Trp Met Glu Lys Ala
            100                 105                 110

Pro Ala His Leu Ser Leu Pro Asp Pro Gln Ala Leu Lys Arg Asp Val
        115                 120                 125

Pro Cys Asp Asn Val Ser Ser Cys Pro Ser Ser Asp Thr Cys Cys Gln
130                 135                 140

Leu Thr Ser Gly Glu Trp Gly Cys Cys Pro Ile Pro
145                 150                 155

<210> SEQ ID NO 7
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ile Leu Pro Gln Ala Ser Cys Cys Glu Asp Arg Val His Cys Cys
1               5                   10                  15

Pro His Gly Ala Phe Cys Asp Leu Val His Thr Arg Cys Ile Thr Pro
            20                  25                  30

Thr Gly Thr His Pro Leu Ala Lys Lys Leu Pro Ala Gln Arg Thr Asn
        35                  40                  45

Arg Ala Val Ala Leu Ser Ser Ser Lys Glu Asn Ala Thr Thr Asp
 50                  55                  60

Leu Leu Thr Lys Leu Pro Ala His Thr Val Gly Asp Val Lys Cys Asp
65                  70                  75                  80

Met Glu Val Ser Cys Pro Asp Gly Tyr Thr Cys Cys Arg Leu Gln Ser
                85                  90                  95

Gly Ala Trp Cys Glu Gln Gly Pro His Gln Val Pro Trp Met Glu Lys
            100                 105                 110

Ala Pro Ala His Leu Ser Leu Pro Asp Pro Gln Ala Leu Lys Arg Asp
        115                 120                 125

Val Pro Cys Asp Asn Val Ser Ser Cys Pro Ser Ser Asp Thr Cys Cys
130                 135                 140

Gln Leu Thr Ser Gly Glu Trp Gly Cys Cys Pro Ile Pro
145                 150                 155
```

```
<210> SEQ ID NO 8
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Ile Leu Pro Gln Ala Ser Cys Cys Glu Asp Arg Val His Cys
1               5                   10                  15

Cys Pro His Gly Ala Phe Cys Asp Leu Val His Thr Arg Cys Ile Thr
                20                  25                  30

Pro Thr Gly Thr His Pro Leu Ala Lys Lys Leu Pro Ala Gln Arg Thr
            35                  40                  45

Asn Arg Ala Val Ala Leu Ser Ser Ser Lys Glu Asn Ala Thr Thr
50                  55                  60

Asp Leu Leu Thr Lys Leu Pro Ala His Thr Val Gly Asp Val Lys Cys
65                  70                  75                  80

Asp Met Glu Val Ser Cys Pro Asp Gly Tyr Thr Cys Cys Arg Leu Gln
                85                  90                  95

Ser Gly Ala Trp Cys Glu Gln Gly Pro His Gln Val Pro Trp Met Glu
            100                 105                 110

Lys Ala Pro Ala His Leu Ser Leu Pro Asp Pro Gln Ala Leu Lys Arg
        115                 120                 125

Asp Val Pro Cys Asp Asn Val Ser Ser Cys Pro Ser Ser Asp Thr Cys
130                 135                 140

Cys Gln Leu Thr Ser Gly Glu Trp Gly Cys Cys Pro Ile Pro
145                 150                 155

<210> SEQ ID NO 9
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ile Gln Cys Pro Asp Ser Gln Phe Glu Cys Pro Asp Phe Ser Thr Cys
1               5                   10                  15

Cys Val Met Val Asp Gly Ser Trp Gly Cys Cys Pro Met Pro Gln Ala
                20                  25                  30

Ser Cys Cys Glu Asp Arg Val His Cys Cys Pro His Gly Ala Phe Cys
            35                  40                  45

Asp Leu Val His Thr Arg Cys Ile Thr Pro Thr Gly Thr His Pro Ser
50                  55                  60

Lys Glu Asn Ala Thr Thr Asp Leu Leu Thr Lys Leu Pro Ala His Thr
65                  70                  75                  80

Val Gly Asp Val Lys Cys Asp Met Glu Val Ser Cys Pro Asp Gly Tyr
                85                  90                  95

Thr Cys Cys Arg Leu Gln Ser Gly Ala Trp Gly Cys Cys Pro Phe Thr
            100                 105                 110

Gln Ala Val Cys Cys Glu Asp His Ile His Cys Cys Pro Ala Gly Phe
        115                 120                 125

Thr Cys Asp Thr Gln Lys Gly Thr Cys Glu Gln Gly Pro His Gln Val
130                 135                 140
```

Pro Trp Met Glu Lys Ala Pro Ala His Leu Ser Leu Pro Asp Pro Gln
145                 150                 155                 160

Ala Leu Lys Arg Asp Val Pro Cys Asp Asn Val Ser Ser Cys Pro Ser
            165                 170                 175

Ser Asp Thr Cys Cys Gln Leu Thr Ser Gly Glu Trp Gly Cys Cys Pro
        180                 185                 190

Ile Pro Glu Ala Val Cys Cys Ser Asp His Gln His Cys Cys Pro Gln
        195                 200                 205

Gly Tyr Thr Cys Val Ala Glu Gly Gln Cys Gln
        210                 215

<210> SEQ ID NO 10
<211> LENGTH: 222
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Gly Ile Leu Ile Gln Cys Pro Asp Ser Gln Phe Glu Cys Pro Asp Phe
1               5                   10                  15

Ser Thr Cys Cys Val Met Val Asp Gly Ser Trp Gly Cys Cys Pro Met
            20                  25                  30

Pro Gln Ala Ser Cys Cys Glu Asp Arg Val His Cys Cys Pro His Gly
        35                  40                  45

Ala Phe Cys Asp Leu Val His Thr Arg Cys Ile Thr Pro Thr Gly Thr
    50                  55                  60

His Pro Ser Lys Glu Asn Ala Thr Thr Asp Leu Thr Lys Leu Pro
65                  70                  75                  80

Ala His Thr Val Gly Asp Val Lys Cys Asp Met Glu Val Ser Cys Pro
                85                  90                  95

Asp Gly Tyr Thr Cys Cys Arg Leu Gln Ser Gly Ala Trp Gly Cys Cys
            100                 105                 110

Pro Phe Thr Gln Ala Val Cys Cys Glu Asp His Ile His Cys Cys Pro
        115                 120                 125

Ala Gly Phe Thr Cys Asp Thr Gln Lys Gly Thr Cys Glu Gln Gly Pro
    130                 135                 140

His Gln Val Pro Trp Met Glu Lys Ala Pro Ala His Leu Ser Leu Pro
145                 150                 155                 160

Asp Pro Gln Ala Leu Lys Arg Asp Val Pro Cys Asp Asn Val Ser Ser
                165                 170                 175

Cys Pro Ser Ser Asp Thr Cys Cys Gln Leu Thr Ser Gly Glu Trp Gly
            180                 185                 190

Cys Cys Pro Ile Pro Glu Ala Val Cys Cys Ser Asp His Gln His Cys
        195                 200                 205

Cys Pro Gln Gly Tyr Thr Cys Val Ala Glu Gly Gln Cys Gln
    210                 215                 220

<210> SEQ ID NO 11
<211> LENGTH: 223
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

Met Gly Ile Leu Ile Gln Cys Pro Asp Ser Gln Phe Glu Cys Pro Asp
1               5                   10                  15

Phe Ser Thr Cys Cys Val Met Val Asp Gly Ser Trp Gly Cys Cys Pro
            20                  25                  30

Met Pro Gln Ala Ser Cys Cys Glu Asp Arg Val His Cys Cys Pro His
        35                  40                  45

Gly Ala Phe Cys Asp Leu Val His Thr Arg Cys Ile Thr Pro Thr Gly
    50                  55                  60

Thr His Pro Ser Lys Glu Asn Ala Thr Thr Asp Leu Leu Thr Lys Leu
65              70                  75                  80

Pro Ala His Thr Val Gly Asp Val Lys Cys Asp Met Glu Val Ser Cys
                85                  90                  95

Pro Asp Gly Tyr Thr Cys Cys Arg Leu Gln Ser Gly Ala Trp Gly Cys
            100                 105                 110

Cys Pro Phe Thr Gln Ala Val Cys Cys Glu Asp His Ile His Cys Cys
        115                 120                 125

Pro Ala Gly Phe Thr Cys Asp Thr Gln Lys Gly Thr Cys Glu Gln Gly
    130                 135                 140

Pro His Gln Val Pro Trp Met Glu Lys Ala Pro Ala His Leu Ser Leu
145                 150                 155                 160

Pro Asp Pro Gln Ala Leu Lys Arg Asp Val Pro Cys Asp Asn Val Ser
                165                 170                 175

Ser Cys Pro Ser Ser Asp Thr Cys Cys Gln Leu Thr Ser Gly Glu Trp
            180                 185                 190

Gly Cys Cys Pro Ile Pro Glu Ala Val Cys Cys Ser Asp His Gln His
        195                 200                 205

Cys Cys Pro Gln Gly Tyr Thr Cys Val Ala Glu Gly Gln Cys Gln
    210                 215                 220

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggcgaggtc tgactgttgt gg                                              22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctcatcaaa aagttccctg tgc                                             23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tacaagctgg ctggtgggga                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcgcgggtc tcaggacctt                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatctcacag cagcacatca                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaggtgctca tgtcctcatc                                          20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccttcctacc ccaatttcca at                                       22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccactcctt ctgtgactcc ag                                       22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
cttcaccacc atggagaagg c                                              21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacggacaca ttgggggtag                                                20

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Gly Ile Leu
1

<210> SEQ ID NO 23
<211> LENGTH: 53
<212> TYPE: PRT
<213> ORGANISM: Unknown
<220> FEATURE:
<223> OTHER INFORMATION: Description of Unknown: Cysteine-rich
      "granulin" motif polypeptide
<220> FEATURE:
<221> NAME/KEY: MOD_RES
<222> LOCATION: (2)..(7)
<223> OTHER INFORMATION: Any amino acid and this region may encompass
      5-6 residues
<220> FEATURE:
<221> NAME/KEY: MOD_RES
<222> LOCATION: (9)..(13)
<223> OTHER INFORMATION: Any amino acid
<220> FEATURE:
<221> NAME/KEY: MOD_RES
<222> LOCATION: (16)..(23)
<223> OTHER INFORMATION: Any amino acid
<220> FEATURE:
<221> NAME/KEY: MOD_RES
<222> LOCATION: (26)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(37)
<223> OTHER INFORMATION: Any amino acid
<220> FEATURE:
<221> NAME/KEY: MOD_RES
<222> LOCATION: (42)..(45)
<223> OTHER INFORMATION: Any amino acid
<220> FEATURE:
<221> NAME/KEY: MOD_RES
<222> LOCATION: (47)..(52)
<223> OTHER INFORMATION: Any amino acid and this region may encompass
      5-6 residues
```

<400> SEQUENCE: 23

Cys Xaa Xaa Xaa Xaa Xaa Cys Xaa Xaa Xaa Xaa Cys Cys Xaa
1               5                  10                  15

Xaa Xaa Xaa Xaa Xaa Xaa Xaa Cys Cys Xaa Xaa Xaa Xaa Xaa Cys
            20                  25                  30

Cys Xaa Asp Xaa Xaa His Cys Cys Pro Xaa Xaa Xaa Cys Xaa Xaa
        35                  40                  45

Xaa Xaa Xaa Xaa Cys
    50

<210> SEQ ID NO 24
<211> LENGTH: 10
<212> TYPE: PRT
<213> ORGANISM: Unknown
<220> FEATURE:
<223> OTHER INFORMATION: Description of Unknown: C-terminal PGRN motif
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 24

Cys Cys Xaa Asp Xaa Xaa His Cys Cys Pro
1               5                  10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(33)
<223> OTHER INFORMATION: This region may encompass 2-4 'FLHTRLFV'
      repeating units
<220> FEATURE:
<223> OTHER INFORMATION: See specification as filed for detailed
      description of substitutions and preferred embodiments

<400> SEQUENCE: 26

Met Phe Leu His Thr Arg Leu Phe Val Phe Leu His Thr Arg Leu Phe
1               5                  10                  15

Val Phe Leu His Thr Arg Leu Phe Val Phe Leu His Thr Arg Leu Phe
            20                  25                  30

Val

```
-continued

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly Ser Gly Gly Gly Gly Ser Gly Gly Gly Gly Ser
1               5                   10                  15

<210> SEQ ID NO 28
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Lys Glu Asp Ala Thr Thr Asp Leu Leu Thr
    50                  55                  60

Lys Leu Pro Ala His Thr Val Gly Asp Val Lys Cys Asp Met Glu Val
65                  70                  75                  80

Ser Cys Pro Asp Gly Tyr Thr Cys Cys Arg Leu Gln Ser Gly Ala Trp
                85                  90                  95

Cys Glu Gln Gly Pro His Gln Val Pro Trp Met Glu Lys Ala Pro Ala
            100                 105                 110

His Leu Ser Leu Pro Asp Pro Gln Ala Leu Lys Arg Asp Val Pro Cys
        115                 120                 125

Asp Asn Val Ser Ser Cys Pro Ser Ser Asp Thr Cys Cys Gln Leu Thr
    130                 135                 140

Ser Gly Glu Trp Gly Cys Cys Pro Ile Pro
145                 150
```

METHODS AND COMPOSITIONS FOR MODULATING TNF/TNFR SIGNALING

CROSS-REFERENCE TO RELATED APPLICATIONS

The present application is the U.S. National Stage of PCT/US2012/028458 filed on Mar. 9, 2012, which claims priority to and benefit of U.S. Provisional Patent Application Ser. No. 61/451,190, filed Mar. 10, 2011 the entire contents of which are incorporated herein by reference in their entireties.

GOVERNMENT SUPPORT

This invention was made with government support under AR050620, AR053210, AR040072, GM061710, and AI43542 awarded by the National Institutes of Health. The government has certain rights in the invention.

FIELD OF TECHNOLOGY

The present disclosure relates generally to modulators of TNF/TNFR signaling. In particular, the present technology relates to peptides that antagonize TNF and TNFR signaling methods of using the same in the treatment or prevention of TNF-mediated diseases.

BACKGROUND

Arthritis is a degenerative joint disease currently more than 46,000,000 individuals in the United States. Typical clinical symptoms are pain and stiffness, particularly after prolonged activity. In industrialized societies arthritis is the leading cause of physical disability, increased health care usage, and impaired quality of life. The impact of arthritic conditions is expected to grow as the population both increases and ages in the coming decades.

Despite the prevalence of arthritic diseases, their precise etiologies, pathogenesis, and progression are not well understood. Mounting evidence suggests that inflammatory cytokines and growth factors play a central role in the progression of arthritis. The destruction of the extracellular matrices of articular cartilage and bone in arthritic joints is thought to be mediated by excessive cytokine activities and imbalance between inflammatory cytokines and their natural antagonists. The identification of molecules that modulate signaling by arthritis-related cytokines is therefore highly relevant to the prevention and treatment of arthritis.

Tumor necrosis factor-α (TNF-α) is a key mediator of cytokine-induced inflammation in arthritis. Progranulin (PGRN) is a secreted glycoprotein shown to play an essential role in cartilage formation (See Xu, K, et al. (2007) *J Biol. Chem.* 282(15):11347-11355; WO 2008/094687 A2). PGRN has been shown to bind specifically to TNF receptors 1 and 2 (TNFR1, TNFR2) and to antagonize TNF-α signaling. It has been previously shown that peptides derived from human PGRN are effective in the treatment of arthritis in murine models.

SUMMARY

The present technology comprises methods and compositions for the inhibition of TNFα or TNFR signaling. In one aspect, the technology comprises an isolated peptide comprising SEQ ID NO:4 or variants thereof having at least 90% sequence identity to SEQ ID NO:4.

In some embodiments, the peptide comprises SEQ ID NO:3. In some embodiments, the peptide comprises SEQ ID NO:5. In some embodiments, the peptide comprises SEQ ID NO:6. In some embodiments, the peptide comprises SEQ ID NO:7. In some embodiments, the peptide comprises SEQ ID NO:8.

In some embodiments, the peptide antagonizes signaling by tumor necrosis factor (TNF) or tumor necrosis factor receptor (TNFR) family members. In some embodiments, the TNF is TNFα. In some embodiments, the peptide specifically binds to TNFR1, TNFR2, or both TNFR1 and TNFR2.

In another aspect, the present technology comprises a composition comprising SEQ ID NO:3, SEQ ID NO:4, SEQ ID NO:5, SEQ ID NO:6, SEQ ID NO:7, or SEQ ID NO:8, and a pharmaceutically acceptable carrier. In some embodiments composition further comprises one or more of an anti-inflammatory agent or compound, an anti-cancer agent or compound, and an immunomodulatory agent or compound.

In another aspect, the present technology comprises a method for preventing or treating disease or medical condition caused by or resulting in TNFα, TNFR1, or TNFR2 signaling, comprising administering to a subject in need thereof an effective amount of a pharmaceutical composition comprising SEQ ID NO:3, SEQ ID NO:4, SEQ ID NO:5, SEQ ID NO:6, SEQ ID NO:7, or SEQ ID NO:8.

In some embodiments, the disease comprises an inflammatory disease, an autoimmune disease, an allergic disease, arthritis, or cancer. In some embodiments, the inflammatory disease comprises rheumatoid arthritis, osteoarthritis, ankylosing spondylitis, juvenile idiopathic arthritis, psoriasis, inflammatory bowel diseases, Chrohn's disease, ulcerative colitis, uveitis, inflammatory lung diseases, or chronic obstructive pulmonary disease. In some embodiments, the inflammatory disease is rheumatoid arthritis.

In some embodiments, the autoimmune disease comprises ankylosing spondylitis, psoriasis, inflammatory bowel diseases, Chrohn's disease, ulcerative colitis, uveitis, inflammatory lung diseases, chronic obstructive pulmonary disease, or multiple sclerosis. In some embodiments, the allergic disease comprises local allergic reactions, systemic allergic reactions, respiratory allergic reactions, auditory allergic reactions or gastrointestinal allergic reactions. In some embodiments, the arthritis comprises rheumatoid arthritis, osteoarthritis, ankylosing spondylitis, or juvenile idiopathic arthritis. In some embodiments, the cancer comprises breast cancer, clear cell renal carcinoma, invasive ovarian carcinoma, glioblastoma, adipocytic teratoma, or multiple myeloma.

In some embodiments, the pharmaceutical composition comprises one or more of an anti-inflammatory agent or compound, an anti-cancer agent or compound, and an immunomodulatory agent.

In another aspect, the present technology comprises an isolated peptide comprising PGRN granulin units F (amino acids 123-179 of SEQ ID NO: 1), A (amino acids 281-336 of SEQ ID NO: 1), and C (amino acids 364-417 of SEQ ID NO: 1), or fragments or variants thereof.

In some embodiments, the fragments of PGRN granulin units comprise ½ of granulin unit F (amino acids 123-179 of SEQ ID NO: 1), ½ of granulin A (amino acids 281-336 of SEQ ID NO: 1), and ½ of granulin unit C (amino acids 364-417 of SEQ ID NO: 1).

In some embodiments, the peptide further comprises PGRN linker regions P3 (amino acids 179-205 of SEQ ID NO: 1), P4 (amino acids 261-281 of SEQ ID NO: 1), and P5 (amino acids 336-364 of SEQ ID NO: 1), or fragments or variants thereof.

In some embodiments, the PGRN granulin units and linker regions are in the configuration F-P3-P4-A-P5-C. In some embodiments, the PGRN granulin units and linker regions are in the configuration ½F-P3-P4-½A-P5-½C.

In some embodiments, the peptide comprises an N-terminal methionine. In some embodiments, the peptide comprises an N-terminal ML amino acid sequence. In some embodiments, the peptide comprises an N-terminal MIL amino acid sequence. In some embodiments, the peptide comprises an N-terminal MGIL amino acid sequence. In some embodiments, the peptide comprises an N-terminal GIL amino acid sequence.

In some embodiments, the PGRN is human PGRN. In some embodiments, the peptide antagonizes signaling by tumor necrosis factor (TNF) or tumor necrosis factor receptor (TNFR) family members. In some embodiments, the TNF is TNFα. In some embodiments, the peptide specifically binds to TNFR1, TNFR2, or both TNFR1 and TNFR2.

DETAILED DESCRIPTION

Figure 1:
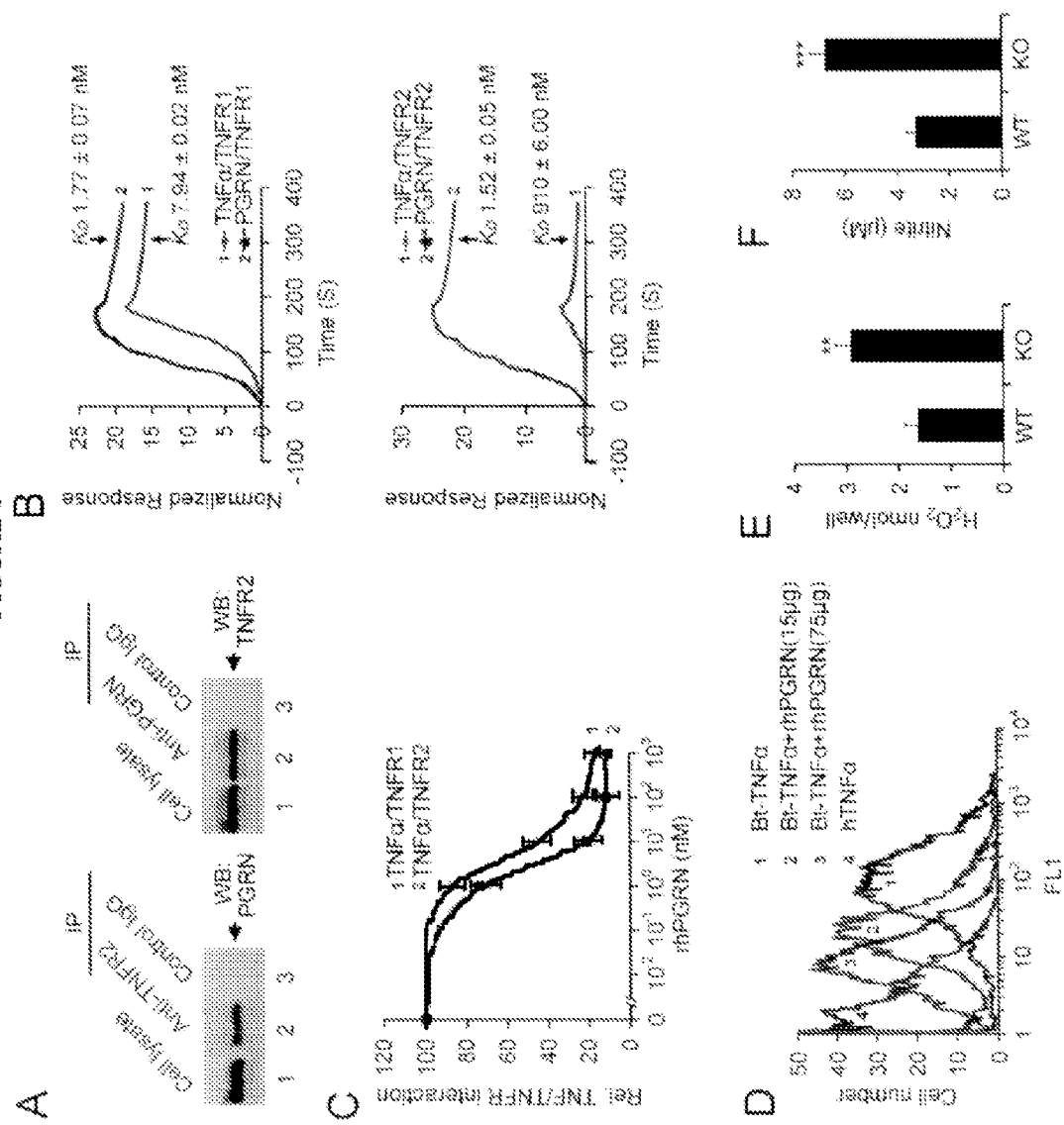
FIG. 1. PGRN directly binds to TNFR and antagonizes TNFα actions. (A) PGRN interacts with TNFR2 in chondrocytes (Co-IP assay). The cell lysates of human chondrocytes were incubated with anti-PGRN, anti-TNFR2 or control IgG antibodies, and bound protein was examined by Western blotting with the corresponding antibodies, as indicated. (B) FastStep™ Kinetic Assay for binding of PGRN and TNFα to TNFR1 and TNFR2. Samples were injected using FastStep™ injection, and dissociation of analyte-ligand complexes was monitored. $K_D$ for each interaction is indicated. (C) PGRN inhibits the binding of TNFα to TNFR1 and TNFR2 (solid phase binding). Microtiter plates coated with TNFα were incubated with TNFR1 or TNFR2 in the presence of various amounts of rhPGRN, and the bound TNFR to TNFα was detected by corresponding antibodies. Values are mean±s.d. (D) Flow cytometry analysis of Raw264.7 cells after staining with 50 ng biotinylated human TNF-α (Bt-TNFα) and different doses of rhPGRN pretreatment. (E) PGRN deletion potentiates TNFα-induced $H_2O_2$ production (neutrophil activation). Wild type (WT) or PGRN-deficient (KO) neutrophils were treated with TNFα, and $H_2O_2$ production was measured. Values are mean±s.d. $P<0.01$; n=4. (F) PGRN deletion potentiates TNFα-induced nitrite production in bone marrow derived macrophages (BMDMs). M-CSF pretreated wild type (WT) or PGRN-deficient (KO) BMDMs were incubated with TNFα, and the supernatants were tested for NO production. Values are mean±s.d. *$P<0.001$; n=4.

The present disclosure describes compositions comprising Atsttrin-α variants and methods for using the same. As demonstrated in the examples below, the Atsttrin-α variants described herein, including, but not limited to, e.g., Atsttrin-α1, Atsttrin-α2, and Atsttrin-α3, are useful in methods comprising the inhibition of TNFα or TNFR signaling, such as in the prevention or treatment of diseases caused by or resulting in TNFα or TNFR signaling (e.g., arthritis and select cancers).

The techniques and procedures described herein are generally performed according to conventional methods in the art and various general references, which are provided throughout this document. See generally, *Current Protocols in Molecular Biology*, Vols. I-III, Ausubel, Ed. (1997); Sambrook, et al., *Molecular Cloning: A Laboratory Manual*, Second Ed. (Cold Spring Harbor Laboratory Press, Cold Spring Harbor, N.Y., 1989); DNA Cloning: A Practical Approach, Vols. I and II, Glover, Ed. (1985); *Oligonucleotide Synthesis*, Gait, Ed. (1984); Nucleic Acid Hybridization, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Generally, the nomenclature used herein and the laboratory procedures in cell culture, molecular genetics, organic chemistry, analytical chemistry and nucleic acid chemistry and hybridization described below are those well known and commonly employed in the art. Standard techniques are used for nucleic acid and peptide synthesis. Standard techniques, or modifications thereof, are used for chemical syntheses and chemical analyses. All references cited herein are incorporated herein by reference in their entireties and for all purposes to the same extent as if each individual publication, patent, or patent application was specifically and individually incorporated by reference in its entirety for all purposes.

DEFINITIONS

The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term that are not clear to persons of ordinary skill in the art, given the context in which it is used, "about" will mean up to plus or minus 10% of the particular term.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding a peptide described herein or amino acid sequence of a peptide described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the complement of a test sequence. The term also includes sequences that have deletions and/or additions, as well as those that have substitutions. As described below, the algorithms can account for gaps and the like. In some embodiments, identity exists over a region that is at least about 25 amino acids or nucleotides in length, or 50-100 amino acids or nucleotides in length.

An "isolated" or "purified" polypeptide or biologically-active portion thereof is substantially free of cellular material or other contaminating polypeptides from the cell or tissue source from which the polypeptide is derived, or substantially free from chemical precursors or other chemicals when chemically synthesized. For example, an isolated peptide would be substantially free of materials that would interfere with diagnostic methods used to further purify the peptide or to determine the amino acid sequence of the peptide. Such interfering materials may include enzymes, hormones and other proteinaceous and nonproteinaceous solutes.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "amino acid substitution" refers to the replacement of a naturally occurring or wild type amino acid at a given position within a peptide or polypeptide with another residue. Conservative substitutions are those in which substitute amino acids share the same or similar chemical properties as the naturally occurring amino acid, and/or do not alter the biological properties of the peptide or polypeptide as a whole. Non-conservative substitutions are those in which the substitute amino acid does not share the same or similar chemical properties as the naturally occurring amino acid, and/or those which alter the biological properties of the peptide or polypeptide as a whole. For example, one or more amino acid residues within a peptide sequence can be substituted for another amino acid of a similar polarity which acts as a functional equivalent, resulting in a silent alteration (a conservative amino acid substitution). Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. The negatively charged (acidic) amino acids include aspartic acid and glutamic acid. Methods for designing amino acid substitutions are well known in the art, as are methods for the introduction of amino acid substitutions into a protein or peptide.

As used herein, "progranulin," "PGRN," and "human PGRN" refer to the amino acid sequence set forth in Genbank Accession Nos. NP 002078.1, GI 4504151 and SEQ ID NO:1, and variants and homologues thereof. Mammalian homologues of human PGRN include but are not limited to *Rattus norvegicus* (rat; Genbank accession AAA16903.1, CAA44198.1), *Mus musculus* (mouse; Genbank accession P28798.2, BAE35389.1, NP_032201.2), *Pongo abelii* (Sumatran orangutan; Genbank accession NP_001126689.1), *Macaca fascicularis* (crab-eating macaque; Genbank accession BAE01796.1), *Equus caballus* (horse; Genbank accession XP_001489791.1), *Bos taurus* (cattle; Genbank accession NP_001070482.1), *Oryctolagus cuniculus* (rabbit; Genbank accession XP_002719228.1), *Sus scrofa* (pig; Genbank accession NP_001038043.1), *Pan troglodytes* (chimpanzee; Genbank accession XP_511549.2), and *Monodelphis domestica* (opossum; Genbank accession XP_001374870.1) homologues.

As discussed herein, PGRN is a 593-amino-acid secreted glycoprotein which acts as an autocrine growth factor. The PGRN protein contains seven and a half repeats of a cysteine-rich "granulin" motif of the general structure $CX_{5-6}CX_5CCX_8CCX_6CCXDX_2HCCPX_4CX_{5-6}C$, interspersed with alternating linker regions. The granulin domains are designated, in order from N-terminus to C-terminus, P-G-F-B-A-C-D-E, where A-G are full motifs and P is a half motif. The linker regions are designated P1, P2, P3, P4, P5, P6, and P7. Schematic diagrams of the structure of human PGRN are set forth in the accompanying figures. The amino acid sequence of human PGRN is set forth in SEQ ID NO:1.

The terms "Atsttrin-α" and "Antagonist of TNF/TNFR Signaling via Targeting TNF Receptors-α" are used interchangeably to refer to the amino acid sequence set forth in SEQ ID NO:2. Atsttrin-α is a peptide derived from human PGRN, the amino acid sequence of which is set forth in SEQ ID NO:1. Atsttrin-α comprises one half of each of PGRN granulin units F, A, and C, and linker regions P3, P4, and P5, in the overall configuration ½F-P3-P4-½A-P5-½C.

As used herein, "Atsttrin-α variants" refers to peptides related to Atsttrin-α and containing one or more amino acid additions, deletions, or substitutions, wherein the peptides have the capacity to inhibit TNFα or TNFR signaling in vitro and in vivo. In some embodiments, the Atsttrin-α variant comprises the PGRN subunit structure ⅔F—P3-P4-⅔A-P5-⅔C. In some embodiments the Atsttrin-α variant is Atsttrin-α1, the amino acid sequence of which is set forth in SEQ ID NO:3. In some embodiments the Atsttrin-α variant is Atsttrin-α2, the amino acid sequence of which is set forth in SEQ ID NO:4. In some embodiments the Atsttrin-α variant is Atsttrin-α3, the amino acid sequence of which is set forth in SEQ ID NO:5. In some embodiments the Atsttrin-α variant is Atsttrin-α4, the amino acid sequence of which is set forth in SEQ ID NO:6. In some embodiments the Atsttrin-α variant is Atsttrin-α5, the amino acid sequence of which is set forth in SEQ ID NO:7. In some embodiments the Atsttrin-α variant is Atsttrin-α6, the amino acid sequence of which is set forth in SEQ ID NO:8. In some embodiments the Atsttrin-α variant is Atsttrin-α7, the amino acid sequence of which is set forth in SEQ ID NO:9. In some embodiments the Atsttrin-α variant is Atsttrin-α8, the amino acid sequence of which is set forth in SEQ ID NO:10. In some embodiments the Atsttrin-α variant is Atsttrin-α9, the amino acid sequence of which is set forth in SEQ ID NO:11.

TABLE 1

Amino Acid sequences of PGRN, Atsttrin-α, and Atsttrin-α Variants

SEQ ID NO: 1
Human Progranulin (PGRN)
MWTLVSWVALTAGLVAGTRCPDGQFCPVACCLDPGGASYSCCRPLLDKWPTTLSRHL
GGPCQVDAHCSAGHSCIFTVSGTSSCCPFPEAVACGDGHHCCPRGFHCSADGRSCFQRS
GNNSVGAIQCPDSQFECPDFSTCCVMVDGSWGCCPMPQASCCEDRVHCCPHGAFCDLV TABLE 1 -continued Amino Acid sequences of PGRN, Atsttrin-α, and Atsttrin-α Variants

```
HTRCITPTGTHPLAKKLPAQRTNRAVALSSSVMCPDARSRCPDGSTCCELPSGKYGCCP
MPNATCCSDHLHCCPQDTVCDLIQSKCLSKENATTDLLTKLPAHTVGDVKCDMEVSCP
DGYTCCRLQSGAWGCCPFTQAVCCEDHIHCCPAGFTCDTQKGTCEQGPHQVPWMEKA
PAHLSLPDPQALKRDVPCDNVSSCPSSDTCCQLTSGEWGCCPIPEAVCCSDHQHCCPQG
YTCVAEGQCQRGSEIVAGLEKMPARRASLSHPRDIGCDQHTSCPVGQTCCPSLGGSWA
CCQLPHAVCCEDRQHCCPAGYTCNVKARSCEKEVVSAQPATFLARSPHVGVKDVECG
EGHFCHDNQTCCRDNRQGWACCPYRQGVCCADRRHCCPAGFRCAARGTKCLRREAPR
WDAPLRDPALRQLL
```

SEQ ID NO: 2

Atsttrin-α
158 amino acids
```
PQASCCEDRVHCCPHGAFCDLVHTRCITPTGTHPLAKKLPAQRTNRAVALSSSASSKEN
ATTDLLTKLPAHTVGDVKCDMEVSCPDGYTCCRLQSGAWPWCEQGPHQVPWMEKAP
AHLSLPDPQALKRDVPCDNVSSCPSSDTCCQLTSGEWGCCPIP
```

SEQ ID NO: 3

Atsttrin-α1
157 amino acids
```
GILPQASCCEDRVHCCPHGAFCDLVHTRCITPTGTHPLAKKLPAQRTNRAVALSSSSKEN
ATTDLLTKLPAHTVGDVKCDMEVSCPDGYTCCRLQSGAWCEQGPHQVPWMEKAPAH
LSLPDPQALKRDVPCDNVSSCPSSDTCCQLTSGEWGCCPIP
```

SEQ ID NO: 4

Atsttrin-α2
154 amino acids
```
PQASCCEDRVHCCPHGAFCDLVHTRCITPTGTHPLAKKLPAQRTNRAVALSSSSKENAT
TDLLTKLPAHTVGDVKCDMEVSCPDGYTCCRLQSGAWCEQGPHQVPWMEKAPAHLSL
PDPQALKRDVPCDNVSSCPSSDTCCQLTSGEWGCCPIP
```

SEQ ID NO: 5

Atsttrin-α3
155 amino acids
```
MPQASCCEDRVHCCPHGAFCDLVHTRCITPTGTHPLAKKLPAQRTNRAVALSSSSKENA
TTDLLTKLPAHTVGDVKCDMEVSCPDGYTCCRLQSGAWCEQGPHQVPWMEKAPAHLS
LPDPQALKRDVPCDNVSSCPSSDTCCQLTSGEWGCCPIP
```

SEQ ID NO: 6

Atsttrin-α4
156 amino acids
```
MLPQASCCEDRVHCCPHGAFCDLVHTRCITPTGTHPLAKKLPAQRTNRAVALSSSSKEN
ATTDLLTKLPAHTVGDVKCDMEVSCPDGYTCCRLQSGAWCEQGPHQVPWMEKAPAH
LSLPDPQALKRDVPCDNVSSCPSSDTCCQLTSGEWGCCPIP
```

SEQ ID NO: 7

Atsttrin-α5
157 amino acids
```
MILPQASCCEDRVHCCPHGAFCDLVHTRCITPTGTHPLAKKLPAQRTNRAVALSSSSKE
NATTDLLTKLPAHTVGDVKCDMEVSCPDGYTCCRLQSGAWCEQGPHQVPWMEKAPA
HLSLPDPQALKRDVPCDNVSSCPSSDTCCQLTSGEWGCCPIP
```

SEQ ID NO: 8

Atsttrin-α6
158 amino acids
```
MGILPQASCCEDRVHCCPHGAFCDLVHTRCITPTGTHPLAKKLPAQRTNRAVALSSSSK
ENATTDLLTKLPAHTVGDVKCDMEVSCPDGYTCCRLQSGAWCEQGPHQVPWMEKAP
AHLSLPDPQALKRDVPCDNVSSCPSSDTCCQLTSGEWGCCPIP
```

SEQ ID NO: 9

Atsttrin-α7
219 amino acids
```
IQCPDSQFECPDFSTCCVMVDGSWGCCPMPQASCCEDRVHCCPHGAFCDLVHTRCITPT
GTHPSKENATTDLLTKLPAHTVGDVKCDMEVSCPDGYTCCRLQSGAWGCCPFTQAVC
CEDHIHCCPAGFTCDTQKGTCEQGPHQVPWMEKAPAHLSLPDPQALKRDVPCDNVSSC
PSSDTCCQLTSGEWGCCPIPEAVCCSDHQHCCPQGYTCVAEGQCQ
```

SEQ ID NO: 10

Atsttrin-α8
222 amino acids
```
GILIQCPDSQFECPDFSTCCVMVDGSWGCCPMPQASCCEDRVHCCPHGAFCDLVHTRCI
TPTGTHPSKENATTDLLTKLPAHTVGDVKCDMEVSCPDGYTCCRLQSGAWGCCPFTQA
VCCEDHIHCCPAGFTCDTQKGTCEQGPHQVPWMEKAPAHLSLPDPQALKRDVPCDNVS
SCPSSDTCCQLTSGEWGCCPIPEAVCCSDHQHCCPQGYTCVAEGQCQ
```

TABLE 1 -continued

Amino Acid sequences of PGRN, Atsttrin-α, and Atsttrin-α Variants

SEQ ID NO: 11
Atsttrin-α9
223 amino acids
MGILIQCPDSQFECPDFSTCCVMVDGSWGCCPMPQASCCEDRVHCCPHGAFCDLVHTR
CITPTGTHPSKENATTDLLTKLPAHTVGDVKCDMEVSCPDGYTCCRLQSGAWGCCPFT
QAVCCEDHIHCCPAGFTCDTQKGTCEQGPHQVPWMEKAPAHLSLPDPQALKRDVPCD
NVSSCPSSDTCCQLTSGEWGCCPIPEAVCCSDHQHCCPQGYTCVAEGQCQ As used herein, "Atsttrin-α variants" also refers to Atsttrin-α derivatives bearing one or more amino acid substitutions, additions, deletions, or other protein modifications known in the art. Examples of such modifications include but are not limited to phosphorylation, glycosylation, myristoylation, palmitoylation, isoprenylation, prenylation, farnesylation, geranylgeranylation, glypiation, lipoylation, addition of a flavin moiety (FMN or FAD), heme attachment via thioether bonds, phosphopantetheinylation, retinylidene Schiff base formation, diphthamide formation, ethanolamine phosphoglycerol attachment, hypusine formation, acylation, acetylation, formylation, alkylation, methylation, amide bond formation, amidation at C-terminus, arginylation, polyglutamylation, polyglycylation, gamma-carboxylation, polysialylation, ADP-ribosylation, hydroxylation, iodination, oxidation, phosphate ester (O-linked) or phosphoramidate (N-linked) formation, adenylylation, pyroglutamate formation, S-glutathionylation, S-nitrosylation, sulfation, selenoylation, glycation, pegylation, SUMOylation, ubiquitination, Neddylation, deamidation, eliminylation, and carbamylation.

The term "inflammatory mediators" refers to mediators which enhance, initiate or facilitate an inflammatory reaction or an inflammatory response. Examples of inflammatory mediators include but are not limited to cytokines (e.g., TNFα, IL3, IL4, IL5, IL13, GM-CSF), chemokines (e.g., MDC, CCL19, CCL20, CCL21, MIP-1α), prostaglandins (e.g., PGD2), leukotrienes (e.g., LTB4, LTC4, LTD4), metalloproteases, chymase, tryptase, and growth factors (e.g., VEGF).

The term "disease characterized by inflammation," or "inflammatory disease" refers to a disease or medical condition caused by, resulting in, or otherwise characterized by inflammation. Examples of inflammatory diseases include but are not limited to, e.g., rheumatoid arthritis, osteoarthritis, ankylosing spondylitis, juvenile idiopathic arthritis, psoriasis, inflammatory bowel diseases, Chrohn's disease, ulcerative colitis, uveitis, inflammatory lung diseases, and chronic obstructive pulmonary disease. As used herein, the term encompasses both acute and chronic inflammatory diseases and conditions.

As used herein, "allergic disease" refers to a disease or medical condition characterized by a hypersensitivity disorder of the immune system. Such disease may be characterized by high levels of mast cell and basophil activation, and high levels of IgE production. As used herein, the term encompasses allergic reactions in any tissue of the body, including but not limited to, e.g., respiratory, auditory, and gastrointestinal tissues. As used herein, the term encompasses local and systemic allergic reactions (e.g., anaphylaxis).

As used herein, "autoimmune disease" refers to a disease or medical condition characterized by inappropriate recognition of self-antigens by the immune system, including cells, tissues, or molecules normally present in the body. Examples of autoimmune diseases include but are not limited to, e.g., ankylosing spondylitis, psoriasis, inflammatory bowel diseases, Chrohn's disease, ulcerative colitis, uveitis, inflammatory lung diseases, chronic obstructive pulmonary disease, and multiple sclerosis.

As used herein, the terms "treating" or "treatment" or "alleviation" refers to both therapeutic treatment and prophylactic or preventative measures, wherein the object is to eliminate the disease or slow disease progression. As used herein, the term encompasses both total and less than total disease elimination, wherein prevent or slow disease wherein some biologically or medically relevant result is achieved.

As used herein, "prevention" of a disorder refers to preventing or delaying the onset of the condition, or preventing the occurrence, number, or severity of symptoms associated with the condition compared to untreated controls. The term "prophylaxis" is encompassed by the term "prevention," and refers to a measure or procedure the purpose of which is to prevent, rather than to treat or cure a condition.

General

In the progress of arthritis, synovium, cartilage, and bone are all sites of increased production of growth factors, cytokines, and inflammatory mediators that are believed to contribute to pathogenesis. Although both bone and synovium have important roles in the pathogenesis of arthritis, most efforts at developing disease-modifying treatments have focused on the molecular events within cartilage. Arthritic chondrocytes undergo a series of complex changes, including proliferation, catabolic alteration, and cell death. The regulation of these phenotypic changes at different stages of disease is under intensive study, with focus on the biomechanical and biochemical signals that regulate each of these chondrocyte responses. Chondrocytes themselves are protagonists in this regulatory cascade, producing cytokines, proteases, and inflammatory mediators that promote the deterioration of articular cartilage. Pathogenic molecules produced by arthritic chondrocytes include tumor necrosis factor (TNF), interleukin-1 (IL-1), IL-6, IL-8, matrix metalloproteinases (MMPs), ADAMTSs, nitric oxide, prostaglandins, and leukotrienes. There is also evidence that arthritic chondrocytes exhibit increased anabolic activity, including increased release of growth factors and synthesis of type II collagen, proteoglycan, and other extracellular matrix proteins, as well as the expression of genes associated with the chondroprogenitor hypertrophic phenotype.

A great deal of research in rheumatology over the past two decades has focused on identifying cytokines and mediators responsible for the inflammatory and degenerative processes in rheumatoid arthritis (RA), with the aim of developing specific antagonists of therapeutic value. Among all factors, TNF-α has received the greatest attention because of its position at the apex of the pro-inflammatory cytokine cascade, and its dominance in the pathogenesis of RA. Many lines of evidence implicate TNF-α in RA progression, including that 1) TNF-α is expressed at high levels in inflamed synovium and cartilage from RA patients, 2) anti-TNF-α inhibits the production of other pro-inflammatory cytokines including IL-1, and 3) TNF-α can induce joint inflammation, trigger cartilage destruction by inducing metalloproteinase, and stimulate osteoclastogenesis and bone resorption. Anti-TNF therapies for RA have shown remarkable results by decreasing inflammation, improving patient function and vitality, and attenuating cartilage and bone erosions. Anti-TNF therapies that target the TNF ligand include etanercept (Enbrel®, a soluble TNFR2-lgG1 fusion protein), infliximab (Remicade®, a chimeric monoclonal antibody against TNF-α), and adalimumab (a monoclonal antibody against TNF-α).

Progranulin (PGRN), also known as Granulin/epithelin precursor (GEP), PC-cell-derived growth factor (PCDGF), acrogranin, proepithelin (PEPI), and GP80, was first purified as a growth factor from conditioned tissue culture media. PGRN is a 593-aminoacid long-secreted glycoprotein with an apparent molecular weight of 80 kDa, which acts as an autocrine growth factor. The PGRN protein contains seven and a half repeats of a cysteine-rich "granulin" motif of the general structure $CX_{5-6}CX_5CCX_8CCX_6CCXDX_2HCCPX_4CX_{5-6}C$, interspersed with alternating linker regions. The granulin domains are designated, in order from N-terminus to C-terminus, P-G-F-B-A-C-D-E, where A-G are full motifs and P is a half motif. The linker regions are designated P1, P2, P3, P4, P5, P6, and P7. Schematic diagrams of the structure of human PGRN are set forth in the accompanying figures. The amino acid sequence of human PGRN is set forth in SEQ ID NO:1. The C-terminal region of PGRN contains the conserved sequence $CCXDX_2HCCP$, which is thought to bind metals and regulate PGRN function. PGRN undergoes proteolytic processing with the liberation of small, 6-kDa repeat units known as granulins (or epithelins), which retain biological activity peptides are active in cell growth assays and may be related to inflammation.

PGRN is abundantly expressed in rapidly cycling epithelial cells, immune cells, and neurons. High levels of PGRN expression are also found in several human cancers and contribute to tumorigenesis in diverse cancers, including breast cancer, clear cell renal carcinoma, invasive ovarian carcinoma, glioblastoma, adipocytic teratoma, and multiple myeloma.

The role of PGRN in the regulation of cellular proliferation has been well characterized using mouse embryo fibroblasts derived from mice with a targeted deletion of the insulin-like growth factor receptor (IGF-IR) gene (R-cells). These cells are unable to proliferate in response to IGF-1 and other growth factors (EGF and PDGF) necessary for progression through the cell cycle. PGRN is the only known growth factor able to bypass the requirement for the IGF-IR, thus promoting cell growth of R-cells. Increasing evidence has also implicated PGRN in the regulation of differentiation, development, wound healing, and tissue repair.

The Tumor Necrosis Factor (TNF) family of cytokines plays an essential role in multiple biological functions including inflammation, organogenesis, host defense, autoimmunity, and apoptosis. The action of these potent biological mediators is achieved through a receptor-ligand interaction, leading to intracellular signaling and a change in cellular phenotype. Upon binding of trimeric TNF ligands, TNF receptors (TNFR) bind TNF receptor-associated factor (TRAF) adaptor proteins, which transduce the TNF signal intracellularly. TNFR family members known to interact with TRAF proteins include TNFR2, TNFR1, TrkA, NGFR, CD 40, CD 30, OX-40, DR5, DR3, DR4, and RANK.

Both TNF receptors (TNFR1 and TNFR2) are ubiquitously expressed in cells and interact with their cognate ligand: TNFα. It is widely accepted that TNFα serves important functions in pathophysiology, being a factor that interferes strongly with the cell growth, differentiation and death. TNF appears not only to orchestrate acute responses to infection and immunological injury but also to act as a balancing factor required for the re-establishment of physiological homeostasis and regulation. TNFα effects skeletal development, and is involved in the pathogenesis of imflammatory, allergic, and autoimmune diseases.

It has been previously shown that PGRN, and in particular human PGRN, binds directly to TNFR1 and TNFR2, and antagonizes TNFα signaling in vitro and in vivo. See, Liu, et al., WO/2010/120374. It has further been shown that recombinant human PGRN (rhPGRN) is therapeutically effective in treating collagen-induced arthritis (CIA) in murine subjects. Administration of rhPGRN to CIA mice reduced inflammation, leukocyte infiltration, and loss of cartilage matrix compared to control samples. In addition, prophylactic administration of rhPGRN to the (i.e. mice prior to the administration collagen) also prevented the onset of CIA-related symptoms. These data demonstrate that PGRN is therapeutically effective in the prevention and treatment of CIA, and TNFα-mediated arthritis in general.

It has further been shown that a peptide derived from human PGRN retains the capacity to bind TNFR1/TNFR2 and antagonize TNFα signaling. The peptide, termed Atsttrin-α (Antagonist of TNF/TNFR Signaling via Targeting TNF Receptors-α) comprises amino acids 153-205, 262-304, and 334-392 of human PGRN, shown in FIG. 1 (SEQ. ID NO.: 1). Atsttrin-α comprises two non-native amino acids at the junctures of PGRN amino acids 205/262 and 304/334, which are retained from cloning intermediates (SEQ ID NO:2, non-native amino acids highlighted in underline text). Structurally, Atsttrin-α comprises one-half of each of granulin units F, A, and C, and linker regions P3, P4, and P5, in the overall configuration ½F-P3-P4-½A-P5-½C.

The present technology comprises variants of Atsttrin-α, termed Atsttrin-α1, Atsttrin-α2, and Atsttrin-α3. The sequence of Atsttrin-α1 is given by SEQ ID NO:3. Atsttrin-α1 differs from Atsttrin-α in that it does not contain the non-native amino acids retained from cloning intermediates. The sequence of Atsttrin-α2 is given by SEQ ID NO:4. Atsttrin-α2 differs from Atsttrin-α1 in that is has an N-terminal methionine addition. The sequence of Atsttrin-α3 is given by SEQ ID NO:5. Atsttrin-α3 differs from Atsttrin-α1 in that it has an N-terminal MGIL addition. As demonstrated by the examples below, the Atsttrin-α variants described herein are useful in methods for the inhibition of TNFα or TNFR signaling, such as in the prevention or treatment of conditions caused by or resulting in TNFα or TNFR signaling. Such conditions include but are limited to, e.g., arthritis, autoimmune diseases, allergic diseases, and cancer. The Atsttrin-α variants described herein are useful in the treatment or prevention of both acute and chronic inflammatory conditions.

Compositions of the Present Technology

In one aspect, the present technology comprises Atsttrin-α peptide variants and compositions comprising the same. As described in the examples below, the Atsttrin-α variants described herein possess the same biological function as Atsttrin-α. As described in the examples below, the Atsttrin-α variants described herein bind specifically to TNFR1 and TNFR2, and antagonize TNFR1, TNFR2, and TNFα signaling in vitro and in vivo. As described in the examples below, the Atsttrin-α variants described herein are useful in methods comprising inhibition of TNFα, TNFR1, or TNFR2 signaling, such as in the prevention or treatment of conditions caused by or resulting in TNFα, TNFR1, or TNFR2 signaling.

In one aspect, the present technology comprises a peptide fragment or derivative of progranulin (PGRN), wherein the fragment or derivative comprises (a) one or more granulin units of PGRN or fragments or variants thereof and (b) one or more linker units of PGRN, and wherein the peptide antagonizes TNF family member signaling. In some embodiments, the PGRN is human PGRN.

In some embodiments, the one or more granulin units of PGRN or fragments or variants thereof are selected from the group consisting of: a fragment of F (amino acids 123-179 of SEQ ID NO:1); a fragment of A (amino acids 281-336 of SEQ ID NO:1); and a fragment of C (amino acids 364-417 of SEQ ID NO:1).

In some embodiments, the one or more granulin units of PGRN or fragments or variants thereof are selected from the group consisting of: F (amino acids 123-179 of SEQ ID NO:1); A (amino acids 281-336 of SEQ ID NO:1); and C (amino acids 364-417 of SEQ ID NO:1).

In some embodiments, the granulin units of PGRN comprise granulin units F (amino acids 123-179 of SEQ ID NO:1), A (amino acids 281-336 of SEQ ID NO:1), and C (amino acids 364-417 of SEQ ID NO:1).

In some embodiments, the one or more granulin units of PGRN or fragments or variants thereof are selected from the group consisting of: (a) at least ½F (amino acids 135-179 of SEQ ID NO:1); (b) at least ½A (amino acids 281-306 of SEQ ID NO:1); and (c) at least ½C (amino acids 364-392 of SEQ ID NO:1).

In some embodiments, the one or more granulin units of PGRN or fragments or variants thereof are selected from the group consisting of: (a) amino acids 135-179 of SEQ ID NO:1; (b) amino acids 281-306 of SEQ ID NO:1; and (c) amino acids 364-392 of SEQ ID NO:1.

In some embodiments, the granulin units of PGRN: (a) amino acids 135-179 of SEQ ID NO:1; (b) amino acids 281-306 of SEQ ID NO:1; and (c) amino acids 364-392 of SEQ ID NO:1.

In some embodiments, the one or more linker units are selected from the group consisting of: (a) a fragment of P3 (amino acids 179-205 of SEQ ID NO:1); (b) a fragment of P4 (amino acids 261-281 of SEQ ID NO:1); and (c) a fragment of P5 (amino acids 336-364 of SEQ ID NO:1).

In some embodiments, the peptide fragment or derivative comprises (a) F (amino acids 123-179 of SEQ ID NO:1) and P3 (amino acids 179-205 of SEQ ID NO:1) of PGRN; (b) A (amino acids 281-336 of SEQ ID NO:1) and P4 (amino acids 261-281 of SEQ ID NO:1) of PGRN; or (c) C (amino acids 364-417 of SEQ ID NO:1) and P5 (amino acids 336-364 of SEQ ID NO:1) of PGRN.

In some embodiments, the peptide fragment or derivative comprises (a) ½F (amino acids 135-179 of SEQ ID NO:1) and P3 (amino acids 179-205 of SEQ ID NO:1) of PGRN; (b) ½A (amino acids 281-306 of SEQ ID NO:1) and P4 (amino acids 261-281 of SEQ ID NO:1) of PGRN; or (c) ½C (amino acids 364-392 of SEQ ID NO:1) and P5 (amino acids 336-364 of SEQ ID NO:1) of PGRN.

In some embodiments, the fragment or derivative comprises (a) amino acids 123-204 of SEQ ID NO:1; (b) amino acids 262-336 of SEQ ID NO:1; or (c) amino acids 337-417 of SEQ ID NO:1.

In some embodiments, the peptide fragment or derivative comprises (a) F (amino acids 123-179 of SEQ ID NO:1) and P3 (amino acids 179-205 of SEQ ID NO:1) of PGRN; (b) A (amino acids 281-336 of SEQ ID NO:1) and P4 (amino acids 261-281 of SEQ ID NO:1) of PGRN; and (c) C (amino acids 364-417 of SEQ ID NO:1) and P5 (amino acids 336-364 of SEQ ID NO:1) of PGRN.

In some embodiments, the peptide fragment or derivative comprises (a) amino acids 123-204 of SEQ ID NO: 1; (b) amino acids 262-336 of SEQ ID NO:1; and (c) amino acids 337-417 of SEQ ID NO:1.

In some embodiments, the peptide comprises SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or a variant thereof having about 60%, about 65%, about 70%, about 75%, about 80%, about 85%, about 90%, about 91%, about 92%, about 93%, about 94%, about 95%, about 96%, about 97%, about 98%, about 99%, or higher identity to SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In some embodiments, the peptide consists of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, or a variant thereof having about 60%, about 65%, about 70%, about 75%, about 80%, about 85%, about 90%, about 91%, about 92%, about 93%, about 94%, about 95%, about 96%, about 97%, about 98%, about 99%, or higher identity to SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In another aspect, the present technology comprises a pharmaceutical composition comprising an isolated Atsttrin-α variant and a pharmaceutically acceptable carrier, vehicle, or diluent. In some embodiments, the composition further comprises one or more of an anti-inflammatory agent or compound, an anti-cancer agent or compound, and an immunomodulatory agent.

In another aspect, the present technology comprises an isolated peptide consisting of: (a) one, two, or three granulin units of progranulin (PGRN) protein or fragments or variants thereof; and (b) at least one linker unit, wherein the peptide antagonizes TNF family member signaling.

In another aspect, the present technology comprises an isolated peptide comprising one or more granulin units of progranulin (PGRN) or fragments or variants thereof and one or more linker units, wherein at least one of the granulin units is an F, A, or C granulin unit. In some embodiments, the granulin unit fragment comprises ½ of a granulin unit. In some embodiments, the granulin unit fragment comprises ⅔ of a granulin unit.

As used herein, a granulin unit fragment refers to a sequence of contiguous amino acids derived from the granulin unit, wherein the sequence length is given by $A=xL\pm5$, where A is the number of amino acids comprising the granulin unit fragment, x is a fractional value, L is the full-length of the granulin unit, and ±5 encompasses ±0, ±1, ±2, ±3, ±4, and ±5. Where the value of xL is not an integer, the value is rounded to the next nearest integer. Granulin unit fragments may comprise any span of contiguous amino acids within the full-length granulin unit.

Accordingly, a ½ fragment of a granulin unit 100 amino acids in length comprises peptides 45, 46, 47, 48, 49, 50, 51, 52, 53, 54, and 55 contiguous amino acids in length spanning any portion of the full-length granulin unit. Accordingly, a ⅔ fragment of a granulin unit 100 amino acids in length comprises peptides 62, 63, 64, 65, 66, 67, 68, 69, 70, 71, and 72 contiguous amino acids in length spanning any portion of the full-length granulin unit.

Accordingly, a ½ fragment of granulin unit F (amino acids 123-179 of SEQ ID NO:1) comprises peptides 24, 25, 26, 27, 28, 29, 30, 31, 32, 33, or 34 contiguous amino acids in length spanning any portion of granulin unit F. Accordingly, a ⅔ fragment of granulin unit F (amino acids 123-179 of SEQ ID NO:1) comprises peptides 33, 34, 35, 36, 37, 38, 39, 40, 41, 42, or 43 contiguous amino acids in length spanning any portion of granulin unit F.

Accordingly, a ½ fragment of granulin unit A (amino acids 281-336 of SEQ ID NO:1) comprises peptides 23, 24, 25, 26, 27, 28, 29, 30, 31, 32, or 33 contiguous amino acids in length spanning any portion of granulin unit A. Accordingly, a ⅔ fragment of granulin unit A (amino acids 281-336 of SEQ ID NO:1) comprises peptides 32, 33, 34, 35, 36, 37, 38, 39, 40, 41, or 42 contiguous amino acids in length spanning any portion of granulin unit A.

Accordingly, a ½ fragment of granulin unit C (amino acids 364-417 of SEQ ID NO:1) comprises peptides 22, 23, 24, 25, 26, 27, 28, 29, 30, 31, or 32 contiguous amino acids in length spanning any portion of granulin unit C. Accordingly, a ⅔ fragment of granulin unit C (amino acids 364-417 of SEQ ID NO:1) comprises peptides 31, 32, 33, 34, 35, 36, 37, 38, 39, 40, or 41 contiguous amino acids in length spanning any portion of granulin unit C.

In another aspect, the present technology comprises fragments of Atsttrin-α and Atsttrin-α variants. As used herein, a fragment of Atsttrin-α or Atsttrin-α variant comprises any portion of the Atsttrin-α or Atsttrin-α variant amino acid sequence of that retains the capacity to bind to TNFR1 and/or TNFR2 and inhibit signaling by TNFα, TNFR1, or TNFR2. Fragments of Atsttrin-α or Atsttrin-α variants may comprise contiguous Atsttrin-α or Atsttrin-α sequence, such as where one or more amino acids are deleted from the N- or C-terminus, or may comprise non-contiguous Atsttrin-α or Atsttrin-α sequence, such as where one or more amino acids are deleted internally.

In some embodiments, the Atsttrin-α variants comprise a variant of SEQ ID NO:2 having one or more amino acid substitutions. In some embodiments, the Atsttrin-α variants comprise a variant of SEQ ID NO:2 having an N-terminal methionine. In some embodiments, the Atsttrin-α variants comprise a variant of SEQ ID NO:2 having and N-terminal MGIL addition. In some embodiments, the Atsttrin-α variants comprise the variants of SEQ ID NO:2 set forth in SEQ ID NO:3, SEQ ID NO:4, and SEQ ID NO:5.

In some embodiments, the Atsttrin-α variants comprise a variant of SEQ ID NO:2 having one or more amino acid additions, deletions, or modifications, wherein the variant retains the capacity to antagonize TNF and TNFR signaling. In some embodiments the Atsttrin-α variant is a variant of SEQ ID NO:2 having multiple amino acid substitutions, additions, deletions, or modifications. In some embodiments, the variant of SEQ ID NO:2 comprises a PGRN-derived peptide with the structure F-P3-P4-A-P5-C. In some embodiments, the variant of SEQ ID NO:2 comprises a PGRN-derived peptide with the structure ⅔F-P3-P4-⅔A-P5-⅔C.

In one aspect, present technology comprises amino acid sequences substantially identical to Atsttrin-α and the Atsttrin-α variants disclosed herein. In some embodiments, substantially identical amino acid sequences have about 60%, about 65%, about 70%, about 75%, about 80%, about 85%, about 90%, about 91%, about 92%, about 93%, about 94%, about 95%, about 96%, about 97%, about 98%, about 99%, or higher identity to SEQ ID NO:2. In some embodiments, the substantially identical amino acid sequences comprise SEQ ID NO:3, SEQ ID NO:4, or SEQ ID NO:5. In some embodiments, the substantially identical peptides have the granulin subunit structure F-P3-P4-A-P5-C, ⅔F-P3-P4-⅔A-P5-⅔C, or ½F-P3-P4-½A-P5-½C.

Peptides of the present technology may be produced using methods known in the art, including but not limited to, e.g., the expression of recombinant molecules in cell-based or cell-free systems, or chemical synthesis. One of skill in the art will understand that synthesis by any means compatible with the intended use of the peptides is suitable for the practice of the present technology. For example, where the intended use is administration to a human subject, synthesis of the peptides will be done using methods approved for such. Where the intended use of the peptides is an in vitro use, the methods may be adjusted accordingly. Likewise, one of skill in the art will understand that the purity of the peptides and the nature and level of permissible contaminants will vary according to the intended use.

In one aspect, the present technology encompasses polynucleotide sequences encoding the amino acid sequences of SEQ ID NO:3, SEQ ID NO:4, and SEQ ID NO:5, and the corresponding complementary sequences. One of skill in the art will understand that owing to the degeneracy of the genetic code, this encompasses a wide variety of sequences. DNA sequences of the present technology may be prepared using standard methods known in the art, including but not limited to polymerase chain reaction (PCR) amplification, cell-based DNA replication, and cell-free DNA replication.

Atsttrin-α variants may be prepared in which one or more amino acids are added, deleted, substituted, or modified using methods well-known in the art. For example, amino acid substitutions, additions, or deletions may be made by altering the DNA sequence encoding the Atsttrin-α variant accordingly. Substitutions may be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping).

Amino acid substitutions may be designed to retain or impart certain physical or chemical properties to the substituted peptide, such as by selecting amino acids with nonpolar R groups (alanine, valine, leucine, isoleucine, proline, phenylalanine, tryptophan, methionine), uncharged polar R groups (glycine, serine, threonine, cysteine, tyrosine, asparagine, glutamine), or charged polar R groups (aspartic acid, glutamic acid). Likewise, the substitution may be designed specifically to incorporate basic amino acids (lysine, arginine. histidine), aromatic amino acids (phenylalanine, tryptophan, tyrosine), or amino acids of a particular molecular weight.

Amino acid substitutions may also be introduced to substitute an amino acid with a particularly desired property. For example, a Cys may be introduced a potential site for disulfide bridges with another Cys. A His may be introduced as a particularly "catalytic" site. Pro may be introduced because of its particularly planar structure, which induces β-turns in the protein's structure.

The present technology further comprises therapeutic compositions useful in practicing the therapeutic methods of the technology. A therapeutic composition includes, in admixture, a pharmaceutically acceptable excipient (carrier) and one or more of Atsttrin-α variants, or analogs or fragments thereof, as an active ingredient.

A peptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic peptide-, analog- or active fragment-containing compositions are conventionally administered intravenously, as by injection of a unit dose, for example. The term "unit dose" when used in reference to a therapeutic composition of the present technology refers to physically discrete units suitable as unitary dosage for humans, each unit containing a predetermined quantity of active material calculated to produce the desired therapeutic effect in association with the required diluent; i.e., carrier, or vehicle.

The compositions are administered to a subject in need thereof in a manner compatible with the dosage formulation, and in a therapeutically effective amount. The quantity to be administered depends on the subject to be treated, capacity of the subject's immune system to utilize the active ingredient, and degree of inhibition or neutralization of TNF/TNFR activity desired. Precise amounts of active ingredient required to be administered depend on the judgment of the practitioner and are peculiar to each individual. However, suitable dosages may range from about 0.1 to 20, about 0.5 to about 10, or one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

A particular biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In one embodiment, the biocompatible composition is a pharmaceutically acceptable composition. Such compositions can be formulated for administration by topical, oral, parenteral, intranasal, subcutaneous, intrathecal, parenteral and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particular embodiment of the present technology comprises a pharmaceutical composition comprising a therapeutically effective amount of one or more Atsttrin-α variants as described hereinabove, in admixture with a pharmaceutically acceptable carrier. Another embodiment comprises a pharmaceutical composition for the treatment or prevention of a disease characterized by TNF/TNFR activity including, but not limited to, e.g., infections, allograft reactions, inflammation, allergic and autoimmune diseases, and cancer, or a susceptibility to said disease, comprising an effective amount of the Atsttrin-α variants, or pharmaceutically acceptable salts, hydrates, solvates, or prodrugs thereof in admixture with a pharmaceutically acceptable carrier. Another embodiment comprises a pharmaceutical composition for the treatment or prevention of a disease involving inflammation, or a susceptibility to the condition, comprising an effective amount of the Atsttrin-α variants, or pharmaceutically acceptable salts, hydrates, solvates, or prodrugs thereof in admixture with a pharmaceutically acceptable carrier.

The compositions of the present technology may include Atsttrin-α variants in combination with one or more agents suitable for the alleviation, prevention or treatment of inflammation, immunological conditions, hyperproliferative conditions, and/or cancer, such as one or more of an anti-inflammatory agent, an anti-cancer agent, and an immunodulatory agent. Anti-cancer agents include but are not limited to, e.g., tyrosine kinase inhibitors or phosphorylation cascade inhibitors, post-translational modulators, cell growth or division inhibitors (e.g., anti-mitotics), inhibitors, and signal transduction inhibitors. Other treatments or therapeutics may include the administration of suitable doses of pain relief drugs such as non-steroidal anti-inflammatory drugs (e.g., aspirin, paracetamol, ibuprofen or ketoprofen) or opiates such as morphine, or anti-emetics. In addition, the composition may incorporate or be administered with immune modulators, such as interleukins, tumor necrosis factor (TNF) or other growth factors, colony stimulating factors, cytokines or hormones.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Suitable sterile injectable preparations can be a solution or suspension in a non-toxic parenterally acceptable solvent or diluent. Examples of pharmaceutically acceptable carriers are saline, buffered saline, isotonic saline (e.g., monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The agents or compositions of the technology may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be desirable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In a particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J). In general, these polymers are at least partially soluble in aqueous solutions, such as water, buffered salt solutions, or aqueous alcohol solutions that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms of a disease or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are suitable. The data obtained from cell culture assays and animal studies are used in formulating a range of dosage for human use. The dosage of such compounds lies within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this technology may be administered to a subject by a variety of methods. They may be added directly to target tissues, complexed with cationic lipids, packaged within liposomes, or delivered to target cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, e.g., intravenous injection, intramuscular injection, subcutaneous injection, aerosol inhalation, oral (tablet or pill form), topical, systemic, ocular, intraperitoneal and/or intrathecal delivery.

Alternatively, or additionally, a polynucleotide encoding the Atsttrin-α variants may be included within a vector operably linked to signals enabling expression of the nucleic acid sequence. Additionally or alternatively, the vector may be introduced into a cell for purposes of conferring Atsttrin-α variant expression on the cell. Additionally or alternatively, the vector may be a viral vector. A variety of viral-based systems are suitable for use with the present technology, including but not limited to, e.g., adenoviral, retroviral, adeno-associated viral, lentiviral, herpes simplex viral or a sendaiviral vectors.

The viral vectors used in the methods of the present technology may be replication defective. Such replication defective vectors will usually pack at least one region that is necessary for the replication of the virus in the infected cell. These regions can either be eliminated (in whole or in part), or be rendered non-functional by any technique known to a person skilled in the art, including deletion, substitution, partial deletion, or addition of one or more bases to an essential (for replication) region. Such techniques may be performed in vitro (on the isolated DNA) or in situ, using the techniques of genetic manipulation or by treatment with mutagenic agents. The replication defective virus may retain the sequences of its genome, which are necessary for encapsilating, the viral particles.

In one embodiment, the viral element is derived from an adenovirus. The vehicle may include an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid an effective vehicle for incorporating in a library of the present technology. An adenovirus is capable of infecting a wide variety of cells. However, different adenoviral serotypes have different preferences for cells. To combine and widen the target cell population that an adenoviral capsid of the present technology can enter in one embodiment, the vehicle includes adenoviral fiber proteins from at least two adenoviruses. Suitable adenoviral fiber protein sequences are serotype 17, 45 and 51. Techniques or construction and expression of these chimeric vectors are disclosed in US 2003/0180258 and US 2004/0071660, hereby incorporated by reference.

In one embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. The nucleic acid derived from an adenovirus may encode for essentially all adenoviral late proteins, enabling the formation of entire adenoviral capsids or functional parts, analogues, and/or derivatives thereof. The nucleic acid derived from an adenovirus may include the nucleic acid encoding adenovirus E2A or a functional part, derivative, and/or analogue thereof. The nucleic acid derived from an adenovirus may include the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present methods of treatment.

Certain embodiments of the present technology use retroviral vector systems. Retroviruses are integrating viruses that infect dividing cells, and their construction is known in the art. Retroviral vectors can be constructed from different types of retrovirus, such as, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present technology.

In other embodiments of the present technology, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present technology may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present technology include both constitutive promoters and regulated (inducible) promoters. The promoters may be prokaryotic or eukaryotic depending on the host. Among the prokaryotic (including bacteriophage) promoters useful for practice of this technology are lac, lacZ, T3, T7, lambda $P_r$, $P_l$, and trp promoters. Among the eukaryotic (including viral) promoters useful for practice of this technology are ubiquitous promoters (e.g., HPRT, vimentin, actin, tubulin), therapeutic gene promoters (e.g., MDR type, CFTR, factor VIII), tissue-specific promoters, including animal transcriptional control regions, which exhibit tissue specificity and have been utilized in transgenic animals, e.g., immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), and mouse mammary tumor virus control region which is active in testicular, breast, lymphoid and mast cells (Leder, et al. (1986) Cell 45:485-95).

Other promoters which may be used in the practice of the technology include promoters which are preferentially activated in dividing cells, promoters which respond to a stimulus (e.g., steroid hormone receptor, retinoic acid receptor), tetracycline-regulated transcriptional modulators, cytomegalovirus immediate-early, retroviral LTR, metallothionein, SV-40, E1a, and MLP promoters. Further promoters which may be of use in the practice of the technology include promoters which are active and/or expressed in dendritic cells.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et. al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

In addition, the present technology comprises preparing Atsttrin-α variants using peptidomimetics, and peptidomimetic bonds, such as ester bonds. In some embodiments, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide antagonists with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189-199; Hruby, et al., 1990, Biochem J. 268:249-262.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as -carboxyl-glutamic acid (Gla) (Bachem) to chelate a transition metal and form a cross-link. Protected-carboxyl glutamic acid may be prepared by modifying the synthesis described by Zee-Cheng and Olson (1980, Biophys. Biochem. Res. Commun. 94:1128-1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present technology contemplates strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137-167; Ponsanti, et al., 1990, Tetrahedron 46:8255-8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski, et al., 1991, J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3_carboxylate (Miyake, et al., 1989, J. Takeda Res. Labs. 43:53-76); -carboline (D and L) (Kazmierski, 1988, Ph. D. Thesis, University of Arizona); HIC (histidine isoquinoline carboxylic acid) (Zechel, et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2_propenidone-6-carboxylic acid), a-turn inducing dipeptide analog (Kemp, et al., 1985, J. Org. Chem. 50:5834-5838); -sheet inducing analogs (Kemp, et al., 1988, Tetrahedron Lett. 29:5081-5082); -turn inducing analogs (Kemp, et al., 1988, Tetrahedron Lett. 29:5057-5060);_helix inducing analogs (Kemp, et al., 1988, Tetrahedron Lett. 29:4935-4938); -turn inducing analogs (Kemp, et al., 1989, J. Org. Chem. 54:109:115); and analogs provided by the following references: Nagai and Sato, 1985, Tetrahedron Lett. 26:647_650; DiMaio, et al., 1989, J. Chem. Soc. Perkin Trans. p. 1687; also a Gly-Ala turn analog (Kahn, et al., 1989, Tetrahedron Lett. 30:2317); amide bond isostere (Jones, et al., 1988, Tetrahedron Lett. 29:3853-3856); tretrazol (Zabrocki, et al., 1988, J. Am. Chem. Soc. 110:5875-5880); DTC (Samanen, et al., 1990, Int. J. Protein Pep. Res. 35:501:509); and analogs taught in Olson, et al., 1990, J. Am. Chem. Sci. 112:323-333 and Garvey, et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present technology further comprises modification or derivatization of the polypeptide or peptide of the technology. These modifications may serve to alter or increase the stability, activity, half-life of the polypeptide or peptide of the technology. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_nCH_3$ may be incorporated in the peptide. This and other peptide-fatty acid conjugates suitable for use in the present technology are disclosed in U.K. Patent GB-8809162.4, International Patent Application PCT/AU89/00166, and reference 5, supra. Addition of carbohydrate moieties and the preparation and use of glycosylated analogs of the peptides of the technology is also contemplated, including for improved biological and physical properties such as proteolytic stability and in vivo activity.

Chemical Moieties For Derivatization.

Derivatives of the peptides (including variants, analogs and active fragments thereof) of the present technology are further provided. Such derivatives encompass and include derivatives to enhance activity, solubility, effective therapeutic concentration, and transport across the blood brain barrier. Further encompassed derivatives include the attachment of moieties or molecules which are known to interact with TNF/TNFR, to target TNF/TNFR or expressing cells, or to have anti-inflammatory activity. The chemical moieties may be N-terminally or C-terminally attached to the peptides of the present technology. Chemical moieties suitable for derivatization may be, for instance, selected from among water soluble polymers. The polymer selected can be water soluble so that the component to which it is attached does not precipitate in an aqueous environment, such as a physiological environment. Where a therapeutic use of the end-product is intended, the polymer will be pharmaceutically acceptable. The polymer may be branched or unbranched. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols and polyvinyl alcohol. Polyethylene glycol propionaldenhyde may have advantages in manufacturing due to its stability in water.

The polymer may be of any suitable molecular weight, and may be branched or unbranched. For polyethylene glycol, a suitable molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivative, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik, et al., 1992, *Exp. Hematol.* 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the terminal amino acid residues; those having a free carboxyl group include aspartic acid residues and glutamic acid residues and the C-terminal amino acid residue. Sulfhydrl groups may also be used as a reactive group for attaching the polyethylene glycol molecule(s). Suitable for therapeutic purposes is attachment at an amino group, such as attachment at the N-terminus or lysine group.

More particularly, the present technology comprises derivatives which are fusion proteins comprising the peptides of the present technology or fragments thereof. Thus peptides of the present technology and fragments thereof can be "modified" i.e., placed in a fusion of chimeric peptide or protein, or labeled, e.g., to have an N-terminal FLAG-tag. In a particular embodiment a peptide can be modified by linkage or attachment to a marker protein such as green fluorescent protein as described in U.S. Pat. No. 5,625,048 filed Apr. 29, 1997 and WO 97/26333, published Jul. 24, 1999 (each of which are hereby incorporated by reference herein in their entireties). In one such embodiment, a chimeric peptide can be prepared, e.g., a glutathione-S-transferase (GST) fusion protein (or fragments thereof), a maltose-binding (MPB) protein fusion protein, or a poly-histidine-tagged fusion protein, for expression in a eukaryotic cell. Expression of the peptide of the present technology as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the peptide and the fusion partner (e.g., GST, MBP, or poly-His). Alternatively the chimeric peptide may contain the green fluorescent protein, and be used to determine the intracellular localization of the peptide in the cell.

The present technology also comprises derivatives wherein at least one of the attached chemical moieties is a molecule having multiple sites for peptide attachment and capable of binding at least two of said peptides simultaneously to generate a multimeric peptide structure. This derivative has the effect of increasing the available local concentration of the carbohydrate epitope mimic peptide(s) of the present technology. Alternatively, or in addition, such moieties can function in providing a stable scaffold to retain the peptide in place for activity, thereby reducing or preventing diffusion or degradation. More particularly, such molecule is selected from the group of BSA, ovalbumin, human serum allbumin, polyacrylamide, beads and synthetic fibers (biodegradable and non-biodegradable).

The carbohydrate epitope mimic peptide of the present technology may be prepared and utilized as monomers, dimers, multimers, heterodimers, heteromultimers, etc. Presentation or administration of the peptide in multimeric form may result in enhanced activity or otherwise increased modulation of the activity mediated by the peptide(s), including TNF antagonistic activity and/or inhibiting TNF/TNFR signaling and activity. The peptide monomer could be produced in a variety of ways. The peptide of the present technology can be synthesized using a protein synthesizer and utilizing methods well known in the art and as described hereinabove, incorporating amino acid modifications, analogs, etc. as hereinabove described. In addition, the DNA sequence of the peptide can be inserted into an expression vector such as pSE (Invitrogen) or pcDNA3 (Invitrogen) for production in bacterial or mammalian cell expression systems. Insect or yeast expression systems could also be used. Purification of the peptide could be facilitated by the addition of a tag sequence such as the 6-Histidine tag which binds to Nickel-NTA resins. These tag sequences are often easily removed by the addition of a protease specific sequence following the tag. Dimers and multimers of the peptide can be produced using a variety of methods in the art. The DNA sequence of a dimer or multimer could also be inserted into an expression system such as bacteria or mammalian cell systems. This could produce molecules such as Met-FLHTRLFV)$_x$ where x=2, 3, 4, etc. It may be necessary to include a short flexible spacer (Gly-Gly-Gly-Gly-Ser)$_3$ between the peptide or peptidomimetic to increase its effectiveness. Dimers and multimers can also be generated using crosslinking reagents such as Disuccinimidyl suberate (DSS) or Dithoiobis (succinimidyl propionate) (DSP). These reagents are reactive with amino groups and could crosslink the peptide through free amine groups at the arginine residues and the free amine group at the N-terminus. Dimers and multimers can also be formed using affinity interactions between biotin and avidin, Jun and Fos, and the Fc region of antibodies. The purified peptide can be biotinylated and mixed with factors that are known to form strong protein-protein interactions. The peptide or peptidomimetic could be linked to the regions in Jun and Fos responsible for dimer formation using crosslinkers such as those mentioned above or using molecular techniques to create a peptide-Jun/Fos molecule. When the Jun and Fos peptide hybrids are mixed, dimer formation would result. In addition, production of a peptide-Fc hybrid could also be produced. When expressed in mammalian cells, covalent disulfide bonds form through cysteines in the Fc region and dimer formation would result. Heterodimers and heteromultimers of the peptide could also be produced. This would generate possible multifunctional molecules where parts of the whole molecule are responsible for producing a multitude of effects, such as anti-TNF and/or anti-inflammatory and/or cell growth modulating effects. The same technologies as those listed above could be used to generate these multifunctional molecules. Molecular techniques could be used to insert the carbohydrate epitope mimic peptide into a protein at the DNA level. This insertion could take place at the N- or C-terminus, or in the middle of the protein molecule. Heterodimers could be formed using peptide/Fc or peptide/June or Fos hybrid molecules. When mixed with other Fc or Jun/Fos containing hybrids dimer formation would result producing heterodimers. Crosslinking reagents could also be used to link the peptide to heterodimers. Lastly, biotinylation of the peptide along with biotinylation of other molecules could be used to create multimers. Mixing of these components with avidin could create large multifunctional complexes, where each of the four biotin binding sites of the avidin molecule is occupied by a different biotinylated molecule.

Methods of the Present Technology

In one aspect, the present technology comprises methods for inhibiting TNF and/or TNFR signaling in a cell, comprising contacting the cell with an effective amount of a composition of the present technology. In some embodiments, the composition comprises one or more amino acid sequences selected from a group consisting of SEQ ID NO:3, SEQ ID NO:4, or SEQ ID NO:5. In some embodiments, the TNF is TNFα. In some embodiments, the TNFR is TNFR1 or TNFR2. In some embodiments, the cell is in vivo or in vitro.

In another aspect, the present technology comprises methods for preventing or treating a disease or medical condition caused by or resulting in TNF and/or TNFR signaling in a subject in need thereof. In some embodiments, the methods comprise administering to the subject an effective amount of PGRN, Atsttrin-α, or an Atsttrin-α variant, or combination thereof. In some embodiments, the methods comprise administering to the subject an effective amount of one or more amino acid sequences selected from a group consisting of SEQ ID NO:3, SEQ ID NO:4, or SEQ ID NO:5.

In some embodiments, the disease or medical condition is an inflammatory disease or condition, an immunological disease, or cancer. In some embodiments, the inflammatory disease is rheumatoid arthritis, osteoarthritis, ankylosing spondylitis, psoriasis, inflammatory bowel diseases, Crohn's disease, ulcerative colitis, uveitis, inflammatory lung diseases, or chronic obstructive pulmonary disease. In some embodiments, the immunological disease or condition is an allergic disease or an autoimmune disease or condition. In some embodiments, the inflammation is acute inflammation. In some embodiments, the inflammation is chronic inflammation.

In vivo animal models of TNF/TNFR family-mediated diseases or conditions may be utilized by the skilled artisan to further or additionally evaluate, assess, screen and/or verify the Atsttrin-α variants of the present technology or agents or compounds identified in or in accordance with the present technology. Animal models may be used to demonstrate the efficacy of a particular Atsttrin-α variant composition in mediating, alleviating or controlling the development and progression of TNF/TNFR-mediated diseases or conditions, inflammatory conditions, immune diseases or conditions (including allergies an auto-immune diseases), bone diseases or conditions, or other possible targeted conditions. Animal models or studies include those described and detailed herein and in the examples. For example, TNFα transgenic mice develop arthritis and provide a useful tool for evaluating the efficacy of novel therapeutic strategies for rheumatoid arthritis. Additional animal models include, but are not limited to, e.g., ulcerative colitis models, multiple sclerosis models (including EAE, lysolecithin-induced), arthritis models, allergic asthma models, airway inflammation models, psoriasis models, and acute inflammation models. The EAE animal model of multiple sclerosis provides an acute or chronic-relapsing, acquired, inflammatory and demyelinating autoimmune disease. Allergy models may be utilized as models of immunological injury and conditions. Osteoarthritis models include for example experimental osteoarthritis induced in rabbits after sectioning of the knee anterior cruciate ligament and in rats after tear of the medial collateral ligament. Appropriate bone disease, bone injury, and/or osteoporosis models are also known and available to one of skill in the art.

In some embodiments, the present technology comprises the use of Atsttrin-α variants or derivatives thereof for prevention, treatment, or alleviation of rheumatoid arthritis and osteoarthritis. In some embodiments, the present technology comprises the use of Atsttrin-α variants or derivatives thereof for prevention, treatment, or alleviation of TNF-related diseases, including inflammatory conditions, immune conditions including auto-immune diseases, bone diseases and cancer. TNF-related diseases include rheumatoid arthritis, osteoarthritis, ankylosing spondylitis, psoriasis, inflammatory bowel diseases, Chrohn's disease, ulcerative colitis, uveitis, inflammatory lung diseases, chronic obstructive pulmonary disease, multiple sclerosis, osteoporosis, osteosarcoma. In some embodiments, the present technology comprises the use of Atsttrin-α variants or derivatives thereof for facilitating or mediating tissue repair. In some embodiments, the present technology comprises the use of Atsttrin-α variants or derivatives thereof for prevention, treatment, or alleviation of immunological injury and conditions, including allergies and auto-immune diseases, such as lupus and multiple sclerosis. In some embodiments, the present technology comprises the use of Atsttrin-α variants or derivatives thereof for prevention, treatment, or alleviation of cancer and tumor or cancer cell growth, including in PGRN and/or TNF/TNFR-mediated cancers or other such hyperproliferative disorders.

In one aspect, the present technology comprises a method of preventing and/or treating a disease characterized by, mediated by or facilitated by TNF/TNFR activity and/or signaling and/or a diseases characterized by inflammation, immune injury, and cancer, said method comprising administering to a subject a therapeutically effective amount of a Atsttrin-α variant.

In some embodiments, the disease is selected from rheumatoid arthritis, osteoarthritis, ankylosing spondylitis, psoriasis, inflammatory bowel diseases, Chrohn's disease, ulcerative colitis, uveitis, inflammatory lung diseases, and chronic obstructive pulmonary disease. In some embodiments, the disease may be an immunological disorder or condition, including allergies and auto-immune diseases, such as lupus and multiple sclerosis. In other embodiments, the disease is cancer, including a PGRN-mediated cancer or TNF/TNFR-mediated cancer.

Dosages

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are suitable. While compounds that exhibit toxic side effects may be used, care should be taken to design a delivery system that targets such compounds to the site of affected tissue in order to minimize potential damage to cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the effective amount of Atsttrin-α variant for achieving a therapeutic or prophylactic effect ranges from about $10^{-11}$ mg per kilogram body weight per day to about $10^6$ mg per kilogram body weight per day. In some embodiments, the effective amount of Atsttrin-α variant for achieving a therapeutic or prophylactic effect is about $10^{-11}$, about $10^{-10}$, about $10^{-9}$, about $10^{-8}$, about $10^{-7}$, about $10^{-6}$, about $10^{-5}$, about $10^{-4}$, about $10^{-3}$, about $10^{-2}$, about $10^2$, about $10^3$, about $10^4$, about $10^5$, or about $10^6$ mg per kilogram body weight per day. In some embodiments, the dosage ranges are from about 0.0001 mg per kilogram body weight per day to about 100 mg per kilogram body weight per day, and are administered every day, every two days or every three days, or within the range of 1-10 mg/kg every week, every two weeks or every three weeks. In one embodiment, a single dosage of peptide ranges from 0.1-10,000 micrograms per kg body weight. An illustrative treatment regime comprises administration once per day or once a week. In some embodiments, a relatively high dosage at relatively short intervals is used until disease progression is reduced or terminated, or until the subject shows partial or complete amelioration of symptoms of disease. Thereafter, the patient is administered a prophylactic regime.

In some embodiments, a therapeutically effective amount of an peptide is a concentration of peptide at the target tissue of about $10^{-11}$ to about $10^{-3}$ molar. In some embodiments, the concentration of peptide is about $10^{-11}$, about $10^{-10}$, about $10^{-9}$, about $10^{-8}$, about $10^{-7}$, about $10^{-6}$, about $10^{-5}$, about $10^{-4}$, about $10^{-3}$, or about $10^{-2}$ molar. This concentration may be delivered by systemic doses of 0.01 to 100 mg/kg or equivalent dose by body surface area. The schedule of doses would be optimized to maintain the therapeutic concentration at the target tissue, such as with single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In a suitable embodiment, the mammal is a human.

Combination Therapies

In one aspect, the present technology comprises methods of preventing or treating a disease caused by or resulting in TNF or TNFR signaling, comprising administering to a subject in need thereof an effective amount of PGRN, Atsttrin-α, or an Atsttrin-α variant described herein in combination with one or more therapeutic agents.

In some embodiments, the therapeutic agent is directed to the prevention or treatment of an inflammatory disease, an immunological disease, or cancer. In some embodiments, the inflammatory disease is rheumatoid arthritis, osteoarthritis, ankylosing spondylitis, psoriasis, inflammatory bowel diseases, Crohn's disease, ulcerative colitis, uveitis, inflammatory lung diseases, or chronic obstructive pulmonary disease.

In some embodiments, the immunological disease is an allergic disease or an autoimmune disease.

In another aspect, the present technology comprises peptide comprising one or more granulin units and one or more linker units of progranulin (PGRN), or variants thereof, wherein the peptide is capable of antagonizing signaling by TNF or TNFR family members, formulated in a composition with one or more therapeutic agents. In some embodiments, the therapeutic agent is selected from a group consisting of an anti-inflammatory agent, an anti-cancer agent, and an immunomodulatory agent.

EXAMPLES

The following examples are presented in order to more fully illustrate the embodiments of the present technology. These examples should in no way be construed as limiting the scope of the technology, as defined by the appended claims.

Materials and Methods

Mice. All animal studies were performed in accordance with institutional guidelines and with approval by the Institutional Animal Care and Use Committee of New York University. C57BL/6, BALB/c, DBA/1J, TNFR1 knockout (Tnfrsf1a$^{-/-}$) and TNFR2 knockout (Tnfrsf1b$^{-/-}$) mice were obtained from Jackson Laboratories, Bar Harbor, Me., USA. TNFα transgenic (hemizygous) mice were obtained from Taconic. The generation and characterization of PGRN knockout mice has been described previously.

Preparation of rhPGRN and Atsttrin-α1 protein. Generation of PGRN stable line and purification of recombinant PGRN has been described previously. See J Q Feng, et al., FASEB 24:1879-1892 (2010).

For expression of GST fusion Atsttrin-α1, the appropriate plasmid pGEX-Atsttrin-a1 was transformed into *E. coli* DE3. Fusion protein was affinity-purified on glutathione-agarose beads as previously described with slight modification. Briefly, glutathione-agarose beads bearing GST fused Atsttrin-α1 was digested with Factor Xa for six hours at room temperature and the supernatant was collected. Following the removal of Factor Xa by using Factor Xa Removal Resin (QIAGEN), the purity of resulted Atsttrin-α1 was determined by SDS-PAGE and reverse phase HPLC.

Yeast two-hybrid (Y2H) library screen. Plasmid pDBleu-PGRN (aa 21-588) encoding PGRN lacking signal peptide was used as bait to screen a Y2H murine 10.5-day embryonic cDNA library (Life Technologies, Grand Island, N.Y., USA) according to a modified manufacturer's protocol. Briefly, bait plasmid was introduced into a yeast MAV203 strain that contained three reporter genes, HIS$^+$, URA$^+$, and Lac Z, and the cDNA library in the vector pPC86 was then transformed into the resultant Leu yeast strain and plated on medium lacking tryptophan, leucine, histidine, and uracil but containing 25 mM 3-amino-1,2,4-trizone. After incubation for 7-10 days at 30° C., colonies were screened for β-galactosidase by a filter lift assay.

Assay of protein-protein interactions using the Y2H system. Independent yeast colonies were analyzed for the interaction of two proteins, one of which was fused to the Gal4 DNA binding domain and the other, to the VP16 transactivation domain. Previously published procedures were followed for 1) growing and transforming the yeast strain MAV203 with the selected plasmids; and 2) determining β-galactosidase activity and growth phenotypes on selective media lacking tryptophan, leucine, histidine, and uracil.

To quantify the interactions, yeast colonies were harvested, lysed and activity determined by a liquid assay for β-galactosidase. β-galactosidase activity was monitored at 420 nm, and 1 unit of β-galactosidase activity was defined as the amount capable of hydrolysing 1 μmol of o-nitrophenyl-β-D-galactopyranoside to o-nitrophenol and D-galactose per min per cell.

Co-immunoprecipitation (Co-IP). Approximately 500 μg of cellular extract prepared from isolated human chondrocytes was incubated with anti-PGRN, anti-TNFR1, anti-TNFR2 or control IgG (25 μg/ml) antibodies for 1 hr, followed by incubation with 30 μl of protein A-agarose at 4° C. overnight. Bound protein was examined by Western blotting with anti-TNFR1, anti-TNFR2 or anti-PGRN antibodies.

Solid-phase binding. To determine whether PGRN directly binds to TNFR in vitro, microtiter plates were coated with 500 ng of PGRN in 100 μl of TBS buffer (50 mM Tris-HCl, 150 mM NaCl, pH 7.4) overnight at 4° C. Wells were blocked using 1% bovine serum albumin (BSA) in TBS buffer for 3 h at 37° C. After washing with TBS and 0.05% Tween, various amounts of TNFR1 extracellular domain or TNFR2 extracellular domain (R & D System) were added. Bound protein from the liquid phase was detected by anti-TNFR1 or anti-TNFR2 antibodies.

To examine the inhibition of the TNF/TNFR or LTα/TNFR interaction by PGRN or Atsttrin-α1, plates were coated with 100 ng of TNFα (R & D System, Minneapolis, Minn., USA) or LTα (R & D System). 100 ng of TNFR1 extracellular domain or 100 ng of TNFR2 extracellular domain (R & D System) was then added in the presence of various amounts of PGRN or Atsttrin-α1. Bound TNFR was detected as described above.

Surface plasmon resonance analysis. A COOH1 sensor chip was installed and thermally equilibrated 10 min. SensiQ Pioneer contains a three channel flow cell enabling simultaneous analysis of multiple ligands. Channel 1 was immobilized with TNFR2 and channel 3 was immobilized with TNFR1. Channel 2 was left unmodified to serve as a reference. Immobilization by random amine coupling was used where surface carboxyl groups were activated by injecting a mixture of 4 mM EDC and 1 mM NHS in deionized water for 3.5 min. Each receptor sample was diluted to 30 μg/ml in 10 mM acetate pH 4.7 and injected for 20 min over the respective channel. Remaining NHS esters were capped by injecting 1M ethanolamine pH 8.0 for 4 min.

The samples of analytes (TNFα, rhPGRN and Atsttrin-α1) were diluted to 400 nM in running buffer and each was injected using the FastStep™ injection type. Signal The FastStep™ injection incorporates a wide dilution range of a stock sample in a single injection. The dilution range is created from the stock solution within the Pioneer fluidics so additional vials are not required for a traditional dilution series. The FastStep™ injection used produced a doubling dilution series over 6 concentrations starting at 400 nM for each analyte. Following the analyte injection, dissociation of analyte-ligand complex was monitored for 8 min before the surface was regenerated by injecting 10 mM NaOH for 2 min. Each sample was injected in duplicate and a buffer blank was included for double referencing. The sample binding response over a blank surface (channel 2) and the response recorded for injection of a blank buffer are subtracted from the sample binding response over the receptor coated surface to accurately resolve specific binding in the presence of non-specific binding and systematic bias. The FastStep™ injection type allowed a full kinetic assay to be performed in a single injection and it used only one stock solution. All parameters of the analysis were fitted globally using 1:1 kinetic model.

Flow cytometry assay. Raw 264.7 cells were resuspended in 10 mM PBS, and $1 \times 10^5$ cells were pretreated with different dose of rhPGRN or Atsttrin-α1 for 30 min, after which the Biotinylated human TNFα (Bt-hTNFα, R&D Systems) was added. Cells were incubated for 30 min in 4° C. 10 µl of avidin-FITC was added and incubated for a further 30 min at 4° C. in the dark. The cells were washed twice and re-suspended in 200 µl wash buffer for final flow cytometric analysis.

Neutrophil activation assay. Wild type or PGRN-deficient neutrophils resuspended in ice-cold Krebs-Ringer phosphate buffer with glucose (KRPG) were used for measurement of $H_2O_2$ production using the scolopetin assay with $1.5 \times 10^4$ neutrophils per well. Cells were treated with 100 ng/ml of TNFα (R&D systems) in the presence or absence of Atsttrin-α1, and incubated at 37° C. for 3 h. $H_2O_2$ production was measured in a fluorescence microplate reader.

Nitrite production assay. Bone marrow cells collected from the femurs of 5- to 8-wk-old wild type or PGRN-deficient mice were suspended in culture medium (α-MEM containing L-glutamine, penicillin, streptomycin and heat-inactivated 10% v/v FBS) supplemented with 10 ng/ml M-CSF and cultured overnight. Non-adherent bone marrow derived macrophages (BMDMs) were cultured in 96-well flat-bottom plates ($1.25 \times 10^5$ cells/well) for 2 days in the presence of M-CSF (10 ng/ml). BMDMs were then incubated for 24 h with 100 ng/ml TNF (R&D systems) in the presence or absence of various amounts of Atsttrin-α1. Cell culture supernatants were harvested and tested for NO via the Griess reaction.

In vitro suppression assays. $CD4^+CD25^+$ and $CD4^+CD25^-$ T cells were purified from the peripheral blood of healthy human donors between ages of 16 and 75 years. Briefly, the whole blood was incubated (20 min, 22° C.) with Rosette-Sep™ human $CD4^+$ T cell enrichment cocktail (StemCell Technologies, Vancouver, BC, Canada). The remaining unsedimented cells were loaded onto Ficoll-Paque™ Plus (Amersham Bioscience, Piscataway, N.J., USA), isolated by density centrifugation, and washed with PBS. In second round of purification, $CD4^+$ T cells were separated into $CD25^-$ and $CD25^+$ populations with magnetically coupled mAb against human CD25 (Miltenyi Biotec, Bergisch Gladbach, Germany). $CD4^+CD25^+$ T cells were mixed at ratio 1:3 or $1.25 \times 10^5$ to $5 \times 10^5$ with $CD4^+CD25^-$ T cells at final concentration $2 \times 10^6$/ml and treated with different doses of rhPGRN (10-500 ng/ml). Then, the cells were plated on anti-CD3 mAb (5 µg/ml) pre-coated 24-well plates in the absence or presence of human TNFα (210-TA; R&D Systems Inc (Minneapolis, Minn.)) and cultured for 24-48 hr. Cytokine secretion was determined by ELISA by using Human IFNγ Cytoset™ (Biosource; Camarillo, Calif., USA).

$CD4^+$ T cells differentiation in vitro. Naïve $CD4^+$ T cells were enriched by CD4 T cell negative selection kit (STEM CELL) combined with addition of Bio-anti CD-25 and Bio-anti-CD44 for depleting $CD25^+$ regulatory T cells and CD44 activated cells. Cells were activated by coated anti-CD3 and soluble anti-CD28 for Th1 (anti-IL-4, 10 µg/ml; IL-12, 10 ng/ml), Th2 (anti-IFNγ, 10 µg/ml; anti-IL-12, 10 µg/ml; IL-4, 20 ng/ml), Th17 (anti-IFNγ, 10 µg/ml; anti-IL-12, 10 µg/ml; anti-IL-4, 10 µg/ml; IL-6, 20 ng/ml; TGFβ, 1 ng/ml), and Treg (anti-IFNγ, 10 µg/ml; anti-IL-12, 10 µg/ml; anti-IL-4, 10 µg/ml; IL-2, 2 ng/ml; TGFβ, 2.5 ng/ml) in the absence (Ctrl) or presence (rhPGRN) of 100 ng/ml of rhPGRN polarization for 5 days. After re-stimulation with PMA and ionomycin in the presence of Golgi plug for 4 hours, cell surface staining was performed with anti-CD4 followed by intracellular cytokine staining for IL-4, IFNγ, IL-17 and FoxP3.

Osteoclast formation and activity. BMDMs were obtained as described above and the resultant preosteoclasts were cultured in medium supplemented with 10 ng/ml M-CSF and 100 ng/ml TNF for 4 days. The cells were fixed with formalin and stained for tartrate-resistant acid phosphatase (TRAP) with a TRAP solution containing 100 mM sodium acetate buffer (pH 5.0), 50 mM sodium tartrate, 0.1 mg/ml sodium naphtol AS-MX phosphate, 0.6 mg/ml Fast Violet LB, and 0.1% Triton X-100. TRAP-positive cells appeared dark red and TRAP-positive multinucleated cells ($TRAP^+$-MNCs) containing more than three nuclei were counted using light microscopy. Osteoclast activity was assessed with pit formation assays by using the BD BioCoat Osteologic bone cell culture system (BD Biosciences).

Cytotoxicity assay. Rhabdomyosarcoma A673/6 cells were seeded in a 96-well plate at $3 \times 10^4$ cells/well and incubated for 16 h. Serial dilutions of PGRN, Atsttrin-α1, or BSA were prepared in medium containing 80 pg/ml TNFα and 2 µg/ml actinomycin D. Following incubation at 39° C. for 18-24 hr, each well was rinsed once with PBS. The adherent cells were then fixed by adding 10% formalin in PBS for 15 min at room temperature, and stained with 0.5% naphthol blue black in 9% acetic acid and 0.1M sodium acetate. After 30 min at room temperature, the cells were rinsed with distilled water, and the bound dye was eluted with 50 mM NaOH. Absorbance of the eluted dye was determined at a wavelength of 630 nm.

Cartilage explants. Articular cartilage collected from wild type or PGRN deficient mice was dispensed into 96-well plates and incubated overnight in control, serum-free Dulbecco's modified Eagle's medium (DMEM; Invitrogen) containing 25 mM HEPES, 2 mM L-glutamine, 100 µg/ml streptomycin, and 100 IU/ml penicillin. Fresh control medium (0.2 ml) containing TNFα (5 ng/ml) was then added (day 0). On day 2, supernatants were collected and the COMP degradation determined by immunoblotting with anti-COMP antibodies.

Collagen antibody induced arthritis (CAIA) model. 5 to 6-week-old female BALB/c mice were injected intravenously with a 2 mg cocktail containing four antibodies against type II collagen (Chondrex, LLC, Seattle, Wash., USA) (day 0). On day 3, an intraperitoneal injection of lipopolysaccharide (LPS) (Chondrex, LLC, Seattle, Wash.) was given to enhance the incidence and severity of disease (50 µg/mouse). CAIA mice were given an intraperitoneal injection of PBS, 10 mg/kg rhPGRN, or 10 mg/kg Atsttrin-α1 every other day, starting on day 1. Hind paw thickness was measured every other day, using a digital caliper.

Collagen induced arthritis (CIA) model. 8-week-old male DBA1/J mice were immunized via a 0.1 ml intradermal injection at the base of the tail with 100 µg chicken type II collagen (Chondrex, LLC, Seattle, Wash.) emulsified with an equal volume of complete Freund's adjuvant (CFA) containing 4 mg/ml heat-denatured mycobacterium (Chondrex, LLC, Seattle, Wash.) (day 0). To determine preventative effects, various amounts of rhPGRN or Atsttrin-α1 were administered intraperitoneally every other day or once a week, starting on day 19 following primary immunization. To determine therapeutic effects, various amounts of Atsttrin-α1 were also applied to mice with established severe arthritis (clinical score≥10).

8-week-old male PGRN-deficient mice and their wild type littermates (C57BL/6 background) were primarily immunized with chicken type II collagen (Chondrex, LLC, Seattle, Wash.) (as described in the preceding paragraph), and a booster injection of 100 µg chicken type II collagen emulsified with an equal volume of complete Freund adjuvant (Chondrex, LLC, Seattle, Wash.) was administered on day 21. To determine whether PGRN could reverse the inflammation seen in challenged PGRN-deficient mice, recombinant PGRN (10 mg/kg body weight) was injected intraperitoneally every other day beginning at 4 weeks following the initial primary immunization.

To determine the TNFR dependence of Atsttrin-α1's therapeutic effects, 8-week-old male Tnfrsf1a$^{-/-}$, Tnfrsf1b$^{-/-}$ and wild type C57BL/6 mice were immunized as described above. And the mice with established mild arthritis (clinical score 4-6) were injected intraperitoneally with various amounts of Atsttrin-α1 once every week.

Human TNFα transgenic model (TNF-Tg): TNF-Tg/Grn$^{-/-}$ mice were generated by crossing TNF-Tg mice with Grn$^{-/-}$ mice, and subsequent TNF-Tg/Grn$^{-/-}$ mice were obtained by crossing TNF-Tg/Grn$^{+/-}$ with Grn$^{-/-}$ mice. The spontaneous development of inflammatory arthritis in TNF-Tg, TNF-Tg/Grn$^{+/-}$, and TNF-Tg/Grn$^{-/-}$ mice was recorded, and paws were scored for disease severity. To evaluate the possible therapeutic effects of PGRN, TNF-Tg mice with established arthritis (clinical score 4-6) were administered intraperitoneal PBS or rhPGRN (10 mg/kg body weight) twice per week. At 4 weeks, the treatment groups were then switched. To determine the possible therapeutic effects of Atsttrin-α1, TNF-Tg mice with mild (clinical score 4-6) or severe (clinical score ≥10) arthritis were administered intraperitoneal PBS or Atsttrin-α1 (2.5 mg/kg body weight) twice per week.

Evaluation for clinical arthritis. Clinical signs of arthritis in CAIA, CIA, and TNF-Tg mouse models were evaluated to determine arthritis incidence. Each paw was evaluated and scored individually using a 0 to 4 scoring system. The paw scores were summed to yield individual mouse scores, with a maximum score of 16 for each animal. The scores, as follows: a paw score of 0, no signs; 1, mild swelling confined to the tarsal bones or ankle joint; 2, mild swelling extending from the ankle to the tarsal bones; 3, moderate swelling extending from the ankle to the metatarsal joints; and 4, severe swelling encompassing the ankle, foot and digits, or ankylosis of the limb.

Histopathological examination of joints. Following routine fixation, decalcification, and paraffin embedding, tissue sections were prepared and stained with hematoxylin and eosin. All slides were coded and submitted for evaluation by investigators blinded to the experimental conditions. The extent of synovitis, pannus formation, and bone/cartilage destruction was determined using a graded scale, as follows: grade 0, no signs of inflammation; grade 1, mild inflammation with hyperplasia of the synovial lining without cartilage destruction; grades 2 through 4, increasing degrees of inflammatory cell infiltrate and cartilage/bone destruction. Sections were also stained with 0.1% Safranin O or TRAP for detection of cartilage proteoglycans or osteoclast activity, respectively.

TNF intracellular signaling assays. BMDMs were stimulated with 10 ng/ml TNFα in the presence or absence of 2.5 nM rhPGRN or Atsttrin-α1. At the indicated times, total cell lysate or cytoplasmic and nuclear extracts were prepared following published protocols. Cell extracts (~30 μg) were resolved on a 10% SDS-PAGE gel, and probed using specific antibodies against total and phosphorylated IKKα, IKKβ, IκBα, NF-κB p65, Erk1/2, p38, and JNK.

Immunohistochemistry. The tarsal joints of CIA mice treated with PBS, rhPGRN, or Atsttrin-α1 were sectioned, deparaffinized, rehydrated, and incubated in Tris buffer (10 Mm Tris-HCl (pH 8.0), 150 mM NaCl). The samples were then incubated with rabbit anti-mouse phosphorylated IκBα (1:100) at 4° C. overnight. Then, the sections were incubated for 30 min with biotinylated anti-rabbit IgG (Vector, Burlingame, Calif.) and subsequently stained using a biotin-strepta-vidin-peroxidase protocol (Vector). Horseradish peroxidase (HRP) activity was detected using 3,3'-diaminobenzidine and $H_2O_2$. Slides were counterstained with 0.5% Methyl green.

Chromatin Immunoprecipitation (ChIP). BMDMs were stimulated with TNFα (10 ng/ml) for 1 h, in the presence or absence of rhPGRN/Atsttrin-α1 (2.5 nM). The cells were then treated with formaldehyde, and the sonicated supernatant fraction was incubated with antibodies against NF-κB p65 (Santa Cruz Biotechnology, Santa Cruz, Calif., USA) or control IgG at 4° C. overnight. 10% of the chromatin-immunoprecipitated DNA was used as template to amplify a 230 bp-segment of the IκBα gene promoter bearing a NF-κB binding site using forward primer 5'-TGGCGAGGTCT-GACTGTTGTGG-3' (SEQ ID NO:12), and reverse primer 5'-GCTCATCAAAAAGTTCCCTGTGC-3' (SEQ ID NO:13).

Reporter gene. To examine whether PGRN and Atsttrin-α1 inhibit TNF-mediated transactivation of NF-κB-dependent reporter genes, BMDMs grown to ~50% confluence were transfected with 1 μg of the p6XNF-κB-Luc reporter plasmid and 1 μg of the pSVGal plasmid (internal control), using FuGene HD (Roche Applied Science, Basel, Switzerland). 48 hours following transfection, the cells were starved overnight and then stimulated for 6 h with 10 ng/ml TNFα in the presence or absence of 0.1, 0.5, or 2.5 nM rhPGRN or Atsttrin-α1. Luciferase and β-Galactosidase activities were then measured.

Real-time PCR. Total RNA was isolated from BMDMs stimulated with TNFα (10 ng/ml) in the presence or absence of rhPGRN or Atsttrin-α1 (2.5 nM) for 3 h, and then reverse-transcribed to cDNA. Real time PCR was performed with the following sequence-specific primers: 5'-TACAAGCTG-GCTGGTGGGGA-3' (SEQ ID NO:14) and 5'-GTCGCGGGTCTCAGGACCTT-3' (SEQ ID NO:15) for NFκB2; 5'-AATCTCACAGCAGCACATCA-3' (SEQ ID NO:16) and 5'-AAGGTGCTCATGTCCTCATC-3' (SEQ ID NO:17) for IL-1β; 5'-CCTTCCTACCCCAATTTCCAAT-3' (SEQ ID NO:18) and 5'-GCCACTCCTTCTGTGACTC-CAG-3' (SEQ ID NO:19) for IL-6; 5'-CTTCACCACCATG-GAGAAGGC-3' (SEQ ID NO:20) and 5'-GACGGACACATTGGGGGTAG-3' (SEQ ID NO:21) for GAPDH.

Statistical analysis. For comparison of treatment groups, unpaired t-tests (Mann-Whitney), paired t-tests, and one-way or two-way ANOVA (where appropriate) were performed. For ANOVA, Bonferroni post hoc analysis was used to compare treatment groups. All statistical analysis was performed using GraphPad Prism Software (version 4.01). Statistical significance was achieved when p<0.05.

Example 1

PGRN Binds to and Antagonizes Signaling by TNFα Receptors (TNFR)

Figure 8:
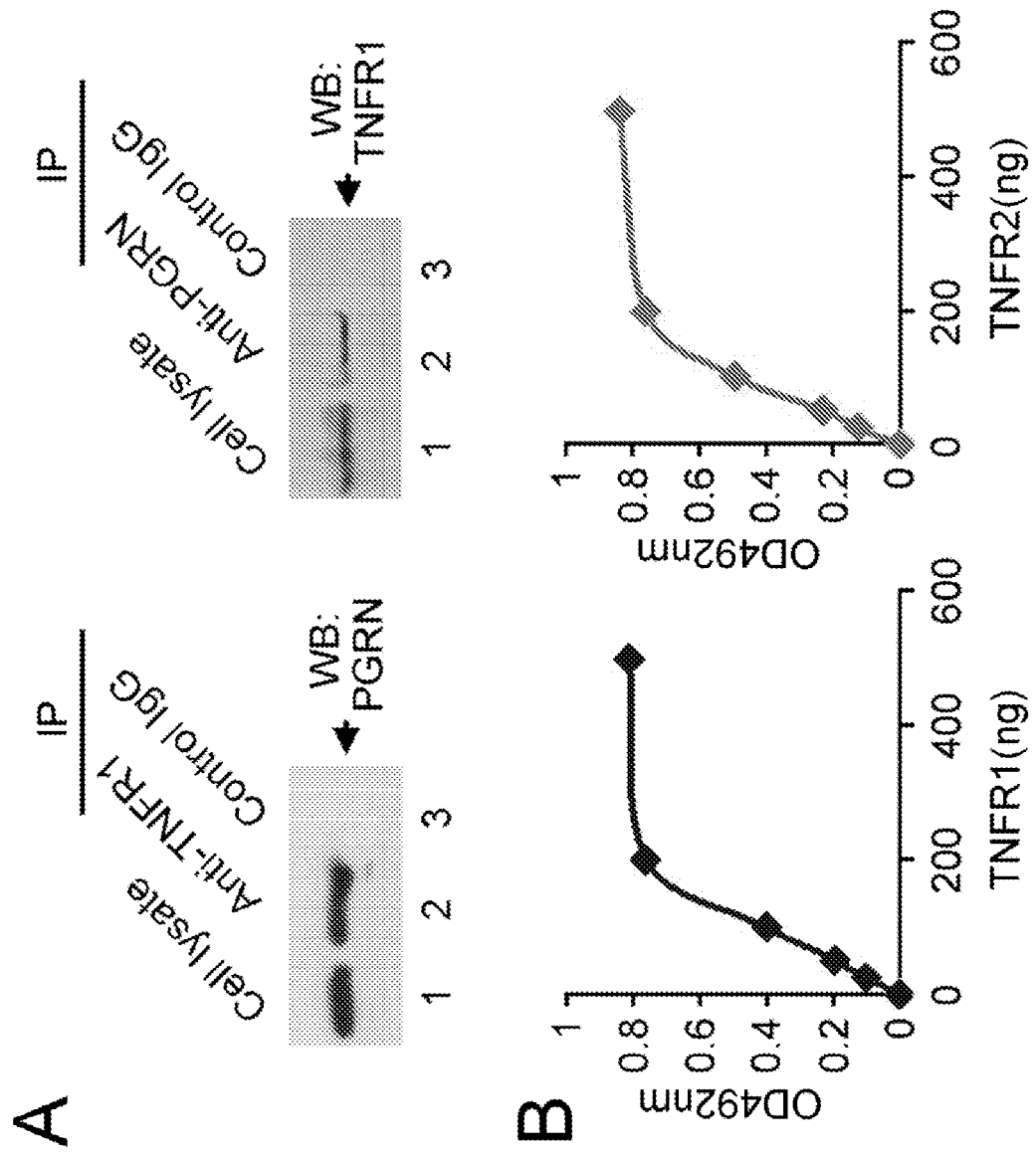
FIG. 8. (A) PGRN interacts with TNFR1 in chondrocytes (Co-IP assay). The cell lysates of human chondrocytes were incubated with anti-PGRN, anti-TNFR1, or control IgG antibodies, and bound protein was examined by Western blotting with the corresponding antibodies, as indicated. (B) PGRN directly binds to TNFR1 and TNFR2 (Solid phase binding). Microtiter plates were coated with 500 ng of rhPGRN in 100 μl of TBS buffer (50 mM Tris/HCl, 150 mM NaCl, pH 7.4). After blocking, various amounts (0-500 ng) of extracellular domain of TNFR1 (left) or extracellular domain of TNFR2 (right) were added to each well, and bound protein from the liquid phase was detected by antibody against TNFR1 or TNFR2, followed by a secondary antibody conjugated with horseradish peroxidase.

To identify PGRN-associated proteins, a yeast two-hybrid (Y2H) cDNA library was screened using the construct pDBleu-PGRN (aa 21-588) encoding PGRN lacking signal peptide as bait. Twelve positive clones were isolated among 2.5 millions clones screened. Sequencing data showed that two of them were cell surface TNFR2 (TNFRSF1B/CD120b). The interaction between PGRN and TNFR2 in yeast was then verified by repeating the Y2H assay. The interaction between PGRN and TNFR in human chondrocytes was demonstrated by co-immunoprecipitation (Co-IP) (FIG. 1A, FIG. 8A). Recombinant human PGRN (rhPGRN) demonstrated dose-dependent binding and saturation to liquid-phase the extracellular domains of TNFR1 and TNFR2 (FIG. 8B). Kinetic binding studies revealed that rhPGRN exhibited comparable binding affinity for TNFR1 and TNFR2 and had higher affinity for TNF receptors, especially TNFR2, when compared to TNFα (FIG. 1B).

Figure 9:
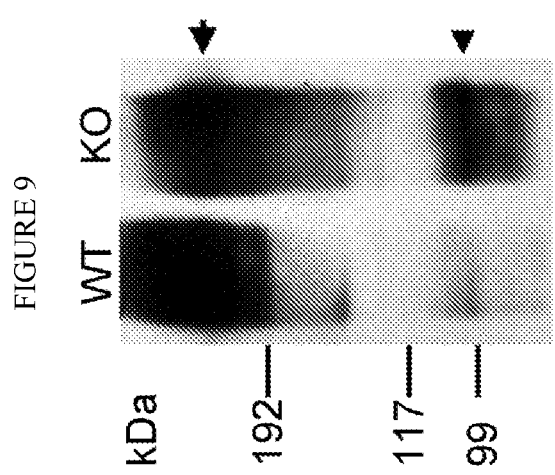
FIG. 9. PGRN deletion enhances TNF-induced COMP degradation. Cartilage explants isolated from wildtype (WT) and PGRN deficient (KO) mice were cultured in the presence of 5 ng/ml of TNF-α for 2 days. The media were separated on non-reduced SDS-PAGE gels and COMP was detected using an anti-COMP antibody. Intact COMP and COMP fragments are indicated by arrows and arrowheads, respectively.

The finding that PGRN directly binds to TNFR prompted a determination of whether PGRN affected the TNFα/TNFR interaction. rhPGRN demonstrated dose-dependent inhibition of TNFα binding to TNFR1 and TNFR2 (FIGS. 1, C and D), which suggested that PGRN may act as a physiological antagonist of TNFα signaling. Indeed, PGRN potently inhibits TNF-mediated neutrophil activation and cartilage degradation. Results showed a significant increase in TNFα-stimulated hydrogen peroxide in neutrophils and nitric oxide in bone marrow derived macrophages (BMDMs) from PGRN-deficient mice (FIGS. 1, E and F). It has been previously showed that TNFα induces the degradation of COMP, a prominent noncollagenous component of cartilage that plays an important role in stabilizing the cartilage matrix and is heavily degraded in both osteoarthritis and rheumatoid arthritis. Current results showed that deletion of PGRN results in a marked increase in TNFα-induced COMP degradation (FIG. 9).

Figure 10:
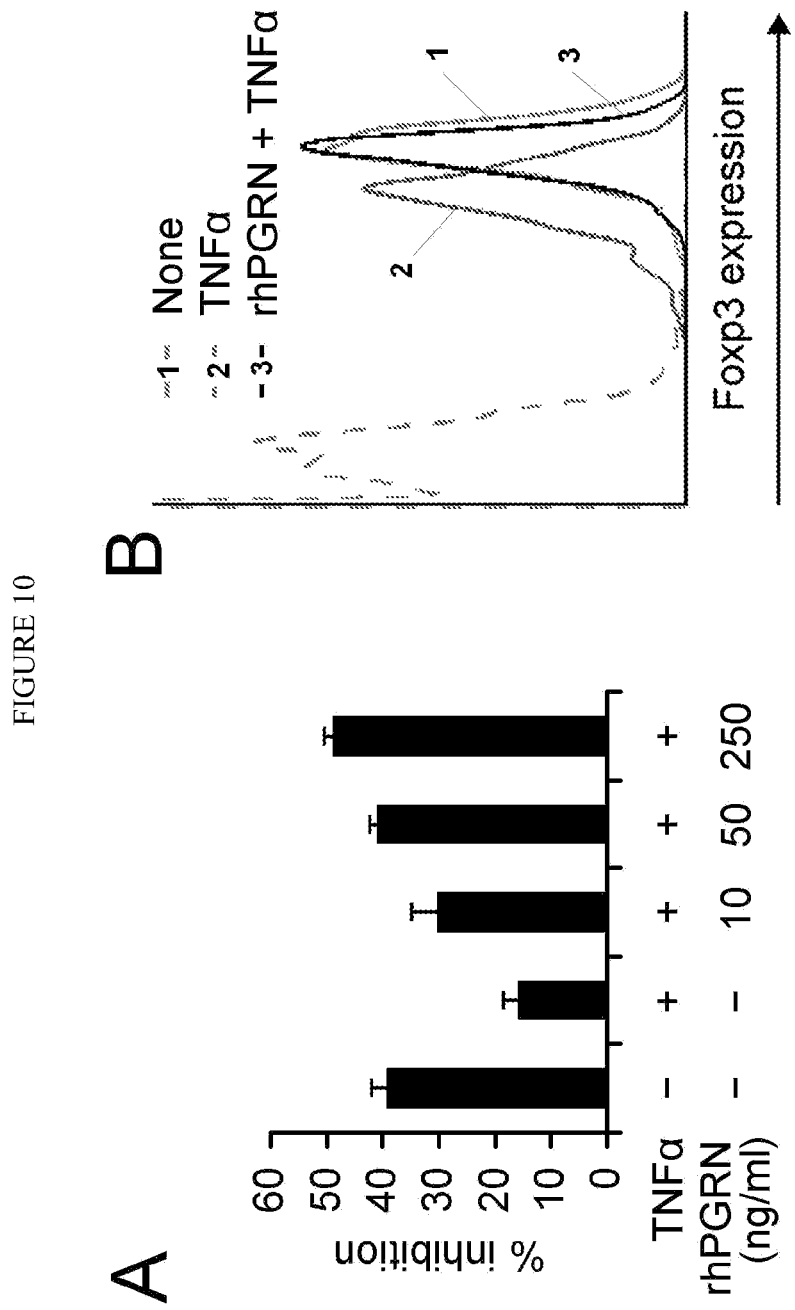
FIG. 10. PGRN overcomes TNFα downregulation of Treg suppressive function and prevents TNFα-induced downregulation of Foxp3 expression in Treg cells. (A) PGRN overcomes TNFα downregulation of Treg suppressive function. Freshly purified human CD4$^+$CD25 T cells (Treg) were pre-treated with indicated concentrations of PGRN before adding TNFα (50 ng/ml), mixed with CD4$^+$CD25$^-$T cells (Teff) at ratio 1:3, and plated on immobilized CD3 monoclonal antibody (mAb). Cytokine secretion was determined by ELISA by using Human IFNγ Cytoset™. Data represent the average of three independent experiments. Values are mean±s.d. (B) PGRN prevents TNFα-induced down-regulation of Foxp3 expression in Treg cells. Freshly purified Treg cells were pre-treated with PGRN (250 ng/ml) for 30 min before adding TNFα (50 ng/ml). Foxp3 expression was determined by FACS after 18 hours. Representative experiment of two is shown.
Figure 11:
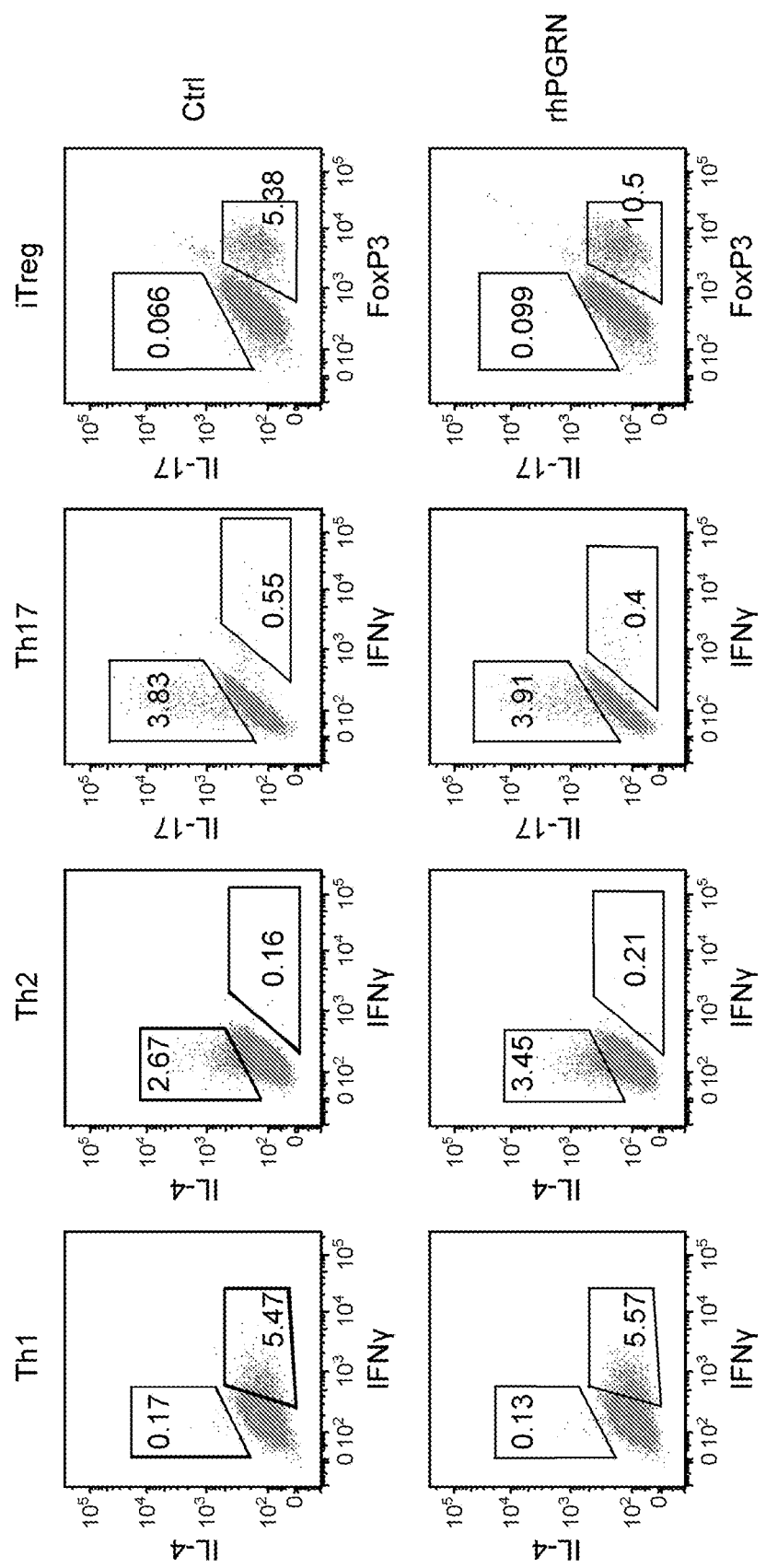
FIG. 11. PGRN promotes Treg differentiation. Naïve CD4$^+$ T cells were enriched by CD4 T cell negative selection kit combined with addition of Bio-anti CD-25 and Bio-anti-CD44 for depleting CD25$^+$ regulatory T cells and CD44$^{hi}$ activated cells. Cells were activated by coated anti-CD3 and soluble anti-CD28 for Th1 (anti-IL-4, 10 μg/ml; IL-12, 10 ng/ml), Th2 (anti-IFNγ, 10 μg/ml; anti-IL-12, 10 μg/ml; IL-4, 20 ng/ml), Th17 (anti-IFNγ, 10 μg/ml; anti-IL-12, 10 μg/ml; anti-IL-4, 10 μg/ml; IL-6, 20 ng/ml; TGFβ, 1 ng/ml), and Treg (anti-IFNγ, 10 μg/ml; anti-IL-12, 10 μg/ml; anti-IL-4, 10 μg/ml; IL-2, 2 ng/ml; TGFβ, 2.5 ng/ml) in the absence (Ctrl) or presence (rhPGRN) of 100 ng/ml of rhPGRN polarization for 5 days. After re-stimulation with PMA and ionomycin in the presence of Golgi plug for 4 hours, cell surface staining was performed with anti-CD4 followed by intracellular cytokine staining for IL-4, IFNγ, IL-17 and FoxP3.
Figure 12:
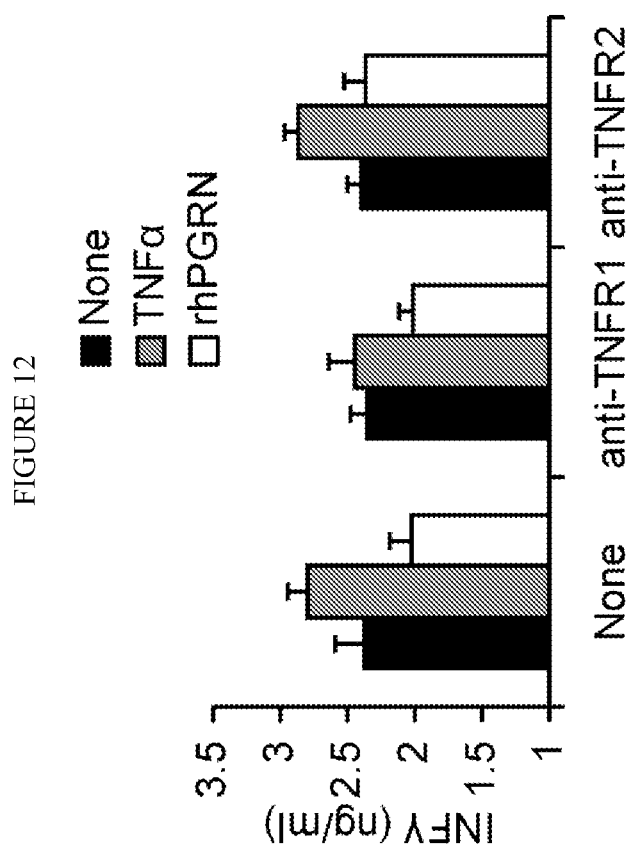
FIG. 12. PGRN inhibits, whereas TNFα stimulates, IFNγ production in Teff cells in a TNFR-dependent manner. Teff cells were purified from the peripheral blood of human donors and pre-treated cells with 2 μg/ml of either anti-TNFR1 or anti-TNFR2 antibodies for 1 hour before adding TNFα (50 ng/ml) or rhPGN (250 ng/ml). Then, the cells were plated on anti-CD3 mAb (5 mg/ml) and cultured for 24 hr. Cytokine secretion was determined by ELISA by using Human IFNγCytoset™. Average of two different experiments is shown.

In order to determine whether PGRN affects TNFα signaling in human cells, the effects of treating human regulatory T cells (Treg; phenotypically TNFR2+ TNFR1−) with PGRN was examined. It was hypothesized that such treatment may protect Treg cells from negative regulation by TNFα. PGRN protected Treg from a negative regulation by TNFα (FIG. 10) and promoted the differentiation of Treg from naïve T cells (FIG. 11). Furthermore, TNFα up-regulated, whereas PGRN down-regulated interferon (IFN)-γ secretion in effector T cells (Teff) (FIG. 12). TNFR1 blocking antibodies largely inhibited TNFα-induced upregulation of IFNγ secretion, but did not affect PGRN-mediated suppression; in contrast, TNFR2 blocking antibodies abolished PGRN-mediated downregulation of IFNγ production (FIG. 12). These data indicate that the regulation of TNFα and PGRN on Teff cells primarily depend on TNFR1 and TNFR2, respectively.

This example shows that recombinant human PGRN is useful in methods for inhibition of TNFα signaling mediated by TNFR1 and TNFR2, such as, for example in the treatment or prevention of conditions caused by or resulting in TNFα signaling.

Example 2

Figure 2:
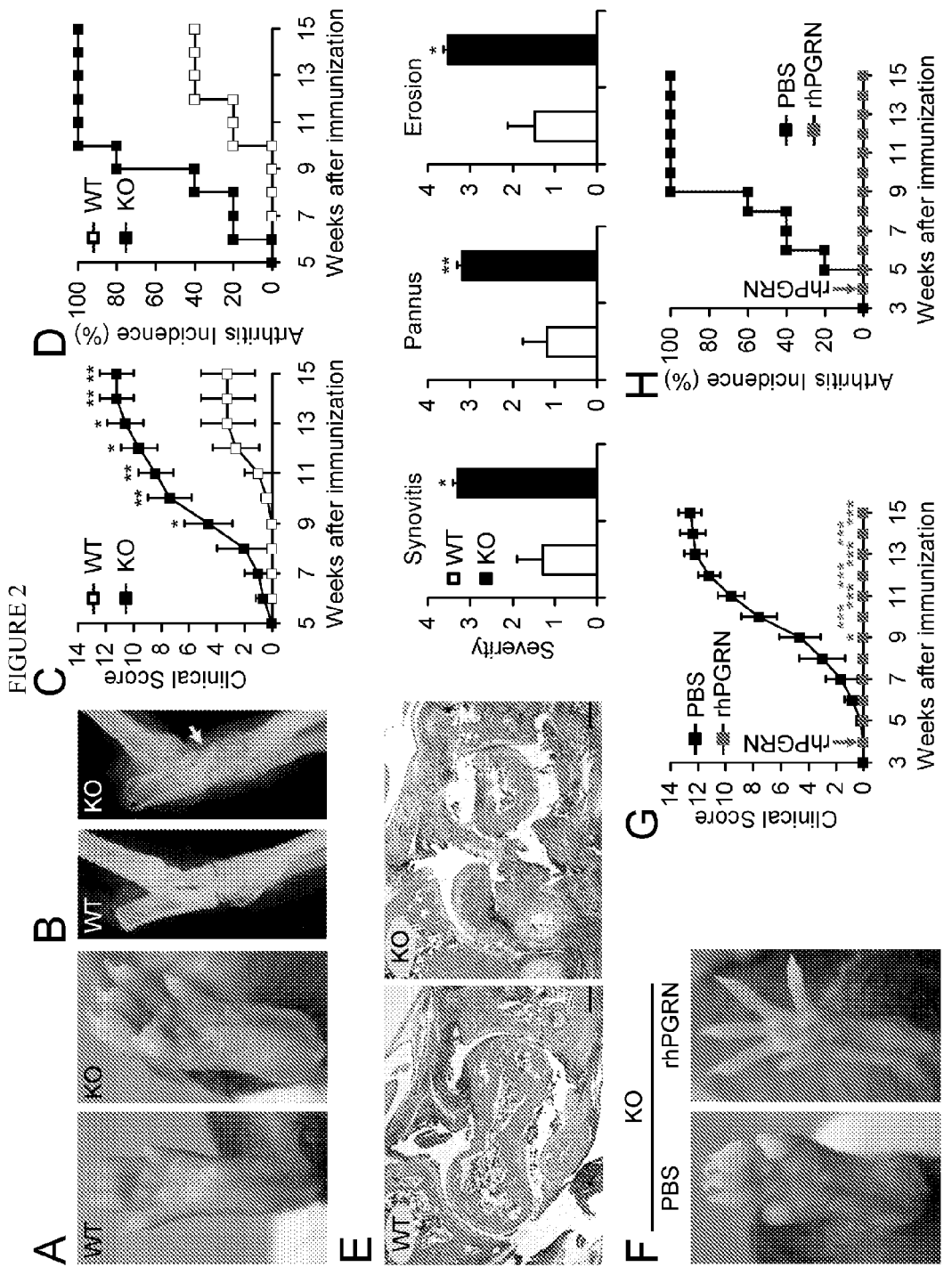
FIG. 2. PGRN-deficient mice are highly susceptible to collagen-induced arthritis, and administration of PGRN reverses the severe inflammatory arthritis seen in collagen-challenged PGRN-deficient mice. (A) Paws of wild type (WT) and Grn$^{-/-}$ (KO) mice derived from C57BL/6 (n=10/group) immunized with collagen II for 15 weeks. (B) Radiography of ankle joints of WT and KO collagen II-immunized mice. Arrow indicates areas of severe joint destruction in PGRN-deficient CIA mice. (C) Clinical arthritis scores in WT and KO mice with CIA. The data are presented as the mean clinical score±s.e.m. *$P<0.05$, **$P<0.01$ versus the control WT group. (D) Incidence of arthritis in the indicated groups. (E) H&E stained sections and evaluation of synovitis, pannus and erosion of ankle joints in WT and KO mice with CIA 15 weeks following primary immunization. Scale bar, 200 µm. Values are mean±s.d. *$P<0.05$, $P<0.01$ versus the control WT group. (F) Paws of KO mice treated with PBS or rhPGRN from 4 to 15 weeks following collagen II immunization. (G) Clinical arthritis scores in KO mice with CIA treated with PBS or rhPGRN (n=10/group). Data are presented as the mean clinical score±s.e.m. $P<0.01$, ***$P<0.001$ versus the control PBS group. (H) Incidence of arthritis in each experimental group.
Figure 13:
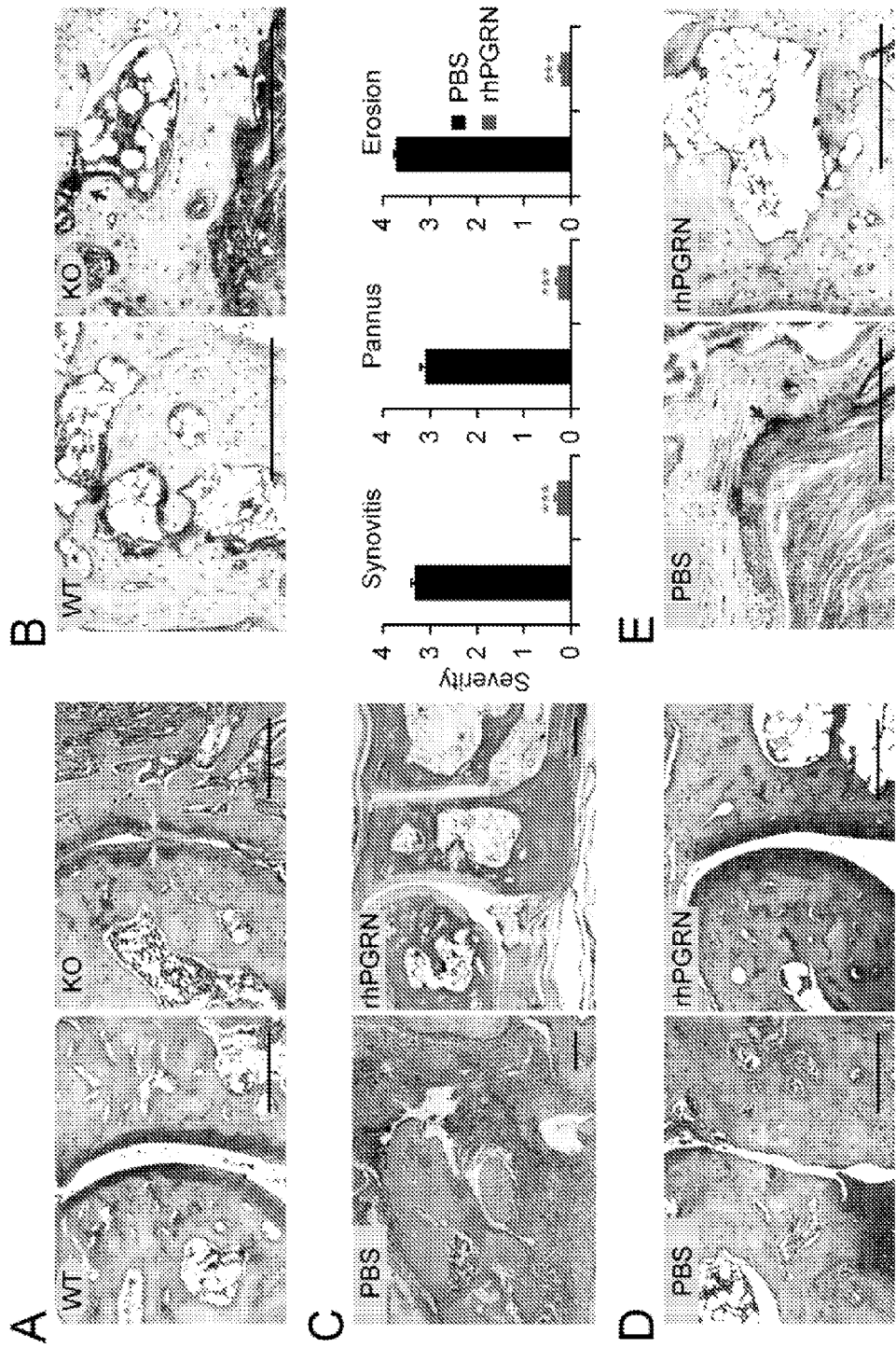
FIG. 13. PGRN-deficiency increases, whereas recombinant PGRN prevents, loss of cartilage matrix, tissue destruction, and osteoclast activity in collagen-induced arthritis (CIA) model. (A) Safranin O stained sections of tarsal joints from each experimental group. Arrows indicate loss of matrix staining Scale bar, 200 μm. (B) TRAP stained sections of tarsal bones in WT and KO mice with CIA. TRAP osteoclasts are indicated by arrows. Scale bar, 200 μm. (C) H&E stained sections and histological evaluation of ankle joints in KO mice with CIA treated with PBS or rhPGRN. Scale bar, 200 μm. Values are mean±s.d. ***P<0.001 versus the control PBS group. (D) Safranin O stained sections of tarsal joints from PGRN deficient CIA mice treated with PBS or rhPGRN. Arrows indicate loss of matrix staining Scale bar, 200 μm. (E) TRAP stained sections of tarsal bones in PGRN deficient CIA mice treated with PBS or rhPGRN. TRAP osteoclasts are indicated by arrows. Scale bar, 200 μm.

Recombinant Human PGRN Reduces TNFα-Mediated Inflammation Associated with Collagen-Induced Arthritis (CIA) in PGRN-Deficient Mice The role of endogenous PGRN during inflammation in vivo was examined with respect to the clinical and histopathological features of PGRN-deficient C57BL/6 mice (Grn−/−) in the context of collagen-induced arthritis (CIA), which shares both immunological and pathological features with human rheumatoid arthritis. Gm−/− mice developed more severe inflammatory arthritis and increased bone and joint destruction as compared with their control littermates (FIGS. 2, A and B). Results showed a significant increase in the arthritis severity score (FIG. 2C), a reduced time to disease onset and a greater incidence of arthritis in Grn−/− mice compared to control mice (FIG. 2D). Histological and quantitative analysis of whole ankle joints demonstrated a significant increase in synovitis, pannus formation, and destruction of bone and cartilage in Grn−/− mice, compared with controls (FIG. 2E). Other hallmarks of arthritis, such as loss of matrix staining in the articular cartilage and an increase in bone-resorbing osteoclasts, were exacerbated in Grn−/− mice (FIGS. 13, A and B).

To determine whether the inflammatory arthritis of collagen II-challenged PGRN-deficient mice can be neutralized by PGRN, rhPGRN was administered to PGRN-deficient CIA mice for 11 weeks. Results showed that administration of rhPGRN completely blocked the progression of CIA (FIG. 2F). No visible symptoms of CIA were observed in any individual mouse, with all PGRN-deficient subjects administered rhPGRN showing 0% incidence and an arthritis score of zero (FIGS. 2, G and H). Administration of rhPGRN also significantly inhibited synovitis, pannus formation, tissue destruction (FIG. 13C), and the loss of cartilage matrix (FIG. 13D). Notably, the number of osteoclasts was reduced in PGRN-deficient mice treated with rhPGRN when compared to untreated PGRN-deficient mice (FIG. 13E). Collectively, these data demonstrate that the loss of PGRN expression in vivo results in enhanced susceptibility to collagen induced arthritis, which can be entirely reversed by the administration of recombinant PGRN.

This example shows that recombinant human PGRN is useful in methods for inhibition of TNFα signaling mediated by TNFR1 and TNFR2, such as, for example in the treatment or prevention of conditions caused by or resulting in TNFα signaling. In particular, the example shows that recombinant human PGRN is useful in methods for reducing TNFα-mediated arthritic inflammation in subjects in need thereof.

Example 3

Recombinant Human PGRN Reduces Arthritic Inflammation in TNFα Transgenic Mice

Figure 3:
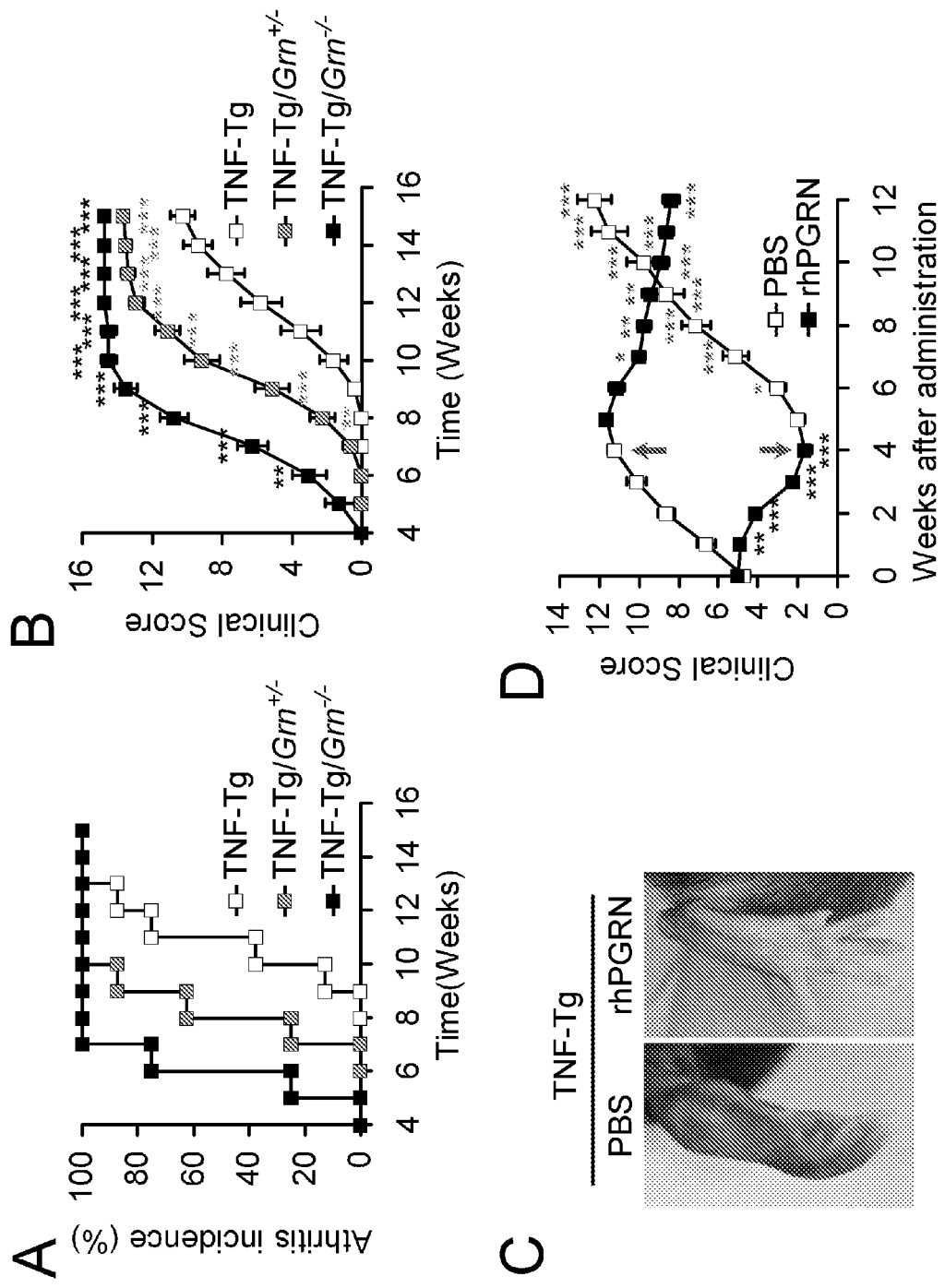
FIG. 3. Deletion of PGRN exacerbates, whereas recombinant PGRN prevents, the spontaneous development of inflammatory arthritis in TNF transgenic mice. (A) Incidence of arthritis in TNF-Tg, TNF-Tg/Grn$^{+/-}$, and TNF-Tg/Grn$^{-/-}$, mice (n=8/group). (B) Clinical arthritis scores. Data are presented as the mean clinical score±s.e.m. *$P<0.05$, $P<0.01$ and *$P<0.001$ versus the control TNF-Tg group. (C) Photographs of paws of TNF-Tg mice with mild arthritis treated with either PBS or rhPGRN for 4 weeks. (D) Effect of PGRN in TNF-Tg mice. TNF-Tg mice with established mild arthritis (Clinical score is around 5) were treated with PBS or rhPGRN (n=8/group). The treatment type was then switched between the two groups, and the switch time point is indicated with arrows. Development of arthritis was then scored. The data are presented as the mean clinical score±s.e.m. The statistics were compared between untreated (PBS) and rhPGRN-treated group before the switch time point (black star). After that statistics were compared to the switch time point in each group (green star). *$P<0.05$, $P<0.01$, *$P<0.001$.
Figure 14:
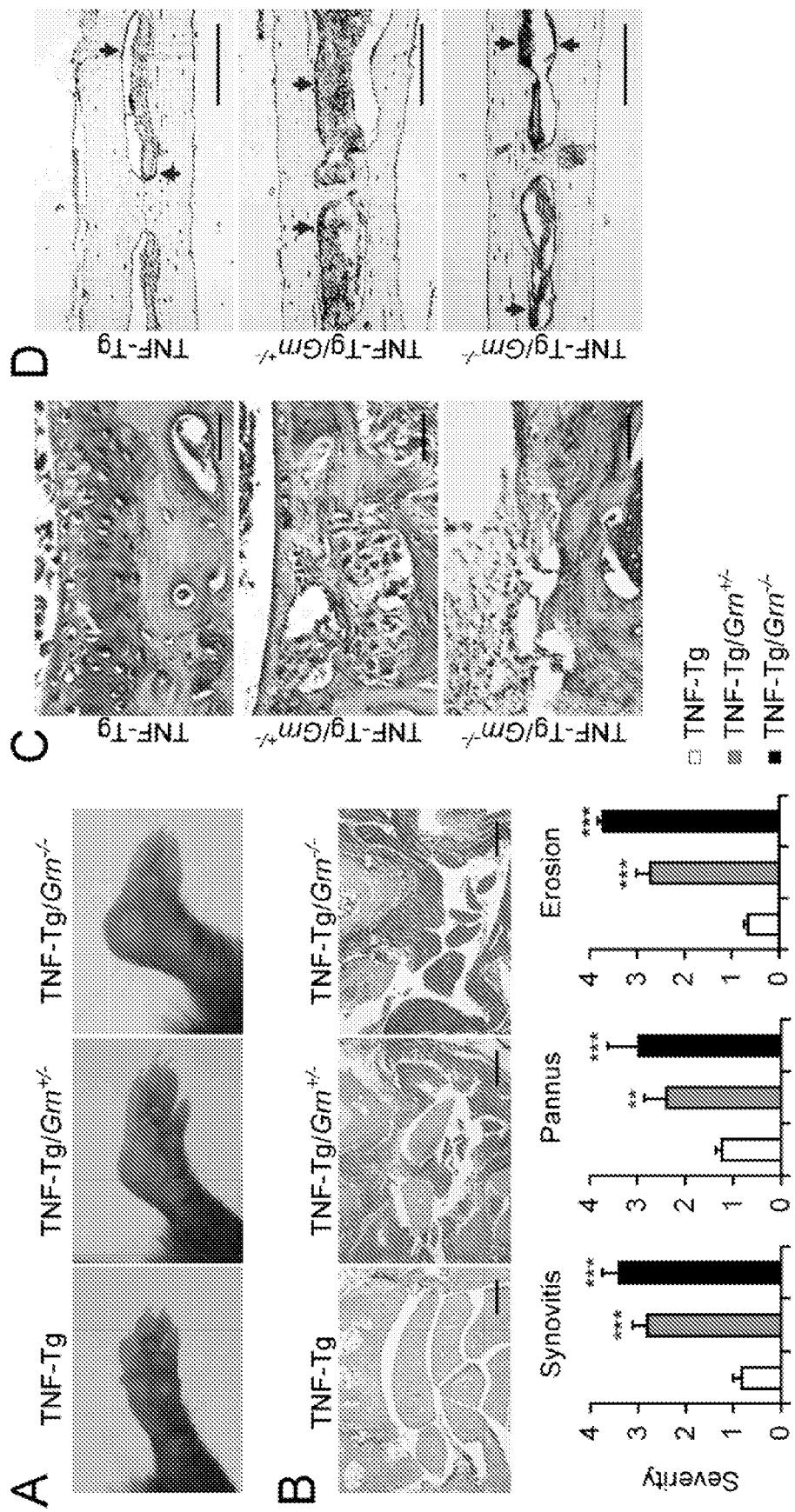
FIG. 14. Deletion of PGRN increases joint deformation, tissue destruction, loss of cartilage matrix and calvarial osteoclast activity in TNF transgenic mice. (A) Photographs of frontal paws of 12-week-old TNF-Tg, TNF-Tg/Grn$^{+/-}$, and TNF-Tg/Grn$^{-/-}$ mice. (B) H&E stained sections and histological evaluation of wrist joints in TNF-Tg, TNF-Tg/Grn$^{+/-}$, and TNF-Tg/Grn$^{-/-}$ mice. Scale bar, 200 μm. Values are mean±s.d. ***P<0.001 versus the control TNF-Tg group. (C) Safranin O stained sections of wrist joints in 12 week old mice from each experimental group. Arrows indicate loss of matrix staining Scale bar, 50 μm. (D) TRAP stained sections of calvaria from 12 week old TNF-Tg, TNF-Tg/Grn$^{+/-}$, and TNF-Tg/Grn$^{-/-}$ mice. TRAP osteoclasts are indicated by arrows. Scale bar, 200 μm.

To determine whether the anti-inflammatory actions of PGRN occur through the suppression of TNFα signaling in vivo, the gene encoding PGRN was deleted in mice expressing a human TNFα transgene (TNF-Tg). TNF-Tg mice develop an inflammatory arthritis phenotype spontaneously. Results showed that the deletion of PGRN hastened the onset of arthritis and resulted in a worse clinical score in a gene dosage-dependent manner (FIGS. 3, A and B). 1-week-old TNF-Tg/Gm−/− and TNF-Tg/Grn+/− mice developed severe swelling and joint deformation (FIG. 14A), significantly increased synovitis, pannus formation, destruction of the wrist joints (FIG. 14B), and loss of cartilage matrix (FIG. 14C). Overexpression of TNFα resulted in prominent calvarial osteoclast activity of TNF-Tg mice, and deletion of PGRN further enhanced this activity (FIG. 14D). These results demonstrate that PGRN may also be a negative regulator of TNFα-induced osteoclastogenesis and a mediator of bone integrity during the inflammatory process.

To determine the therapeutic effects of PGRN in TNF-Tg mice, rhPGRN was administered to TNF-Tg mice with established mild arthritis. Treatment with rhPGRN resulted in the elimination of any visual signs of arthritis (FIG. 3C) and a reduced arthritis severity score (FIG. 3D). To confirm that these effects were due to the inhibitory effects of PGRN, rhPGRN administration was discontinued, and the TNF-Tg mice evaluated for signs of arthritis. At 7 days after the cessation of rhPGRN treatment, signs of arthritis began to develop (FIG. 3D). In contrast, application of rhPGRN to TNF-Tg mice in the phosphate buffered saline (PBS)-treated group resulted in a marked reduction of severe arthritis signs.

Taken together, these data demonstrate that PGRN may exert its anti-inflammatory effects through inhibition of TNF/TNFR signaling in vivo.

This example shows that recombinant human PGRN is useful in methods for inhibition of TNFα signaling mediated by TNFR1 and TNFR2, such as, for example in the treatment or prevention of conditions caused by or resulting in TNFα signaling. In particular, the example shows that recombinant human PGRN is useful in methods for reducing TNFα-mediated arthritic inflammation in subjects in need thereof.

Example 4

Structure-Function Analysis of PGRN

Figure 15:
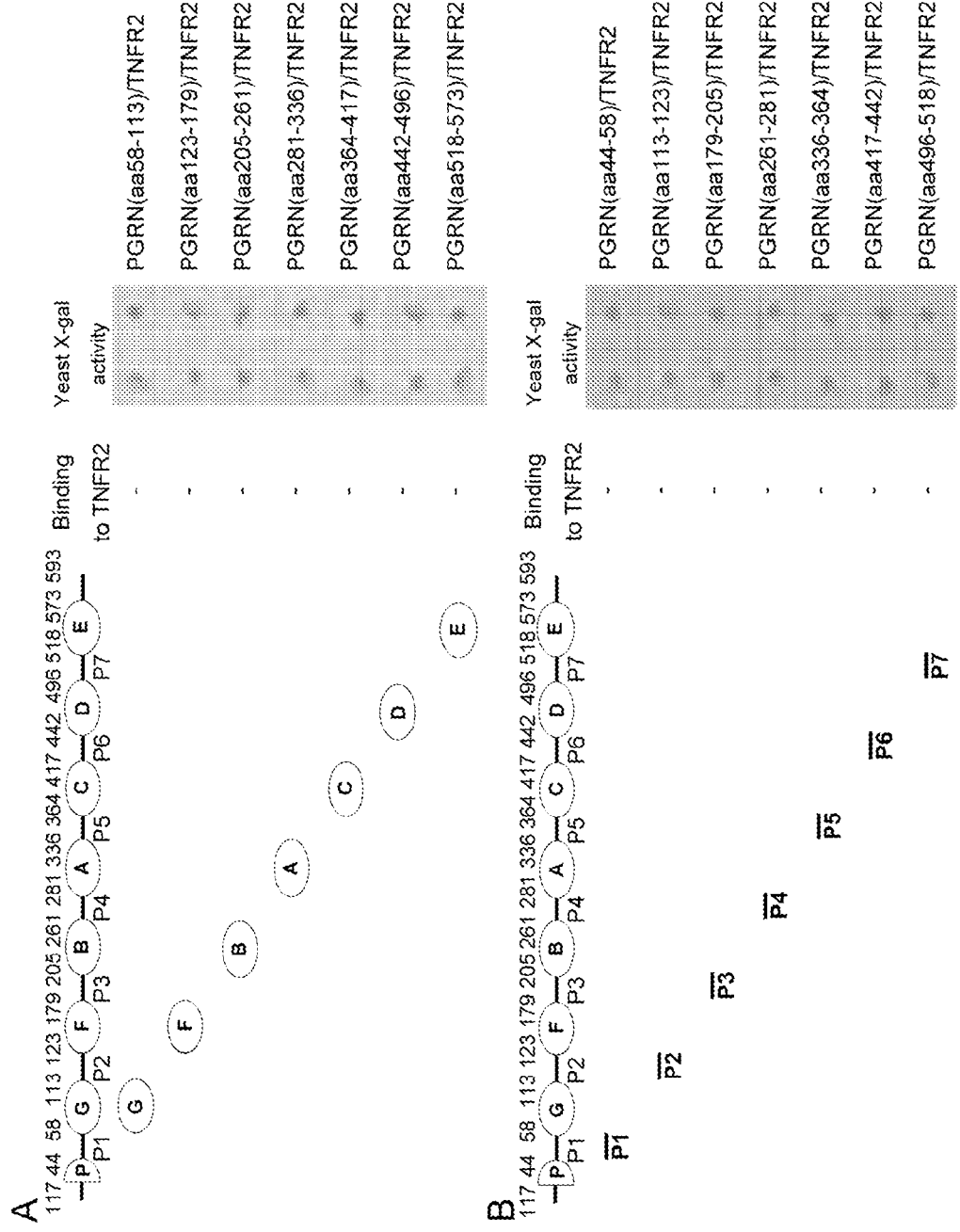
FIG. 15. No single granulin unit (A, B, C, D, E, F, or G) (A) or linker region (P1, P2, P3, P4, P5, P6 or P7) (B) is able to bind to TNFR2. (Left) Schematic diagram of PGRN constructs used to map those of its fragments that bind to TNFR2. (Right) β-Galactosidase assays.

The domains of PGRN required for its interaction with TNF receptors were identified using a Y2H assay. Results showed that no single granulin unit (FIG. 15A) or linker region (FIG. 15B) was able to bind to TNFR2, suggesting that the binding domain of PGRN may span granulin unit and linker.

Figure 16:
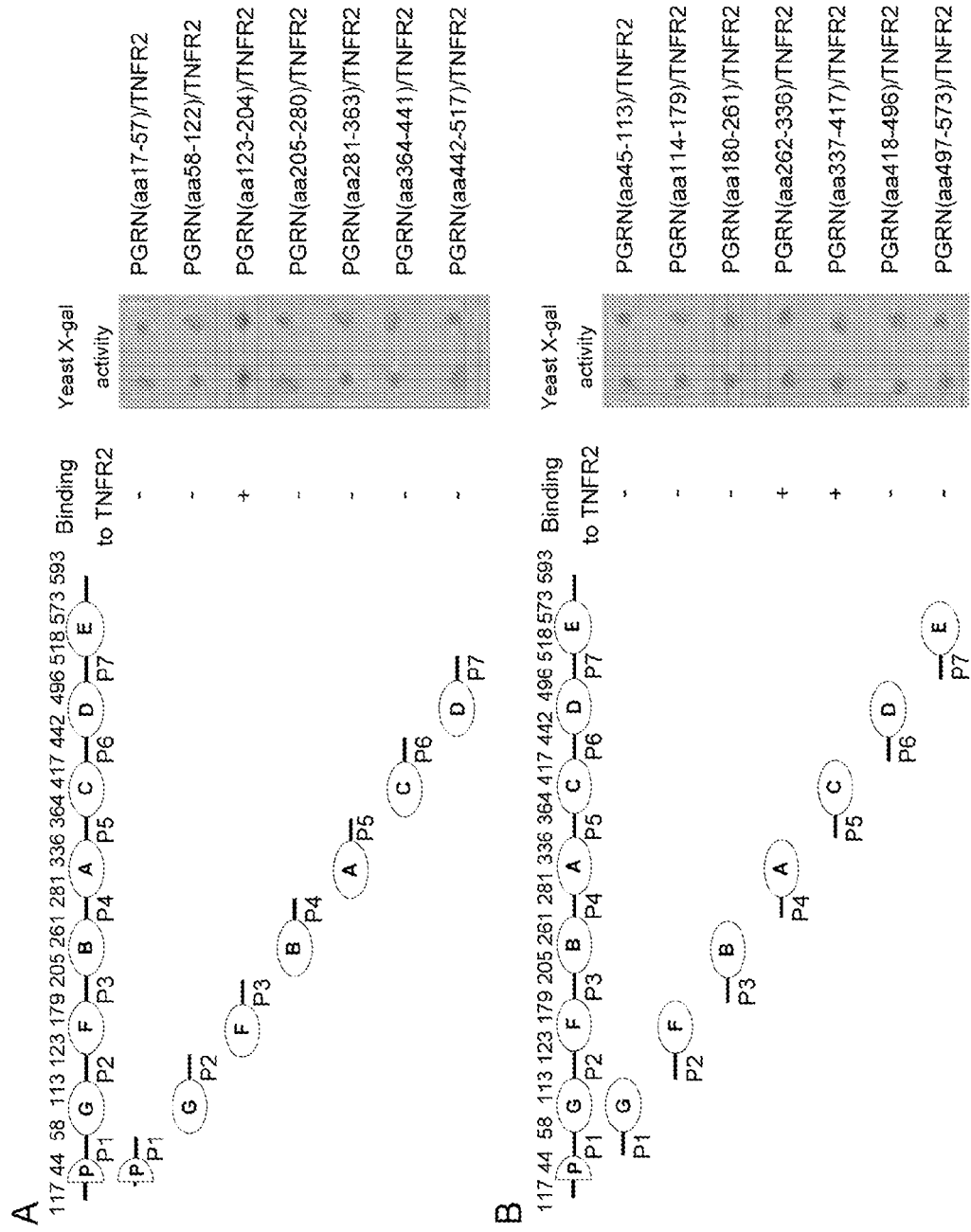
FIG. 16. Granulin F—P3 (A), P4-granulin A and P5-granulin C (B) exhibit a weak interaction with TNFR2. (Left) Schematic diagram of PGRN constructs used to map those of its fragments that bind to TNFR2. (Right) β-Galactosidase assays.
Figure 17:
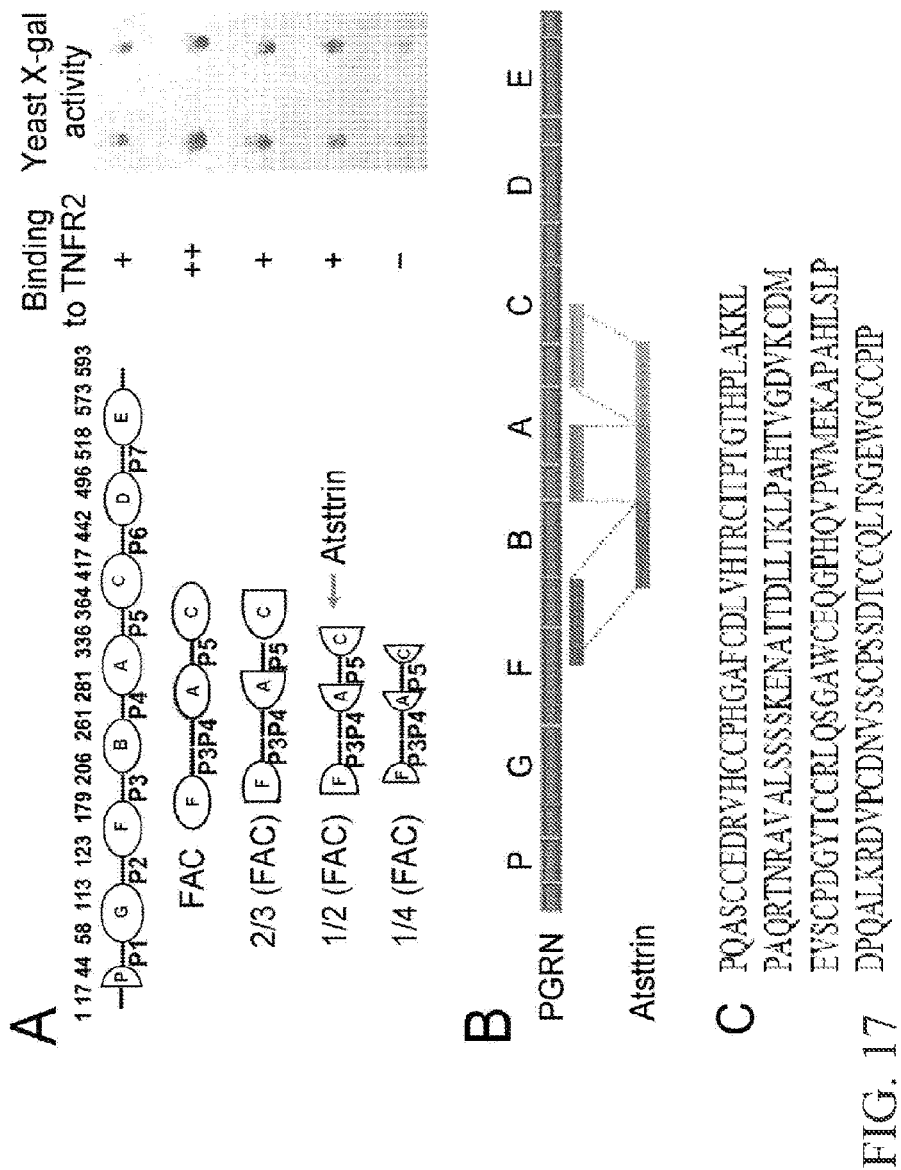
FIG. 17. Schematic diagrams showing Atsttrin-al composition and identification by Y2H assay. (A) Identification of Atsttrin-α1 (Y2H assay). (Left) Schematic diagram of PGRN constructs used to map those of its fragments that bind to TNFR2. (Right) β-Galactosidase assays. (B) Schematic of Atsttrin-al composition. Three fragments derived from PGRN are indicated with three different colors. (C) Amino acid sequence of Atsttrin-α1 (SEQ ID NO: 4).

In the first round of screening, each granulin unit was expressed with its immediately adjacent downstream or upstream linker. Binding to TNFR2 was observed for three peptides only, consisting of granulin F-P3, P4-granulin A, and P5-granulin C (FIGS. 16, A and B). In the next round of screening, these three peptides were joined to generate a non-native peptide referred to as FAC (FIG. 17A). The FAC peptide exhibited a stronger binding affinity for TNFR2 than PGRN. Granulin units F, A, and C are known to be the granulin domains most capable of independent folding, and each of domain has N- and C-terminal subdomains that are structurally independent. By deleting portions of each of the granulin domains of FAC, it was demonstrated that a version comprising half of each of granulin units F, A, and C, with linkers P3, P4, and P5 retains binding specificity to TNFR2 (FIG. 17). This molecule is referred to as Atsttrin-α1 (Antagonist of TNF/TNFR Signaling via Targeting to TNF Receptors-α1). The naming convention derives from the fact that the peptide is a variant of Atsttrin-α, which has been previously described.

This example shows that the Atsttrin-α1 peptide is useful in methods comprising binding to TNFR2 and inhibition of TNFR2 or TNFα signaling, such as, for example, in the treatment or prevention of conditions caused by or resulting in TNFα or TNFR2 signaling.

Example 5

Characterization of Atsttrin-α1 Binding Specificity and TNFα Inhibition

Figure 4:
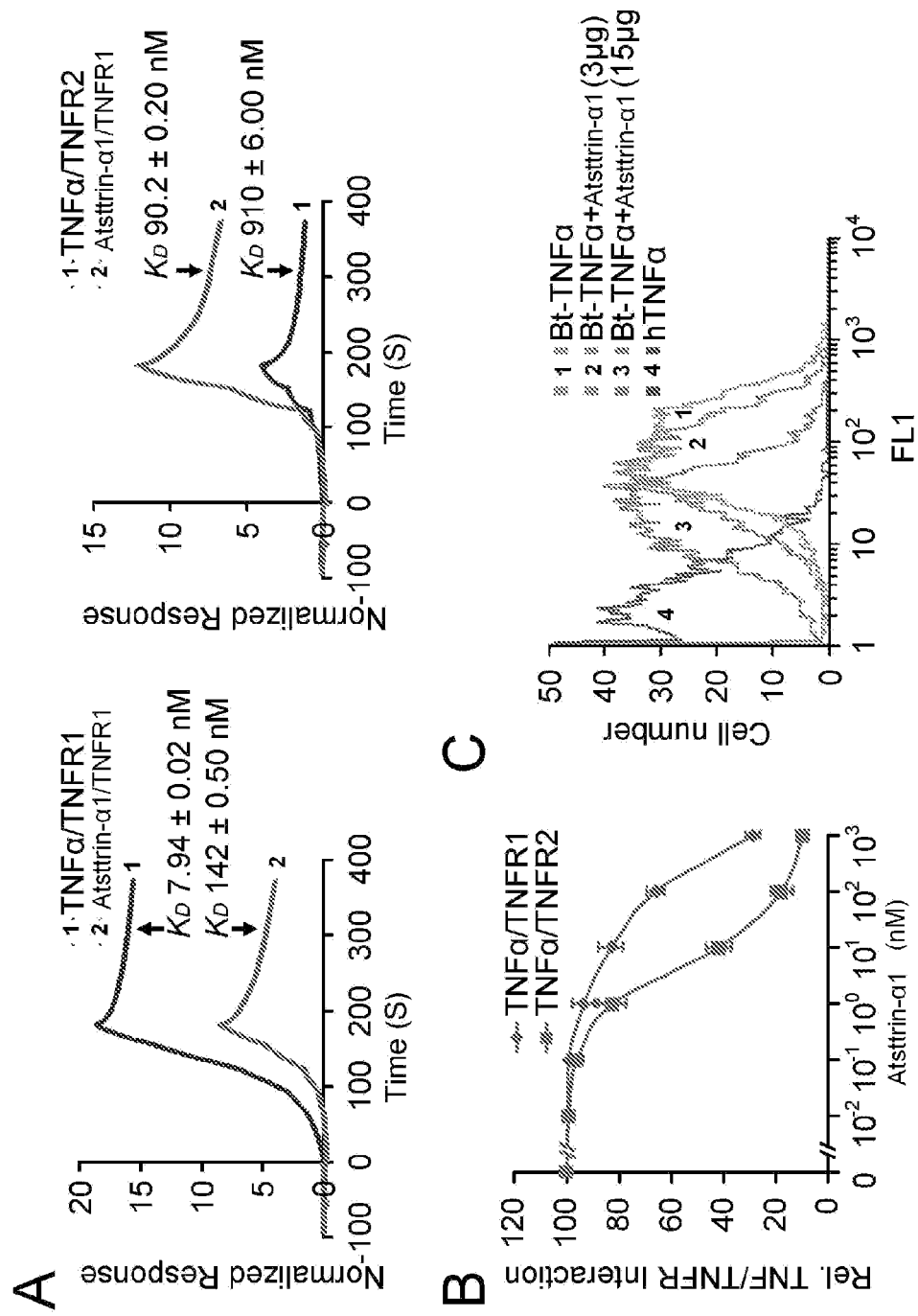
FIG. 4. Atsttrin-α1 exhibits selective TNFR binding and inhibits TNFα/TNFR interactions. (A) FastStep™ Kinetic Assay for binding of Atsttrin-α1 and TNFα to TNFR1 and TNFR2. Samples were injected using FastStep™ injection, and dissociation of analyte-ligand complexes was monitored. $K_D$ for each interaction was indicated. (B) Atsttrin-α1 inhibits the binding of TNFα to TNFR1 and TNFR2 (solid phase binding). Microtiter plate coated with TNFα was incubated with TNFR1 or TNFR2 in the presence of various amounts of Atsttrin-α1, and the bound TNFR to TNFα was detected by corresponding antibodies. Values are mean±s.d. (C) Flow cytometric analysis of Raw264.7 cells after staining with 50 ng biotinylated human TNFα (Bt-TNFα) in the presence of different doses of Atsttrin-α1.
Figure 18:
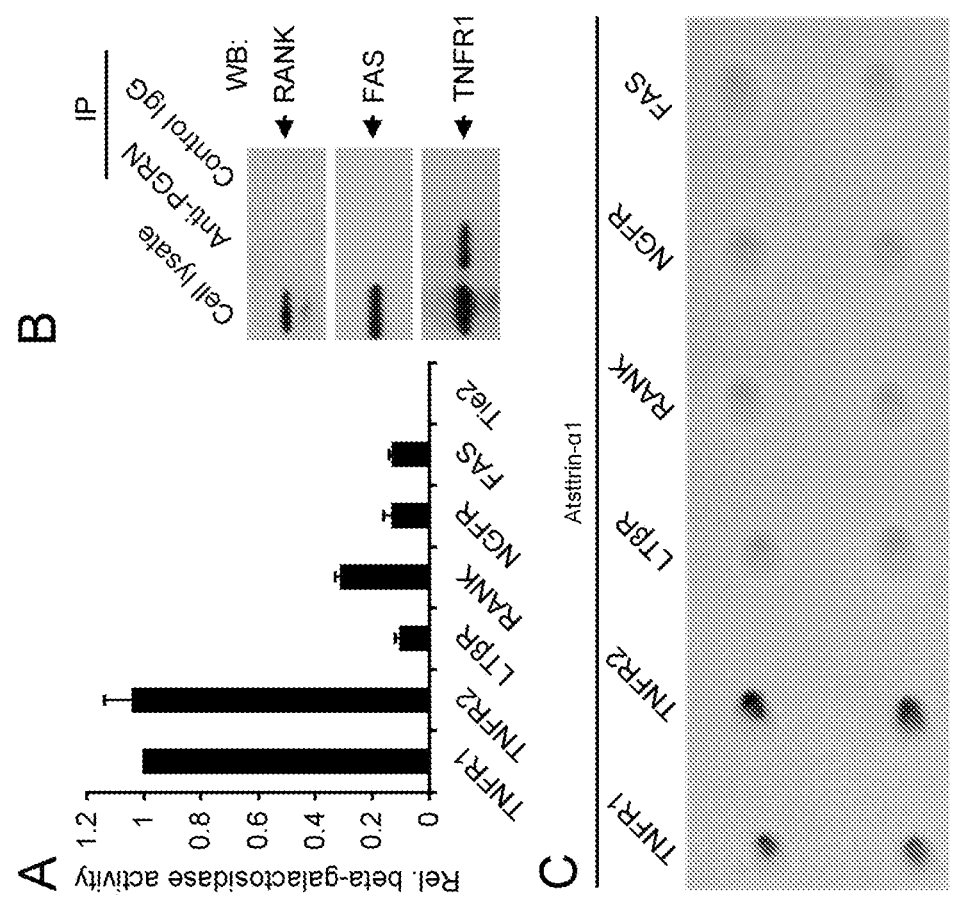
FIG. 18. PGRN interacts with the TNFR subfamily. (A) Quantification of protein-protein interactions between PGRN and TNFR subfamily were determined using the β-galactosidase (β-gal) liquid assay. The plasmid encoding one of the members in TNFR subfamily (as indicated) linked to VP16AD, and the plasmid encoding PGRN linked to Ga14DBD were co-transformed into yeast strain MAV203. The β-gal activity represents the average of three transformants from three independent experiments. The β-gal activity produced by the association of PGRN with TNFR1 was set to 1. Tie2 receptor was used as a negative control. Values are mean±s.d. (B) Co-IP assay. The cell lysates of RAW264.7 cells were immunoprecipitated (IP) with control IgG or anti-PGRN antibodies, and bound protein was examined by Western blotting (WB) with the corresponding antibodies, as indicated. The interaction of PGRN/TNFR1 is employed as a positive control. (C) Atsttrin-α1 specifically binds to TNFR1 and TNFR2. The plasmid encoding one of the members in TNFR subfamily (as indicated) linked to VP16AD, and the plasmid encoding Atsttrin-α1 linked to Ga14DBD were co-transformed into yeast strain MAV203. Yeast transformants were examined for β-galactosidase activity.
Figure 19:
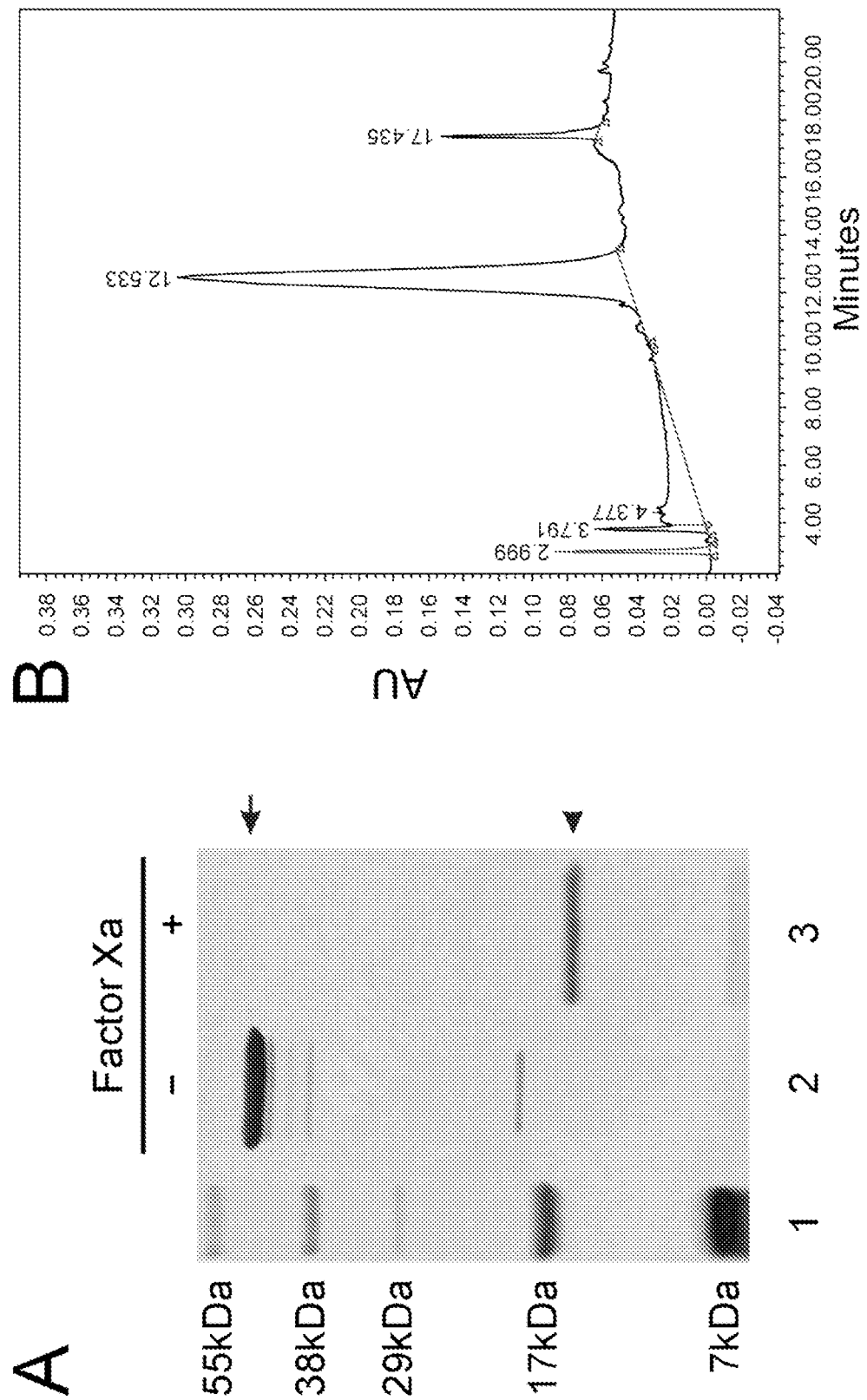
FIG. 19. Characterization of recombinant Atsttrin-α1. (A) SDS-PAGE analysis. GST-Atsttrin-α1 and Atsttrin-α1 are indicated by arrows and arrowheads, respectively. (B) Reverse HPLC analysis. The reverse-phase HPLC was performed at 25° C. using a Waters 2695 HPLC Module equipped with Waters 2487 dual absorbance detector. An Analytical C18 HPLC column was employed. 35 μl of sample at 10 μM concentration was injected. Sample was separated over a gradient of 0-60% acetonitrile in the presence of 0.08% TFA at a flow rate of 0.8 ml/min.
Figure 20:
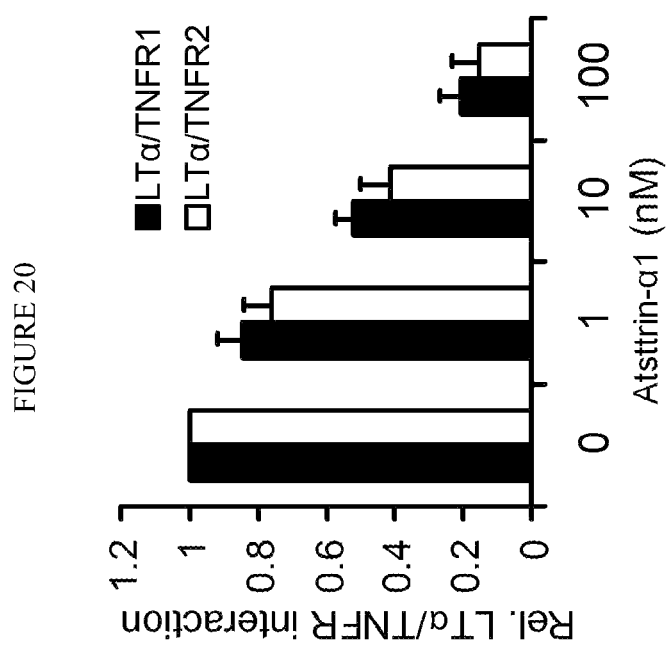
FIG. 20. Atsttrin-α1 inhibits the binding of LTα to TNFR1 and TNFR2 (solid phase binding). Microtiter plate coated with lymphotoxin-α (LTα) was incubated with TNFR1 or TNFR2 in the presence of various amounts of Atsttrin-α1, as indicated, and the bound TNFR to LTα was detected by corresponding antibodies. The interaction between LTα and TNFR in the absence of Atsttrin-α1 was set as 1. Values are mean±s.d.

It was demonstrated by Y2H assay that PGRN associated weakly with other members of TNFR subfamily, whereas Atsttrin-α1 selectively interacted with TNFR1 and TNFR2 (FIG. 18). Atsttrin-α1 was expressed in bacteria as a GST fusion protein, purified on glutathione agarose resin, and eluted using Xa factor (there is a Xa factor cleavage site between GST and Atsttrin-α1) (FIG. 19A). Reverse phase HPLC showed high purity (~90%), indicating one major isoform of Atsttrin-α1 (FIG. 19B). Five of 17 cysteine residues within Atsttrin-α1 molecule exist as free thiols. When compared to TNFα, recombinant Atsttrin-α1 exhibited higher binding affinity for TNFR2, but lower affinity for TNFR1 (FIG. 4A). Atsttrin-α1 demonstrated dose-dependent inhibition of the interaction between TNFα and TNFR1/TNFR2 (FIGS. 4, B and C). Furthermore, Atsttrin-α1 also inhibited the binding of lymphotoxin a (LTα) to TNFR1 and TNFR2 (FIG. 20).

Figure 21:
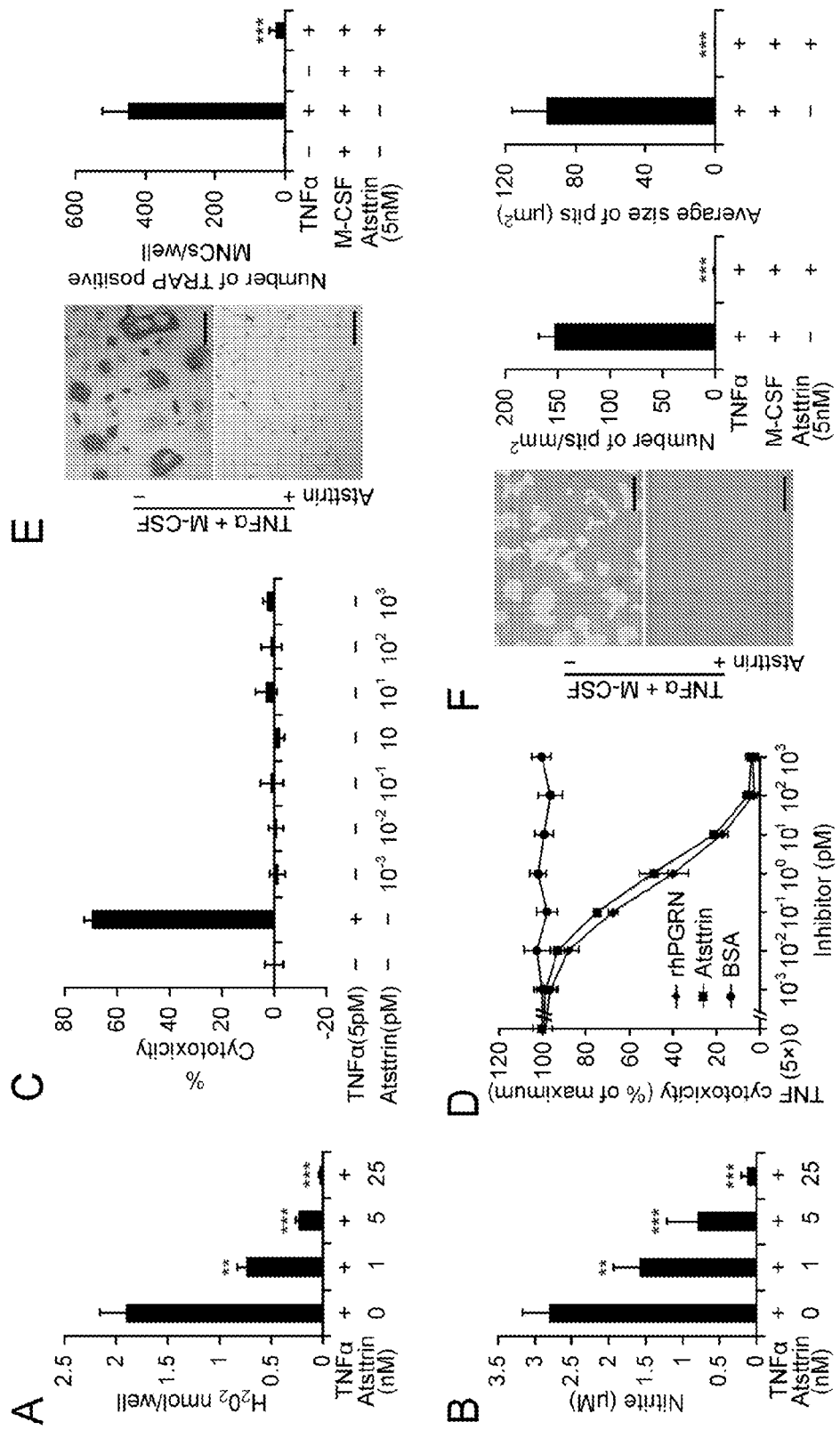
FIG. 21. Functional characteristics of Atsttrin-α1 polypeptide. (A) Atsttrin-al inhibits TNFα-induced $H_2O_2$ production in neutrophils. Neutrophils were treated with TNFα in the presence of various amounts of Atsttrin-α1, as indicated, and $H_2O_2$ production was measured. n=4. Values are mean± s.d. P<0.01, *P<0.001. (B) Atsttrin-α1 inhibits TNFα induced nitrite production in bone marrow derived macrophages. M-CSF pretreated BMDMs were incubated with TNFα in the presence of various amounts of Atsttrin-α1, as indicated, and the supernatants were tested for NO production. n=4. Values are mean±s.d. P<0.01, *P<0.001. (C) Atsttrin-α1 does not exhibit cytotoxic effects in rhabdomyosarcoma A673/6 cells. Actinomycin D-treated A673/6 cells were incubated with varying concentrations of Atsttrin-α1 for 24 hours and stained with naphthol blue black. Absorbances were determined at 630 nm. Cells without treatment and cells treated with 80 pg/ml TNFα served as negative and positive controls, respectively. Values represent mean±s.d. (D) Atsttrin-α1 and PGRN neutralize TNFα-induced cytotoxicity in rhabdomyosarcoma A673/6 cells. The data are presented relative to the amount of killing by 80 pg/ml TNFα in the absence of inhibitors (as 100%). Values are mean±s.d. (E) Left panel: representative TRAP staining of TNFα stimulated culture in the presence or absence of Atsttrin-α1. TRAP staining indicates osteoclast formation. Scale bar, 50 μm. Right panel: mean number of TRAP-positive multinucleated cells (MNCs). Values are mean±s.d. *P<0.001 versus the control (TNFα+M-CSF) treatment group. (F) Left panel: representative photomicrographs of resorption pits. Scale bar, 50 μm. Middle and Right panel: mean number of pits and areas of osteoclast-mediated bone resorption. Values are mean± s.d. *P<0.001.

Atsttrin-α1 inhibits several downstream events of TNF/TNFR signaling. Atsttrin-α1 inhibited TNFα-dependent hydrogen peroxide production in neutrophils and nitric oxide production in BMDMs in a dose-dependent manner (FIGS. 21, A and B). However, even at high dosages, Atsttrin-α1 did not exhibit any cytotoxic effects (FIG. 21C). Furthermore, Atsttrin-α1 effectively blocked TNFα-mediated death of rhabdomyosarcoma A673/6 cells (FIG. 21D).

To examine the effects of TNFα on osteoclastogenesis, TNFα was administered to M-CSF-dependent mouse BMDMs, which induced differentiation of these cells into osteoclasts. Co-administration of Atsttrin-α1 led to a significantly lower number of TRAP-positive osteoclasts, when compared to the control (FIG. 21E), and reduced the number and mean size of bone resorption pits (FIG. 21F).

This example shows that Atsttrin-α1 is useful in methods for inhibiting TNFα or TNFR signaling, such as, for example, in the prevention or treatment of conditions caused by or resulting in TNFα or TNFR signaling. The example further shows that Atsttrin-α1 is useful in methods for inhibiting TNFα-dependent hydrogen peroxide production in neutrophils, nitric oxide production in BMDMs, TNFα-mediated death of rhabdomyosarcoma A673/6 cells, and TNFα-mediated osteoclastogenesis. Accordingly, the example shows that Atsttrin-α1 is useful in methods for the prevention or treatment of conditions in which these events are relevant.

Example 6

Figure 22:
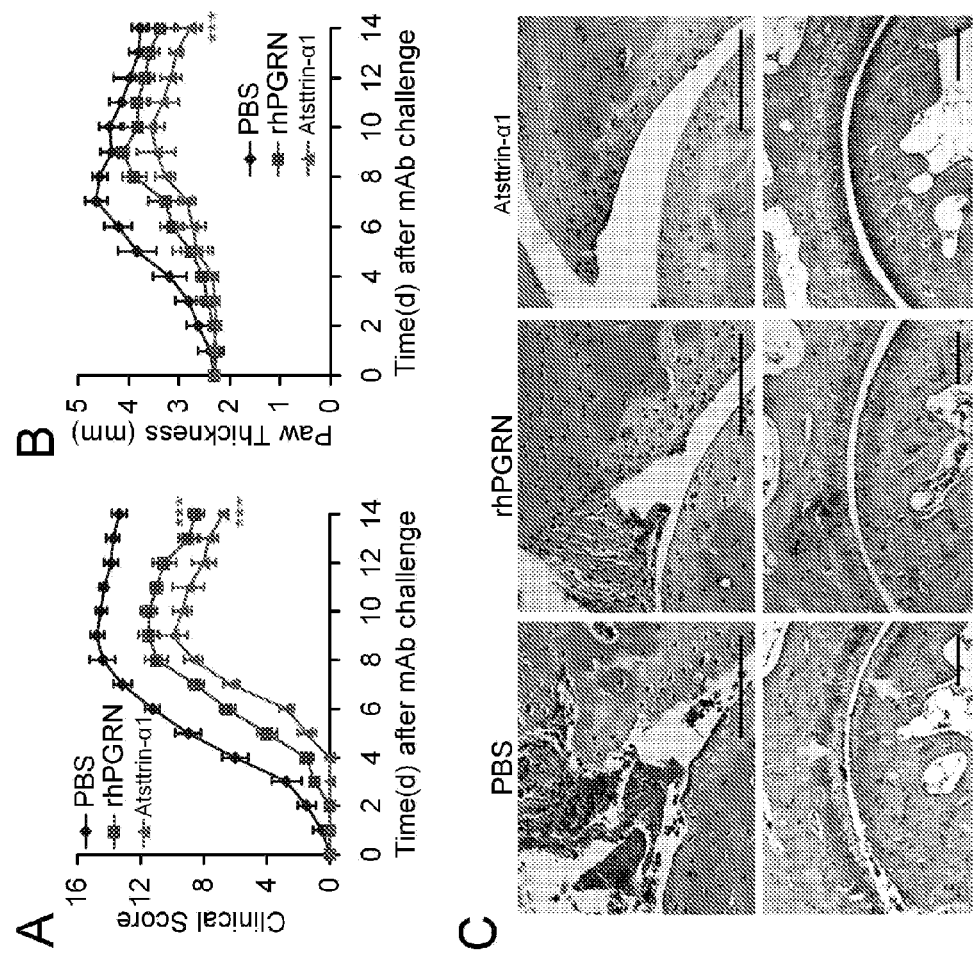
FIG. 22. Effects of PGRN and Atsttrin-α1 in experimental model of CAIA. (A) Arthritis severity and (B) paw thickness measurements in CAIA mice injected with PBS, rhPGRN or Atsttrin-α1 at 10 mg/kg body weight every other day (n=8/group). Values are mean±s.e.m. ***P<0.001 versus the control PBS group. (C) H&E (top) and Safranin O (bottom) stained sections of CAIA ankle joints on day 14 following collagen antibody challenge and treatment with PBS, rhPGRN or Atsttrin-α1. Arrows indicate loss of matrix staining. Scale bar, 100 μm.

Atsttrin-α1 Reduces TNFα-Mediated Inflammation in Murine Rheumatoid Arthritis Models The therapeutic effects of PGRN and Atsttrin-α1 were examined in two different mouse models of rheumatoid arthritis: collagen antibody-induced arthritis (CAIA) and collagen-induced arthritis (CIA). In the CAIA model, mice were challenged with a cocktail of anti-collagen antibodies and LPS and then randomized for treatment with rhPGRN, Atsttrin-α1, or PBS, starting on day 1. Administration of either rhPGRN or Atsttrin-α1 resulted in reduced disease severity in the CAIA model, and both agents significantly delayed the progression of arthritis (FIG. 22A). Furthermore, Atsttrin-α1 was more effective than rhPGRN in delaying the onset of inflammation (FIG. 22A). An analysis of paw thickness in the Atsttrin-α1-treated group showed a significant decrease in size to a nearly normal range compared to the PBS-treated group (FIG. 22B). Histological analysis of ankle joints indicated a significant decrease in inflammatory cell infiltration, tissue destruction, bone erosion, and loss of cartilage matrix in rhPGRN- and Atsttrin-α1-treated CAIA mice (FIG. 22C).

Figure 5:
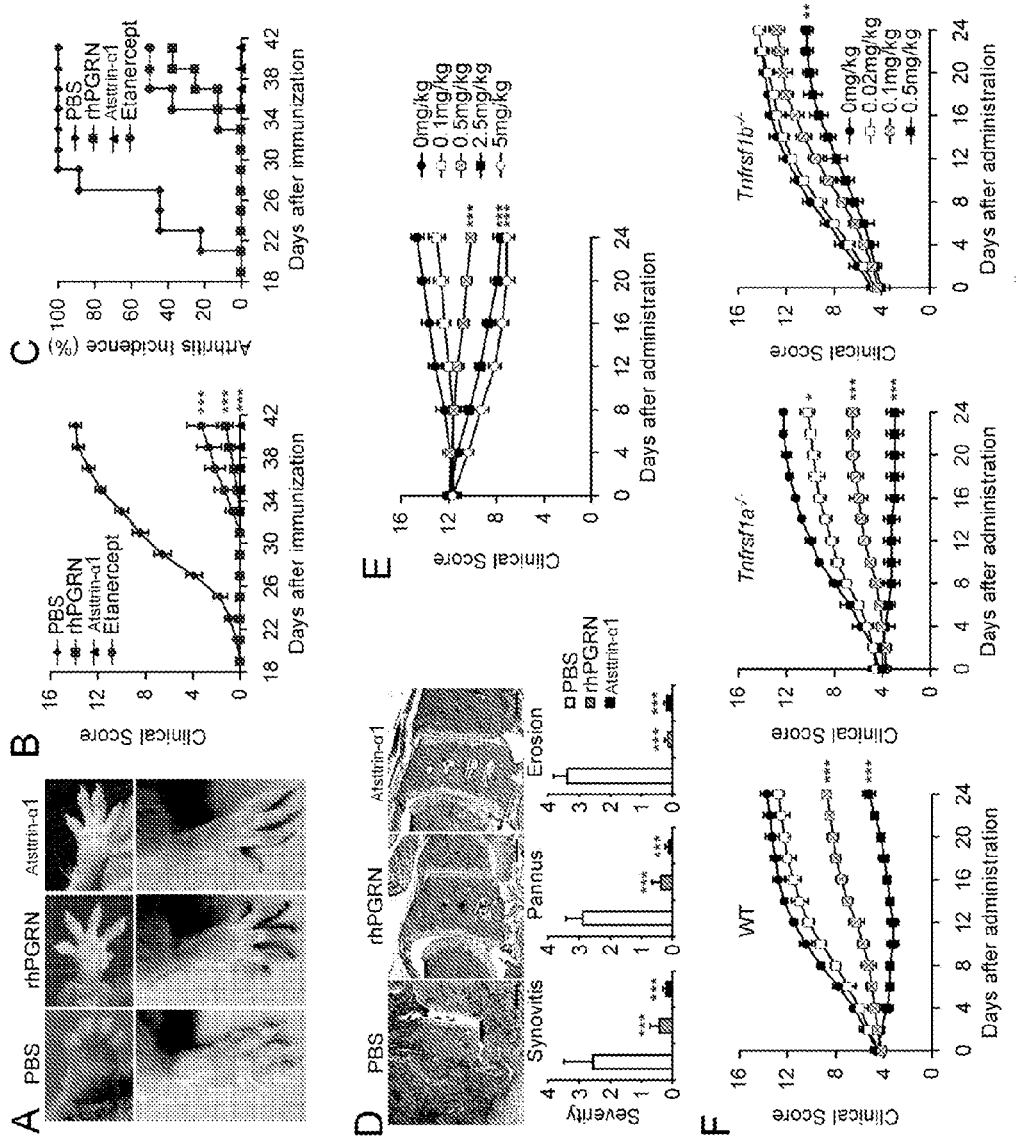
FIG. 5. Effects of PGRN and Atsttrin-α1 in CIA. (A) Photographs of paws of CIA mice treated with PBS, rhPGRN, or Atsttrin-α1. (B) Clinical arthritis scores in PBS (n=9), rhPGRN (n=8), Atsttrin-α1 (n=12) or Etanercept (n=8) treated CIA mice. Data are presented as the mean clinical score±s.e.m. *$P<0.001$ versus the control PBS group. (C) Incidence of arthritis in each treatment group. (D) H&E stained sections and evaluation of synovitis, pannus formation, and erosion of tarsal joints in CIA mice sacrificed at day 41 following primary immunization and treatment (starting day 19) with PBS, rhPGRN or Atsttrin-α1. Scale bar, 200 µm. Values are mean±s.d. *$P<0.001$ versus the control PBS group. (E) Therapeutic effects of Atsttrin-α1 in established CIA mice receiving intraperitoneal injections of indicated amounts of Atsttrin-α1 (mg per kg bodyweight once a week; n=8/group). Values are mean±s.e.m. ***$P<0.001$ versus the group of Atsttrin-α1 at a dose of 0. (F) Therapeutic effects of Atsttrin-α1 in established CIA of wild type, Tnfrsf1a$^{-/-}$, Tnfrsf1b$^{-/-}$ mice. Atsttrin-α1 was administered at 0.02, 0.1 or 0.5 mg per kg body weight once a week; n=8/group. Values are mean±s.e.m. *$P<0.05$, $P<0.01$, *$P<0.001$ versus the 0 mg/kg treatment group.
Figure 23:
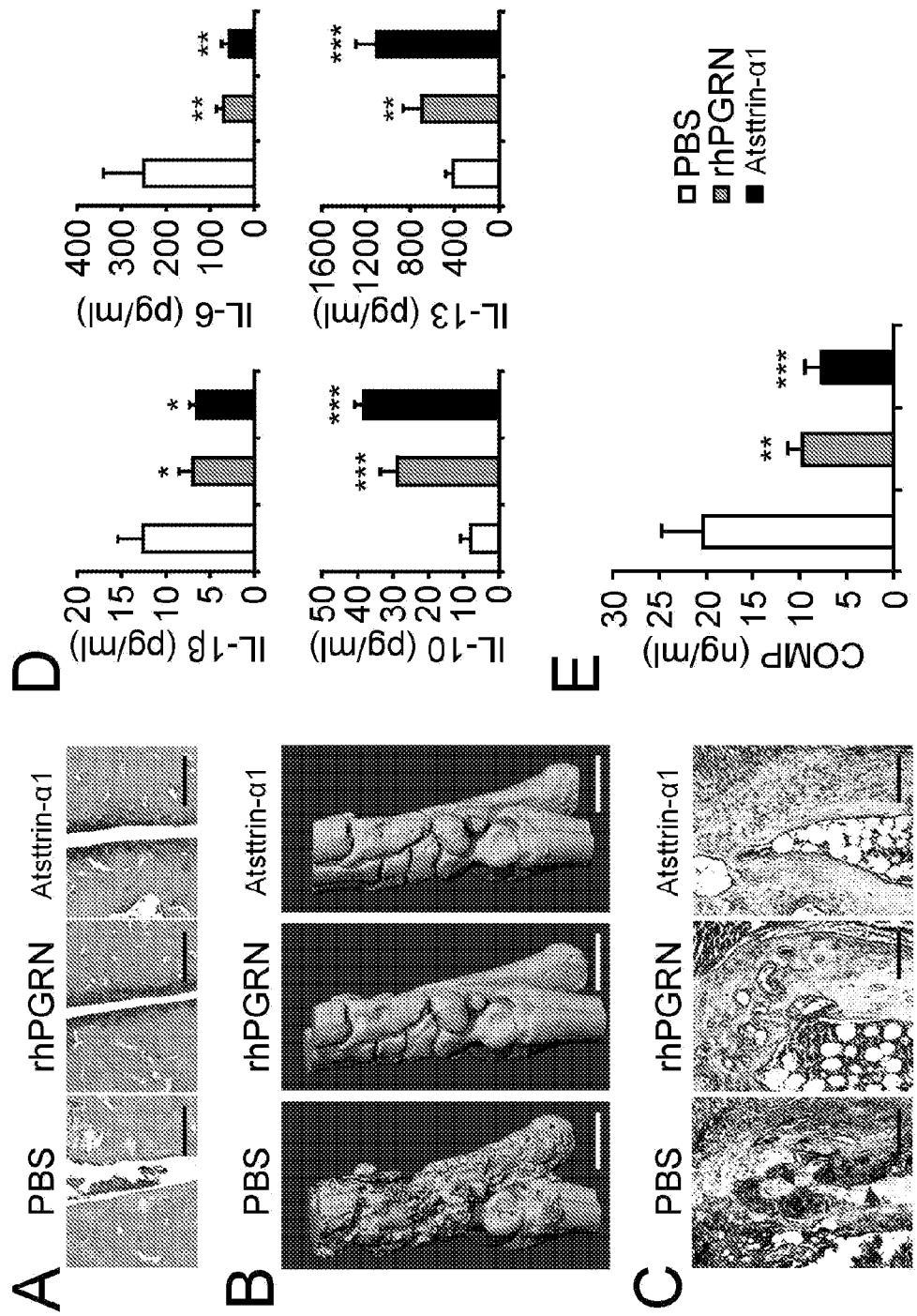
FIG. 23. Effects of PGRN and Atsttrin-α1 in experimental model of CIA. (A) Safranin O stained sections of CIA tarsal joints on day 41 following primary immunization and treatment with PBS or indicated antagonists. Arrows indicate loss of matrix staining Scale bar, 100 μm. (B) Three-dimensional microstructural analysis of ankle joints in CIA mice treated with PBS, rhPGRN or Atsttrin-α1. Specimens were scanned using micro-computed tomography. Scale bar, 1 mm. (C) TRAP stained sections of digital bones from each experimental group. TRAP[+] osteoclasts are indicated by arrows. Scale bar, 100 μm. (D, E) Serum levels of IL-1β, IL-6, IL-10 and IL-13, and COMP, as measured by ELISA on day 41 in each experimental group. Values are mean±s.d. *P<0.05, P<0.01, *P<0.001 versus the control PBS group.

In the CIA model, mice treated with rhPGRN or Atsttrin-α1 demonstrated markedly reduced joint swelling, erythema, and gross deformity compared to PBS-treated controls, with Atsttrin-α1-treated mice bearing marked similarity to normal mice (FIG. 5A). PGRN, Atsttrin-α1 and etanercept effectively prevented the development of arthritis, as evidenced by a decreased arthritis severity score and lower incidence of disease (FIGS. 5, B and C). Atsttrin-α1 was more effective than either rhPGRN or etanercept in this model, and completely prevented the onset of inflammation. Histological and quantitative analysis of the tarsal joints revealed essentially normal articular anatomy in the rhPGRN and Atsttrin-α1 treatment groups. In contrast, a robust infiltration of immune cells, tissue destruction, bone erosion, and loss of cartilage matrix were observed in the PBS-treated control mice (FIG. 5D and FIG. 23A). Micro-CT images revealed gross bone damage in the PBS-treated CIA mice, but not in the rhPGRNor Atsttrin-α1-treated groups (FIG. 23B). Furthermore, osteoclast activity was undetectable in both rhPGRN and Atsttrin-α1 treated CIA mice (FIG. 23C). Mice treated with rhPGRN or Atsttrin-α1 also had significantly decreased serum levels of proinflammatory cytokines interleukin (IL)-1β and IL-6, and COMP, and elevated levels of anti-inflammatory cytokines IL-10 and IL-13, when compared with control mice (FIGS. 23, D and E).

This example shows that Atsttrin-α1 is useful in methods for the reduction of inflammation, tissue loss, and cartilage matrix loss associated with arthritis, such as in the prevention or treatment of conditions resulting in or caused by such. The example shows that Atsttrin-α1 is effective in both the prevention and treatment of arthritis and symptoms associated with arthritis.

Example 7

Characterization of Atsttrin-α1 Pharmacokinetics and Therapeutic Specificity

Figure 24:
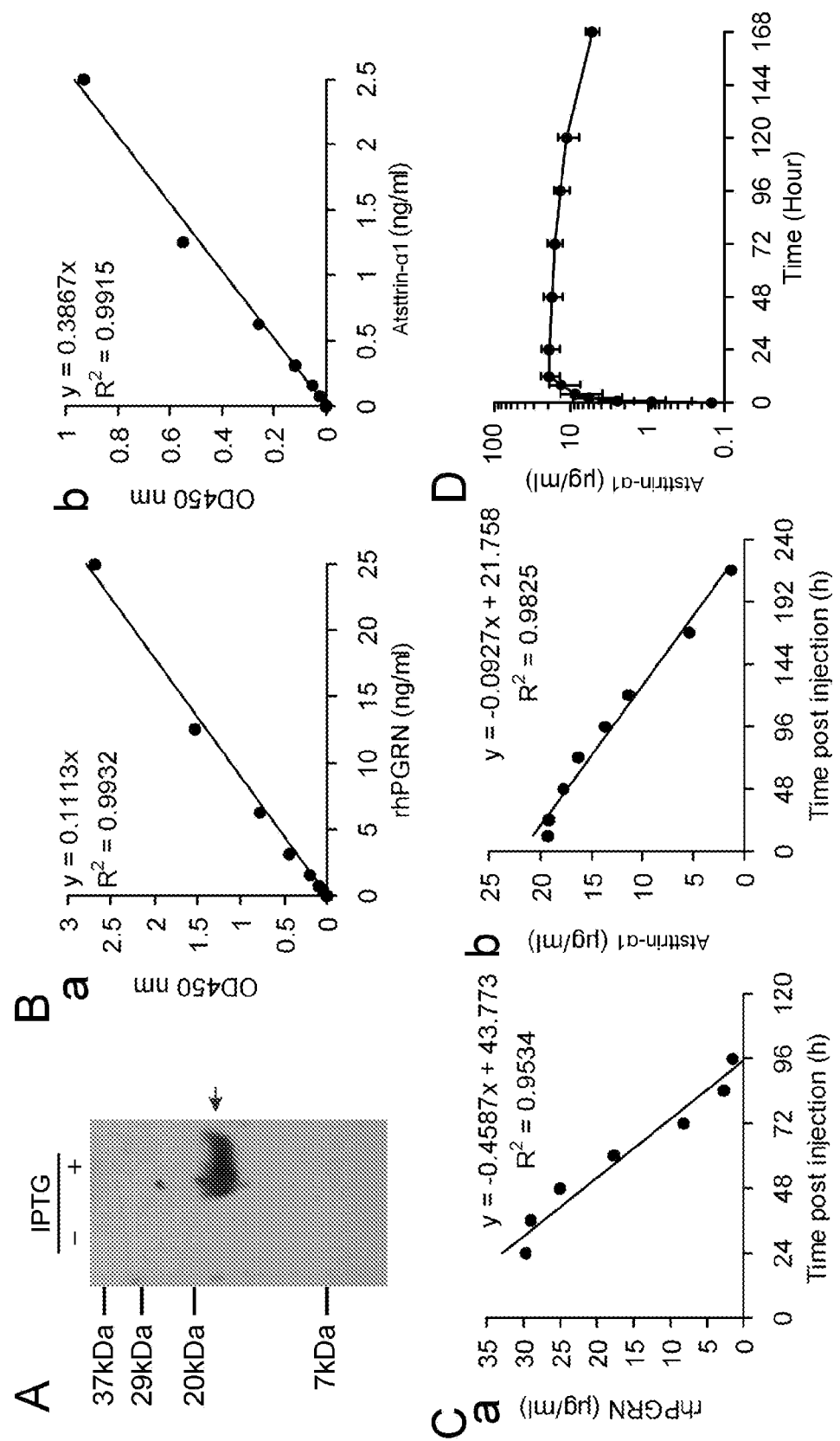
FIG. 24. (A) Characterization of affinity-purified polyclonal antibodies against Atsttrin-α1. Bacterial DE3 strain bearing the pET9d-Atsttrin-α1' was cultured for 3 hours, followed by the induction with 0.5 mM IPTG for 2 more hours, and the cell extracts were separated by SDS-PAGE, followed by the detection with affinity-purified anti-Atsttrin-α1 antibodies. (B) Standard curves for indirect ELISA assays for PGRN (a) and Atsttrin-α1 (b). (C) Pharmacokinetic profiles of PGRN and Atsttrin-α1 in mice. PGRN-deficient mice received a single i.p. injection of 2.4 mg/kg rhPGRN or 1.2 mg/kg Atsttrin-α1. At various time points, blood was collected and serum levels of PGRN (a) or Atsttrin-α1 (b) were determined by indirect ELISA. Values represent mean±s.d. PGRN and Atsttrin-α1 were found to have half-lives of ~40 hours and ~120 hours, respectively. (D) Pharmacokinetic profile of Atsttrin-α1 in mice. PGRN deficient mice that received a single i.p. injection of Atsttrin-α1 (1.2 mg/kg) were bled at the designated time points (3 mice per time point). The serum concentration of Atsttrin-α1 was determined by an indirect ELISA using anti-Atsttrin-α1 antibody. Values are mean±s.d.
Figure 25:
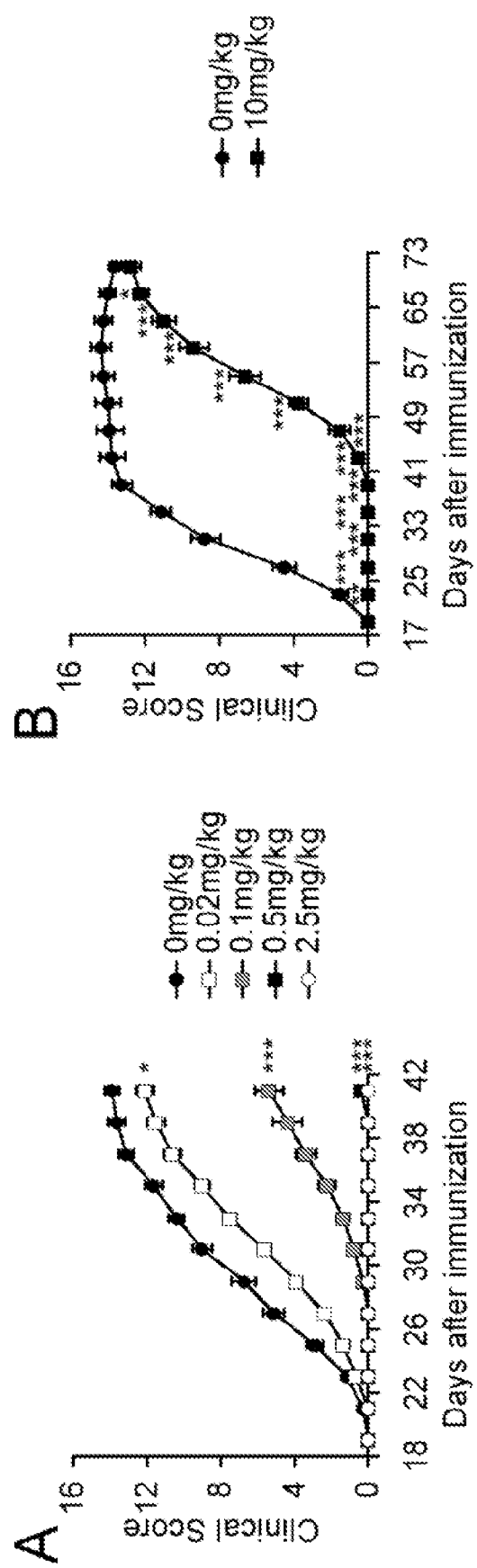
FIG. 25. Therapeutic efficacy of Atsttrin-α1 in CIA mice. (A) Dose dependency assay of Atsttrin-α1 in CIA mice. Atsttrin-α1 was administered at 0.02, 0.1, 0.5, or 2.5 mg per kg body once a week; n=8/group. Values are mean± s.e.m. *P<0.05, ***P<0.001 versus the control PBS group. (B) A single dose of Atsttrin-α1 (10 mg/kg) could effectively delay the onset of inflammation for approximately three weeks in CIA mice. Atsttrin-α1 was administered at day 19 after collagen II challenge; n=8/group. Values are mean±s.e.m. *P<0.05, P<0.01, *P<0.001 versus the PBS group.

To determine the pharmacokinetic profile of Atsttrin-α1, anti-serum was generated by immunizing mice with recombinant Atsttrin-α1. The specificity of anti-Atsttrin-α1 antibodies was confirmed by immunoblotting (FIG. 24A). An indirect ELISA using anti-Atsttrin-α1 antibody was then established (FIG. 24B), and the pharmacokinetic profile of Atsttrin-α1 in mice was examined. Atsttrin-α1 was well absorbed following intraperitoneal administration and demonstrated high stability with a half-life of about 120 hours (FIGS. 24, C and D). From these data, the pharmacokinetic parameters and availability were then calculated (Table 2). These results were used to determine the optimal dose of Atsttrin-α1 required to prevent CIA using a long dosing interval by injecting collagen-induced mice with Atsttrin-α1 once per week. The anti-inflammatory actions of Atsttrin-α1 displayed dose-dependency (FIG. 25A), and administration of Atsttrin-α1 at a dose of 0.5 mg/kg body weight or higher completely prevented the induction of arthritis. Results showed that a single dose of Atsttrin-α1 (10 mg/kg) could effectively delay the onset of inflammation for approximately three weeks (FIG. 25B). Taken together, these findings demonstrate that PGRN and Atsttrin-α1 can effectively prevent CIA in mice.

TABLE 2

Pharmacokinetic Parameters of Atsttrin-α1

| | |
|---|---|
| $C_{max}$ (μg/ml)[1] | 19.3 |
| $T_{max}$ (hour)[2] | 12 |
| Terminal half-life (day) | 5.0 |
| Availability (%)[3] | 85.5 |

[1]The maximum concentration
[2]The time of reaching maximum concentration
[3]Percentage of i.p. dose that reaches blood sampling compartment The therapeutic efficacy of Atsttrin-α1 in treating established CIA was also examined. Administration of Atsttrin-α1 once per week effectively inhibited or reversed disease progression in a dose-dependent manner (FIG. 5E).

Figure 26:
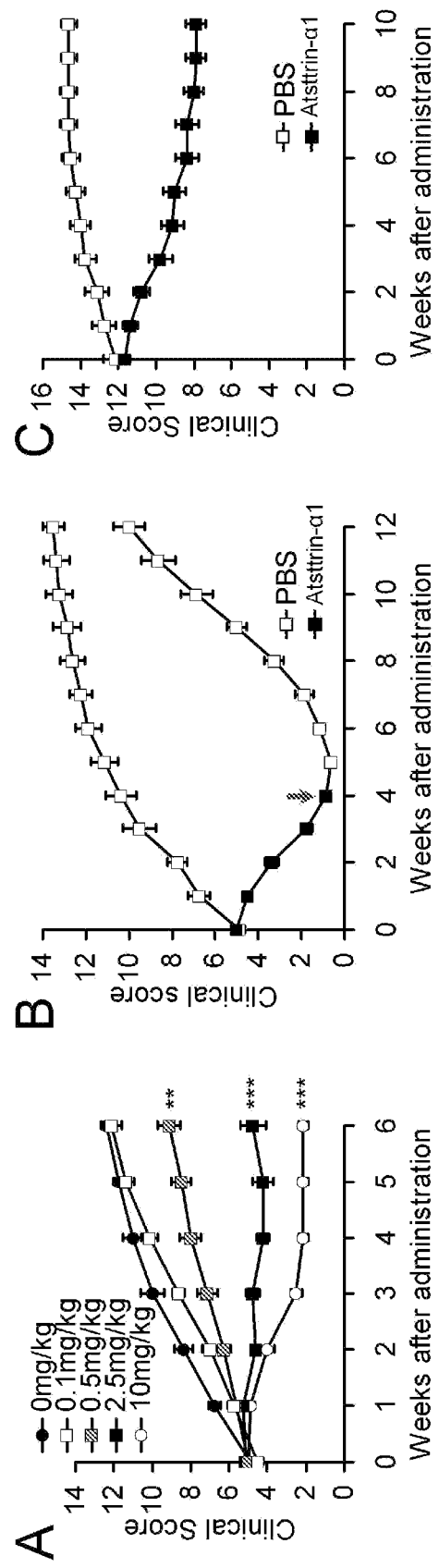
FIG. 26. Therapeutic efficacy of PGRN and Atsttrin-α1 in TNF-Tg mice. (A) Dose dependency assay of PGRN's therapeutic effect in TNF-Tg mice. rhPGRN was administered at 0.1, 0.5, 2.5, or 10 mg per kg body twice a week; n=8/group. Values are mean±s.e.m. P<0.01, *P<0.001 versus the control PBS (0 mg/kg) group. (B) Administration of Atsttrin-α1 (2.5 mg/kg body weight) twice every week led to the reversal of inflammation in TNF-Tg mice with mild arthritis (n=8; arthritic score ~5). In contrast, inflammatory arthritis was relapsed and gradually progressed following the discontinuation of Atsttrin-α1. Arrow indicates the time point when Atsttrin-α1 treatment was ceased. (C) Atsttrin-α1 treatment of TNF-Tg mice with severe arthritis. TNF-Tg mice with severe arthritis (n=8; arthritic score ~12) treated with Atsttrin-α1 at the same dose and time interval as in (B) ameliorated the severity of inflammation. Data presented as the mean clinical score±s.e.m.

The therapeutic effects of Atsttrin-α1 in TNF-Tg mice was also confirmed. Consistent with the results observed in the CIA model, the administration of Atsttrin-α1 markedly suppressed arthritis progression, and eliminated signs of inflammation (FIG. 26). Signs of inflammation returned following the cessation of Atsttrin-α1 treatment (FIG. 26B).

To define the contributions of TNFR1 and TNFR2 in the therapeutic effects of Atsttrin-α1, the effects of Atsttrin-α1 on CIA in wildtype and mice lacking TNFR1 (Tnfrsf1a−/−) or TNFR2 (Tnfrsf1b−/−) were compared (FIG. 5F). Atsttrin-α1 treatment was effective in both wildtype and Tnfrsf1a−/− mice in a dose-dependent fashion. In contrast, only the highest dose of Atsttrin-α1 (0.5 mg/kg) exerted a significant effect in Tnfrsf1b−/− mice. These data indicated that Tnfrsf1b−/− CIA mice are less sensitive to Atsttrin-α1 treatment. Without wishing to be bound by theory, it is possible that Atsttrin-α1 binds to TNFR2 with a higher affinity than to TNFR1, or that the results stem from differences in the distributions and/or functions of TNFR1 and TNFR2 in T cells.

This example shows that Atsttrin-α1 is useful in methods comprising administration of Atsttrin-α1 to animal subjects to reduce inflammation associated with arthritis. In particular, the example shows that Atsttrin-α1 is useful in methods for reducing arthritic inflammation mediated by TNFα, TNFR 1, or TNFR2. The example shows that Atsttrin-α1 is effective in both the prevention and treatment of arthritis and symptoms associated with arthritis.

Example 8

PGRN and Atsttrin-α1 Inhibit TNFα-Induced Activation of NF-κB and MAPK

Figure 6:
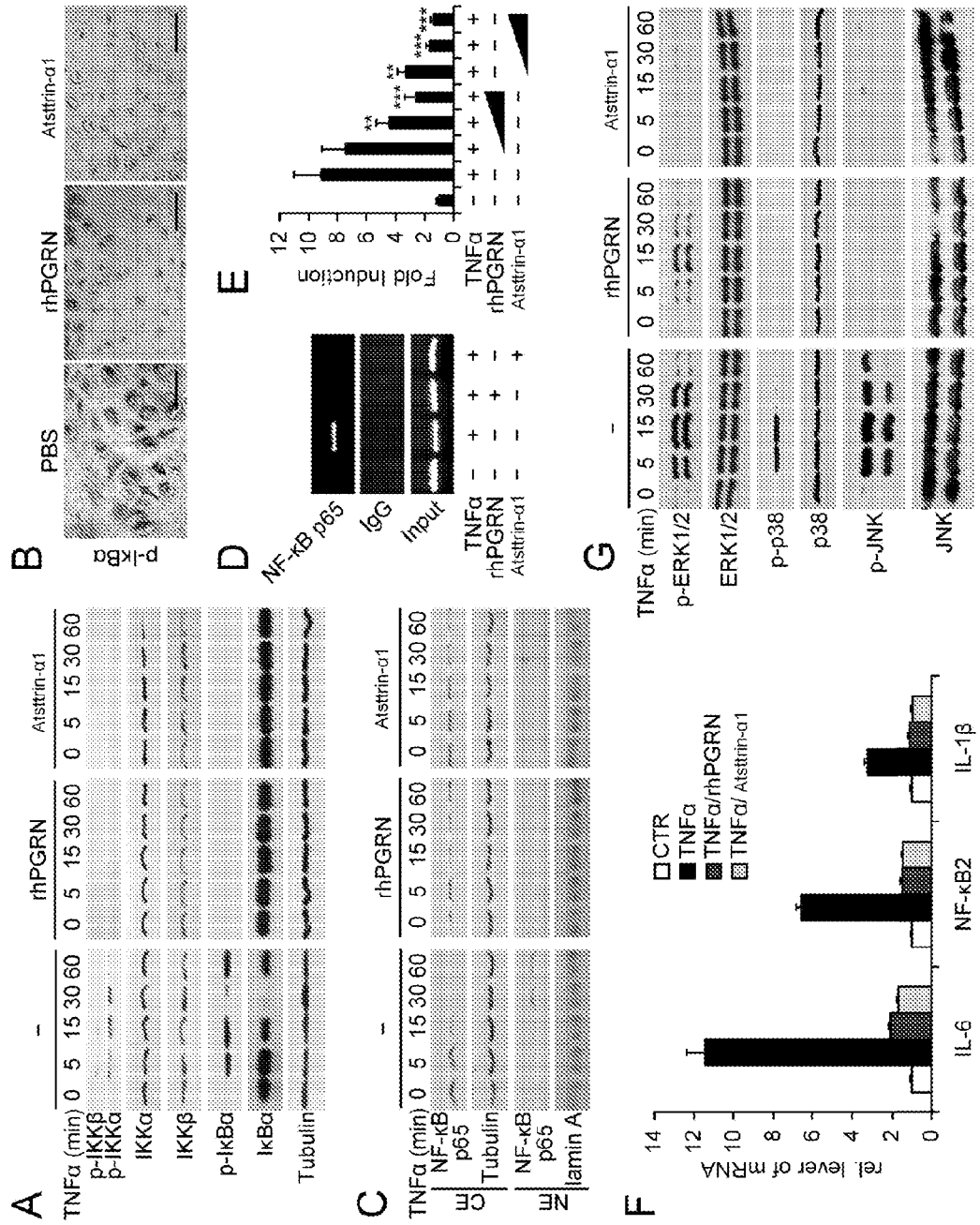
FIG. 6. PGRN and Atsttrin-α1 inhibit TNFα-mediated activation of NF-κB and MAPK signaling. (A) BMDMs were incubated with TNFα in the presence or absence of rhPGRN or Atsttrin-α1, and phosphorylation and expression of the indicated signaling molecules at various time points were determined by immunoblotting. Tubulin is shown as a loading control. (B) Immunohistochemistry for phosphorylated IκBα in the articular cartilage of CIA mice on day 41 following primary immunization and treatment with PBS, rhPGRN or Atsttrin-α1. Arrows indicate phosphorylated IκBα. Scale bar, 25 μm. (C) NF-κB amounts were analyzed by Western blotting with p65 antibody and assessed using cytoplasmic (CE) and nuclear (NE) extracts of TNFα-treated BMDMs in the presence and absence of rhPGRN or Atsttrin-α1. Tubulin and lamin A serve as cytoplasmic and nuclear controls, respectively. (D) BMDMs were incubated with TNFα in the presence or absence of rhPGRN or Atsttrin-α1 for 6 h, and analyzed by chromatin immunoprecipitation (ChIP) assay. (E) BMDMs transfected with the NF-κB-dependent reporter construct were incubated with TNFα (10 ng/ml) in the presence of increasing concentrations of rhPGRN or Atsttrin-α1 (0.1, 0.5, 2.5 nM), and the luciferase activity was measured. Values are mean±s.d. P<0.01, *P<0.001 versus TNFα-stimulated cells. (F) The order change of mRNA expression relative to unstimulated cells, as assessed by real time PCR. (G) PGRN and Atsttrin-α1 inhibit TNFα-induced ERK1/2, p38 and JNK phosphorylation. BMDMs were stimulated with TNFα in the presence or absence of rhPGRN or Atsttrin-α1. At the indicated time points, cell lysates were probed using specific antibodies against total and phosphorylated Erk1/2, p38, and JNK.
Figure 7:
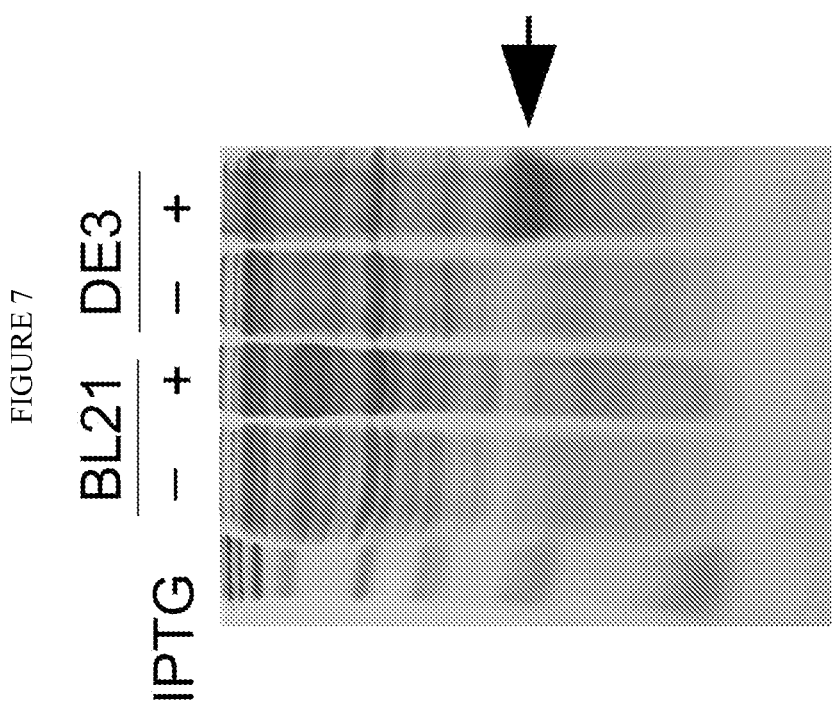
FIG. 7. Visualization of Atsttrin-α1 (arrow) expressed from the pET9d vector by SDS-PAGE.

To explore further the anti-inflammatory mechanisms of PGRN and Atsttrin-α1, the role of PGRN and Atsttrin-α1 in TNFα-induced activation of IKK/IκB/NF-κB signaling was examined. Results showed that rhPGRN and Atsttrin-α1 blocked TNFα-induced phosphorylation of IKK and IκBα and the degradation of IκBα in BMDMs (FIG. 6A). Results also showed elevated IκBα phosphorylation in the tarsal joint articular cartilage of mice with CIA, which was abolished by treatment with rhPGRN or Atsttrin-α1 (FIG. 6B). rhPGRN or Atsttrin-α1 treatment of BMDMs impaired TNFα-induced NF-κB nuclear translocation, NF-κB binding to the IκBα promoter and activation of gene expression by NF-κB (FIG. 6, C-F). rhPGRN and Atsttrin-α1 also inhibited the TNFα-induced phosphorylation of p38, JNK and ERK1/2, mitogen activated protein kinase (MAPK) family members known to play an important role in TNFα-mediated inflammation (FIG. 6G). While Atsttrin-α1 completely blocked the TNFα-induced phosphorylation of ERK1/2, the presence of rhPGRN only resulted in a partial inhibition of this pathway. These results are consistent with the previous finding that PGRN activates ERK1/2 signaling. Taken together, these results demonstrate that PGRN and Atsttrin-α1 inhibit multiple TNFα-induced intracellular signaling pathways.

Collectively, these findings demonstrate that PGRN is a key regulator of inflammation and that PGRN mediates its anti-inflammatory effects, at least in part, by blocking TNF binding to its receptors.

These Examples show that Atsttrin-α1 and recombinant human PGRN are useful in methods for inhibition of TNFα signaling mediated by TNFR1 and TNFR2, such as, for example in the treatment or prevention of conditions caused by or resulting in TNFα signaling. In particular, the examples show that Atsttrin-α1 is useful in methods comprising administration of Atsttrin-α1 to animal subjects for the reduction of inflammation and tissue damage caused by or resulting from arthritis.

Example 9

Expression of Atsttrin-α Variants

For expression of Atsttrin-α variants lacking the GST fusion protein, the appropriate plasmid pGEX-Atsttrin-α was transformed into *E. coli* DE3. Four different variants were made and tested: Atsttrin-α3 (SEQ ID NO: 5), Atsttrin-α4 (SEQ ID NO: 6), Atsttrin-α5 (SEQ ID NO: 7), and Atsttrin-α6 (SEQ ID NO: 8). No expression of the protein was observed in the E. coli transformed with Atsttrin-α3, Atsttrin-α4, or Atsttrin-α5. However, Atsttrin-α6 expressed at levels comparable to that of the Atsttrin-α1 GST fusion protein. These results indicate that the presence of certain amino acids at the N-terminus of the protein are important for the proper expression of the protein in bacterial cells.

EQUIVALENTS

The present technology is not to be limited in terms of the particular embodiments described in this application, which are intended as single illustrations of individual aspects of the technology. Many modifications and variations of this technology can be made without departing from its spirit and scope, as will be apparent to those skilled in the art. Functionally equivalent methods and apparatuses within the scope of the technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. An isolated peptide comprising the contiguous sequence of SEQ ID NO:4 and having 90%-99.4% sequence identity to SEQ ID NO:4.

2. The isolated peptide of claim 1, wherein the peptide comprises SEQ ID NO:3.

3. The isolated peptide of claim 1, wherein the peptide comprises SEQ ID NO:5.

4. The isolated peptide of claim 1, wherein the peptide comprises SEQ ID NO:6.

5. The isolated peptide of claim 1, wherein the peptide comprises SEQ ID NO:7.

6. The isolated peptide of claim 1, wherein the peptide comprises SEQ ID NO:8.

7. A composition comprising SEQ ID NO:3, SEQ ID NO:5, SEQ ID NO:6, SEQ ID NO:7, or SEQ ID NO:8, and a pharmaceutically acceptable carrier.

8. The composition of claim 7, further comprising one or more of an anti-inflammatory agent, an anti-cancer agent, and an immunomodulatory agent.

9. A method for treating arthritis, comprising administering to a subject in need thereof an effective amount of a pharmaceutical composition comprising SEQ ID NO:3, SEQ ID NO:5, SEQ ID NO:6, SEQ ID NO:7, or SEQ ID NO:8.

10. The method of claim 9, wherein the arthritis comprises rheumatoid arthritis, osteoarthritis, ankylosing spondylitis, or juvenile idiopathic arthritis.

11. The method of claim 9, wherein the pharmaceutical composition comprises one or more of an anti-inflammatory agent or compound, an anti-cancer agent or compound, and an immunomodulatory agent.

* * * * *

UNITED STATES PATENT AND TRADEMARK OFFICE
CERTIFICATE OF CORRECTION

PATENT NO. : 9,403,891 B2
APPLICATION NO. : 14/003756
DATED : August 2, 2016
INVENTOR(S) : Chuan-Ju Liu Page 1 of 1

It is certified that error appears in the above-identified patent and that said Letters Patent is hereby corrected as shown below:

In the Specification

In Column 1, Lines 16-19, please delete "This invention was made with government support under AR050620, AR053210, AR040072, GM061710, and AI43542 awarded by the National Institutes of Health. The government has certain rights in the invention." and insert -- This invention was made with government support under grant numbers AR050620, AR053210, GM061710, AI043542 and AR040072 awarded by The National Institutes of Health. The government has certain rights in the invention. --

Signed and Sealed this
First Day of April, 2025

Coke Morgan Stewart
*Acting Director of the United States Patent and Trademark Office*